United States Patent [19]

Kluender et al.

[11] Patent Number: 4,742,080

[45] Date of Patent: May 3, 1988

[54] THERAPEUTIC METHOD FOR PRODUCING BRONCHODILATION BY ADMINISTRATION OF 15-DEOXY-16-HYDROXY PROSTAGLANDIN ESTERS

[75] Inventors: Harold C. Kluender, South Bend, Ind.; Warren D. Woesner, New York, N.Y.; William G. Biddlecom, Elkhart, Ind.

[73] Assignee: Miles Laboratories, Inc., Elkhart, Ind.

[21] Appl. No.: 712,910

[22] Filed: Mar. 15, 1985

Related U.S. Application Data

[60] Continuation of Ser. No. 549,090, Nov. 7, 1983, abandoned, which is a division of Ser. No. 357,428, Mar. 12, 1983, Pat. No. 4,415,592, which is a division of Ser. No. 215,802, Dec. 12, 1980, Pat. No. 4,331,688, which is a division of Ser. No. 973,010, Dec. 12, 1978, Pat. No. 4,275,224, which is a division of Ser. No. 880,501, Feb. 23, 1978, Pat. No. 4,132,738.

[51] Int. Cl.$^4$ ............................................ A61K 31/215
[52] U.S. Cl. .................................. 514/530; 514/572;
[58] Field of Search ......................................... 514/530

[56] References Cited

U.S. PATENT DOCUMENTS

| | | | |
|---|---|---|---|
| 3,922,305 | 11/1975 | Engelhardt | 424/305 |
| 3,925,451 | 12/1975 | Sakai et al. | 424/305 |
| 3,965,143 | 6/1976 | Collins et al. | |

Primary Examiner—Sam Rosen
Attorney, Agent, or Firm—Mary G. Boguslaski; Edward P. Gray

[57] ABSTRACT

A therapeutic method for producing bronchodilation in an individual for whom such therapy is indicated is disclosed. The method comprises administering to said individual an effective bronchodilation amount of certain derivatives of 15-deoxy-16-hydroxy-prostaglandin $E_1$ esters.

9 Claims, No Drawings

THERAPEUTIC METHOD FOR PRODUCING BRONCHODILATION BY ADMINISTRATION OF 15-DEOXY-16-HYDROXY PROSTAGLANDIN ESTERS

This is a continuation of application Ser. No. 549,090, filed Nov. 7, 1983, now abandoned, which is a division of application Ser. No. 357,428, filed Mar. 12, 1983, now U.S. Pat. No. 4,415,592; which is a division of Ser. No. 215,802 filed Dec. 12, 1980, now U.S. Pat. No. 4,331,688; which is a division of Ser. No. 973,010 filed Dec. 12, 1978, now U.S. Pat. No. 4,275,224; which is a division of Ser. No. 880,501, filed Feb. 23, 1978, now U.S. Pat. No. 4,132,738.

BACKGROUND OF THE INVENTION

1. Field of the Invention

The compounds of this invention are analogues of natural prostaglandins.

Natural prostaglandins are alicyclic compounds related to prostanoic acid, the structure of which is:

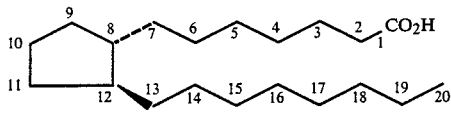

By convention, the carbon atoms of I are numbered sequentially from the carboxylic carbon atom. An important stereochemical feature of I is the trans-orientation of the sidechains $C_1$–$C_7$ and $C_{13}$–$C_{20}$, an orientation common to all natural prostaglandins. In I, as elsewhere in this specification, solid lines (———) provide a reference plane (such as the cyclopentyl ring or the bonds among atoms $C_1$–$C_7$ and $C_{13}$–$C_{20}$); a dashed line (----) indicates projection of a covalent bond below such reference plane (alpha-configuration); while a wedged line (▬) represents direction above such plane (beta-configuration). Those conventions apply to all structural formula subsequently discussed in this specification. In some structures, however, a swung dash or serpentine line (~) denotes orientation of a covalent bond either above or below a plane of reference (indicated by the Greek letter xi in the nomenclature of such structures).

Natural prostaglandins have the general structure,

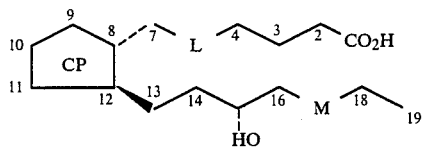

in which: L and M may be ethylene or cis-vinylene radicals; and the cyclopentyl ring

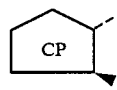

may be:

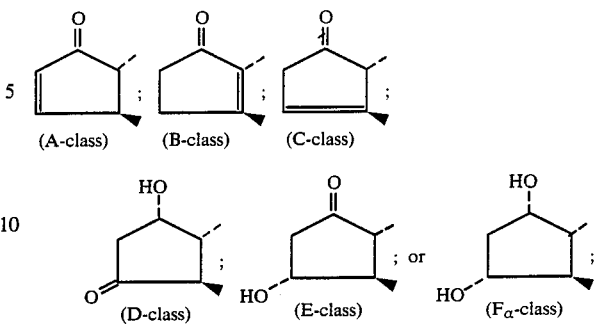

Formula II and all representations of the cyclopentyl moiety depict the nat-isomer, i.e., the $C_7$–$C_8$ bond in the alpha-configuration and the $C_{12}$–$C_{13}$ bond in the beta-configuration. In the ent-isomer (which does not occur in nature), the direction of the bonds at $C_7$–$C_8$ and $C_{12}$–$C_{13}$ is reversed.

Prostaglandins are classified according to the functional groups present in the five-membered ring and the presence of double bonds in the ring or chains. Prostaglandins of the A-class (PGA or prostaglandin A) are characterized by an oxo group at $C_9$ and a double bond at $C_{10}$–$C_{11}$ ($\Delta^{10,11}$); those of the B-class (PGB) have an oxo group at $C_9$ and a double bond at $C_8$–$C_{12}$ ($\Delta^{8,12}$); compounds of the C-class (PGC) contain an oxo group at $C_9$ and a double bond at $C_{11}$–$C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the $F_\alpha$-class (PGF$_\alpha$) have an alpha-directed hydroxyl group at $C_9$ and an alpha-oriented hydroxyl group at $C_{11}$. Within each of the A, B, C, D, E, and F classes of prostaglandins are three subclassifications based upon the presence of double bonds in the side-chains at $C_5$–$C_6$, $C_{13}$–$C_{14}$, or $C_{17}$–$C_{18}$. The presence of a trans-unsaturated bond only at $C_{13}$–$C_{14}$ is indicated by the subscript numeral 1; thus, for example, PGE$_1$ (or prostaglandin E$_1$) denotes a prostaglandin of the E-type (oxo-group at $C_9$ and an alpha-hydroxyl at $C_{11}$) with a trans-double bond at $C_{13}$–$C_{14}$. The presence of both a trans-double bond at $C_{13}$–$C_{14}$ and a cis-double bond at $C_5$–$C_6$ is denoted by the subscript numeral 2; for example, PGE$_2$. Lastly, a trans-double bond at $C_{13}$–$C_{14}$, a cis-double bond at $C_5$–$C_6$ and a cis-double bond at $C_{17}$–$C_{18}$ is indicated by the subscript numeral 3; for example, PGE$_3$. The above notations apply to prostaglandins of the A, B, C, D, and F series as well; however, in the last, the alpha-orientation of the hydroxyl group at $C_9$ is indicated by the subscript Greek letter $\alpha$ after the numerical subscript.

Nomenclature of prostaglandins and their analogues deserves note insofar as there are three current systems followed in the scientific and patent literature. One system for convenience referred to as the Nelson system, uses the trivial names of prostaglandins and designates analogues by modifications of the trivial names (see—J. Med. Chem., 17; 911 [1974]). Another system follows the rules of the International Union of Pure and Applied Chemistry (IUPAC) and refers to prostaglandins and their analogues as derivatives of heptanoic acid. A third system employs a convention of Chemical Abstracts ("CA") that designates prostaglandins and derivatives thereof as derivatives of prostanoic acid. An example of each system is provided below for the following structure:

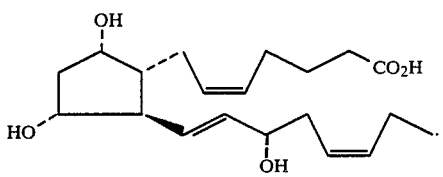

III

In the Nelson system, III is designated prostaglandin $F_{3\alpha}$ or $PGF_{3\alpha}$ (shortened form); in the IUPAC system, 7-[3R,5S-dihydroxy-2R-(3S-hydroxy-1E,5Z-octadienyl)-cyclopent-1R-yl]-5Z-heptenoic acid; in the CA system, (5Z,9α,11α,13E,15S,17Z)-9,11,15-trihydroxyprosta-5,13,17-trien-1-oic acid.

It is important to note that in all natural prostaglandins there is a hydroxyl group at $C_{15}$ oriented below the plane in which $C_{15}$ is located. In the Cahn-Ingold-Prelog system of defining stereochemistry, that $C_{15}$ hydroxyl group is in the S-configuration. Inversion of the orientation of the $C_{15}$ hydroxyl group such that the group projects above the plane in which the $C_{15}$ atom is located represents the R-configuration. The Cahn-Ingold-Prelog system is used to define stereochemistry of any asymmetric center outside of the carbocyclic ring in all three systems of nomenclature described above. In some literature, however, α,β designations are used for such centers.

Isomerism of a double bond is designated in all three systems by use of conventional prefixes cis- or trans-, or their respective equivalents, Z or E (as suggested in *J. Am. Chem. Soc.*, 59: 509 [1968]).

For details of other conventions utilized in nomenclature of prostaglandins, see: Nelson, N. A., "Prostaglandin Nomenclature", *J. Med. Chem.*, 17: 911 (1974).

Recent research indicates that prostaglandins appear ubiquitously in animal tissues and elicit biochemical and physiological effects in a variety of mammalian systems. In the endocrine system, for example, experimental evidence indicates prostaglandins influence the hormone synthesis or release of hormones in the secretory glands. In rats, $PGE_1$ and $PGE_2$ increase the release of the growth hormone while $PGA_1$ increases its synthesis. In sheep, $PGE_1$ and $PGF_{1\alpha}$ inhibit ovarian progesterone secretion. In a variety of mammals, $PGF_{1\alpha}$ and $PGF_{2\alpha}$ act as luteolytic factors. In mice, $PGE_1$, $PGE_2$, $PGF_{1\alpha}$ and $PGF_{1\beta}$ increase thyroid activity. In hypophysectomized rats, $PGE_1$, $PGE_2$ and $PGF_{1\alpha}$ stimulate stereoidogenesis in the adrenal glands.

In the mammalian male reproductive system, $PGE_1$ contracts the smooth muscle of the vas deferens. In the female reproductive system, PGE and $PGF_\alpha$ compounds contract uterine smooth muscle. In general, PGE, PGB and PGA compounds relax in vitro human uterine muscle strips, while those of the $PGF_\alpha$ class contract such isolated preparations. PGE compounds, in general, promote fertility in the female reproductive system while $PGF_{2\alpha}$ has contragestational effects. $PGF_{2\alpha}$ also appears to be involved in the mechanism of menstruation. In general, $PGE_2$ produces potent oxytocic effects in inducing labor, while $PGF_{2\alpha}$ induces spontaneous abortions in early pregnancy.

$PGF_\alpha$ and PGE compounds have been isolated from a variety of nervous tissues. $PGE_1$ retards whereas $PGF_{2\alpha}$ facilitates transmission along motor pathways in the central nervous system. $PGE_1$ and $PGE_2$ reportedly inhibit transmitter release from adrenergic nerve endings in the guinea pig.

Prostaglandins stimulate contraction of gastrointestinal smooth muscle in vivo and in vitro. In dogs, $PGA_1$, $PGE_1$, and $PGE_2$ inhibit gastric secretion. $PGA_1$ exhibits similar activity in man. Natural prostaglandins and some of their analogues also protect gastric mucosa from ulceration induced by nonstereoidal antiinflammatory agents.

In most mammalian respiratory tracts, PGE and PGF compounds affect in vitro preparations of tracheal smooth muscle. Specifically, $PGE_1$ and $PGE_2$ relax while $PGF_{2\alpha}$ contracts such smooth muscle. The human lung normally contains PGE and PGF compounds; consequently, some cases of bronchial asthma may involve an imbalance in the production or metabolism of those compounds.

Prostaglandins are involved in certain hematic mechanisms in mammals. $PGE_1$, for example, inhibits aggregation of blood platelets in vitro.

In a variety of mammalian cardiovascular systems, compounds of the PGE and PGA classes are vasodilators whereas those of the $PGF_\alpha$ class are vasoconstrictors, by virtue of their action on vascular smooth muscle.

Prostaglandins naturally appear in the kidney and reverse experimental and clinical renoprival hypertension.

The prostaglandins and their analogues have broad clinical implications. In obstetrics and gynecology, they may find use in fertility control, treatment of menstrual disorders, the induction of labor, and the correction of hormone disorders. In gastroenterology, they may help treat or prevent peptic ulcers and various disorders involving motility, secretion, and absorption in the gastrointestinal tract. They may, in the respiratory area, prove beneficial in the therapy of bronchial asthma and other diseases involving bronchoconstriction. In hematology, they may display utility as anti-clotting agents in diseases such as venous thrombosis, thrombotic coronary occlusion and other diseases involving thrombi. For circulatory diseases, they have therapeutic utility in hypertension, peripheral vasopathies and cardiac disorders.

The following references include a more complete review of the chemical, physiological and pharmacological aspects of the prostaglandins: *The Prostaglandins*, Vol. I., P. Ramwell, Ed., New York, Plenum Press, 1973; Ann. N.Y. *Acad. Sci.*, 180; 1–568 (1971); Higgins and Braunwald, *J. Am. Med. Assn.*, 53: 92–112 (1972); Osterling, Marozowich, and Roseman, *J. Phar. Sci.*, 61: 1861–1895 (1972); and Nakano, *Resident and Staff Phys.*, 19: 92, 94–99, and 102–106 (1973).

2. Description of the Prior Art

A. Prior art relevant to the claimed carbinol 16-hydroxy prostaglandin analogues is disclosed in published Netherlands application No. 75-03553, U.S. application Ser. No. 454,913 assigned to G. D. Searle & Co., hereafter referred to as "Searle" now U.S. Pat. No. 3,965,143. Searle is directed to 16-hydroxy prostaglandin analogues which are acids and esters. Searle's broad generic disclosure is represented by:

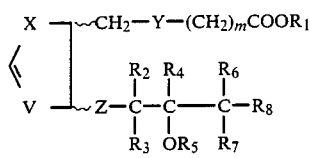

where $R_1$, $R_2$, $R_3$, $R_4$, $R_6$ and $R_7$ can be hydrogen or a lower-alkyl radical and $R_8$ is an alkyl group containing 3–5 carbon atoms or a cycloalkly group containing 5–7 carbon atoms.

Compounds disclosed by Searle which are most structurally similar to the claimed compounds of the present invention are shown below.

SEARLE EXAMPLE 12

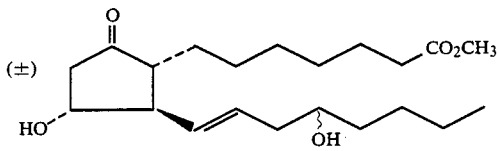

Racemic methyl 7-[3(R)-hydroxy-2β-(4(R)-hydroxy-trans-1-octenyl)-5-oxocyclopentane]-1α-heptanoate (the methyl ester analogous to presently claimed TR 4706, a carbinol analogue).

SEARLE EXAMPLE 14

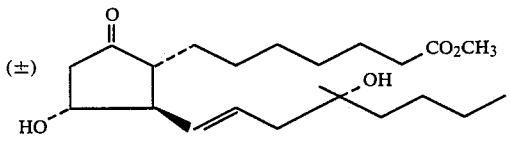

Racemic methyl 7-[3(R)-hydroxy-2β-(4(RS)-4-hydroxy-4-methyltrans-1-octenyl)-5-oxocyclopentane]-1α-heptanoate (the methyl ester analogous to presently claimed TR 4698, a carbinol analogue).

Searle generally discloses that the acids and esters disclosed and claimed display an ability to ". . . inhibit the gastric secretion stimulated by secretogogues such as histamine and pentagastrin while . . . lacking the potent undesirable side-effects displayed by related substances. In addition, these compounds are inhibitors of blood platelet aggregation and, moreover, display anti-fertility and bronchodilating properties." No biological data relating to the activity of any compounds disclosed and/or claimed by Searle is presented.

Searle also discloses compounds having a methylene group adjacent to C-16 and a cycloalkyl group attached thereto.

SEARLE EXAMPLE 22

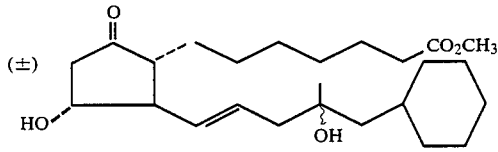

Methyl 7-[3(R)-hydroxy-2β-(4(RS)-4-cyclohexylmethyl)-4-hydroxy-4-methyl-1-trans-1-butenyl)-5-oxocyclopentane]-1α-heptanoate.

SEARLE EXAMPLE 43

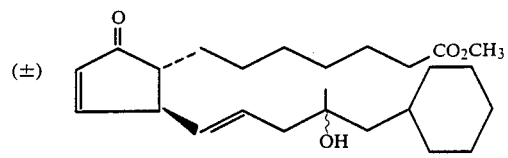

Racemic methyl 7-[2β-(4(RS)-4-cyclohexylmethyl-4-methyl-4-hydroxy-trans-1-butenyl)-5-oxocyclopent-3-ene]-1α-heptanoate.

The two cycloalkyl compounds disclosed by Searle are both esters. In addition, at least one methylene group separates the cycloalkyl moiety from the C-16 position.

As disclosed in detail hereinafter, applicants comparative biological testing of the alkyl-substituted ester prostaglandin analogues disclosed by Searle with applicants alkyl-substituted carbinols indicates that the alkyl-substituted carbinols exhibit a significant reduction in undesirable side-effects.

B. Other prior art relevant to the claimed carbinol 16-hydroxy prostaglandin analogues is published Netherlands application No. 73–10776, U.S. application Ser. No. 274,769, assigned by Lederle to American Cyanamid Company, (hereafter referred to as "Lederle". Lederle discloses acids and esters of 16-hydroxy prostaglandin analogues. The compounds of Lederle are represented by the following formula:

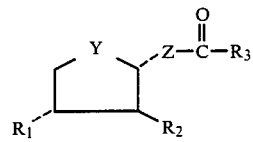

wherein $R_3$ is hydroxy or alkoxy and $R_2$ can be —C≡C—$CH_2$—R″ where R″ is a straight chain alkyl having from 2 to 10 carbon atoms substituted with an hydroxy triphenylmethoxy group or a straight chain alkyl having 2 to 6 carbon atoms and one branched group of 1 to 3 carbon atoms. Numerous examples of 16-hydroxy acid and ester prostaglandin analogues are disclosed.

According to Lederle, the esters and acids ". . . have potential utility as hypotensive agents, anti-ulcer agents, agents for the treatment of gastric hypersecretion and gastric erosion, agents to provide protection against the ulcerogenic and other gastric difficulties associated with the use of various non-sterodial antiinflammatory agents, bronchodilators, antimicrobial agents, anticonvulsants, abortifacients, agents for the induction of labor, agents for the induction of menses, fertility-controlling agents for the induction of menses, fertility-controlling agents, central nervous system regulatory agents, salt and waterretention regulatory agents, diuretics, fat metabolic regulatory agents and as serum-cholesterol lowering agents.

Biological data is presented for only six compounds of the numerous acids and esters disclosed. Anti-ulcer, gastric-antisecretory and bronchodilator properties are given for two 16-hydroxy prostaglandin analogues (pp. 22–25): 9-oxo-16-hydroxyprostanoic acid and 9-oxo-16-hydroxy-13-trans-prostenoic acid.

In summary, the two published Netherland Patent Applications discussed above disclose only prostaglandin analogues which are acids and esters. Of these analogues, only alkyl moieties and cycloalkyl moieties are disclosed. In the latter class of compounds, the cycloalkyl is separated from the C-16 position by interposition of at least one methylene group. The applications do not suggest that the claimed alkyl-substituted carbinols and the claimed cyclic and bicyclic carbinols and esters of the present invention would possess the unexpected separation of biological activity herein demonstrated.

SUMMARY OF THE INVENTION

The instant invention includes $C_{16}$-hydroxy carbinol analogues of:

(a) prostaglandin E analogues having the structural formula:

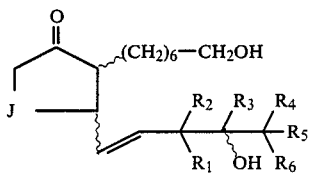

IV wherein:
- J is selected from the group consisting of R-hydroxymethylene and S-hydroxymethylene;
- $R_1$ is hydrogen;
- $R_2$ is hydrogen or together with $R_4$ is a methylene chain of 2 to 3 carbon atoms such that a cycloalkyl of 5 to 6 carbon atoms inclusive is formed;
- $R_3$ is selected from the group consisting of hydrogen or methyl, or together with $R_4$ is a methylene or a lower alkylated methylene chain of 2 to 5 carbon atoms such that a cycloalkyl or a lower alkylated cycloalkyl of 4 to 7 carbon atoms inclusive is formed, or together with $R_4$ is a bicycloalkyl or bicycloalkenyl moiety having the formula:

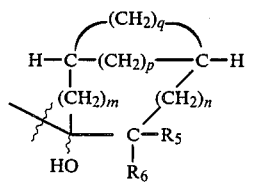

such that a bicycloalkyl or bicycloalkenyl compound is formed, wherein m and n are integers having a value of from 0 to 3, p is an integer having a value of from 0 to 4 and q is an integer having a value of from 1 to 4 and wherein the double bond of such bicycloalkenyl is in the m, n, p, or q bridge;
- $R_4$ is hydrogen or methyl or together with $R_2$ or $R_3$ forms a cycloalkyl, bicycloalkyl or bicycloalkenyl as defined above, or together with $R_5$ is a methylene chain of 3 to 5 carbon atoms such that a cycloalkyl of 4 to 6 carbon atoms inclusive is formed;
- $R_5$ is selected from the group consisting of hydrogen, straight-chain alkyl having from 1 to 3 carbon atoms or together with $R_4$ forms a cycloalkyl as defined above; and
- $R_6$ is selected from the group consisting of hydrogen or straight-chain alkyl having from 1 to 3 carbon atoms.

Included in this $C_{16}$-hydroxy carbinol genus are the following subgenera of prostaglandins;

(b) $E_1$ wherein $R_1$ and $R_2$ are hydrogen, $R_3$, $R_4$, $R_5$ and $R_6$ are selected from the group consisting of hydrogen and straight-chain loweralkyl having from 1 to 3 carbon atoms, having the structural formula IVb:

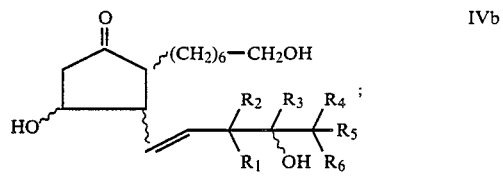

IVb (c) $E_1$ wherein $R_2$ and $R_4$ are closed to form a cycloalkyl having from 5 to 6 carbon atoms inclusive;

(d) $E_1$ wherein $R_2$ is hydrogen and $R_3$ and $R_4$ are closed to form a cycloalkyl or a lower alkylated cycloalkyl having from 4 to 7 carbon atoms inclusive;

(e) $E_1$ wherein $R_2$ is hydrogen and $R_3$ and $R_4$ are closed to form a bicycloalkyl or bicycloalkenyl;

(f) a therapeutic method for inhibiting gastric secretion in an individual for whom such therapy is indicated, comprising: administering to the individual an effective gastric inhibiting amount of a compound having the structural formula V:

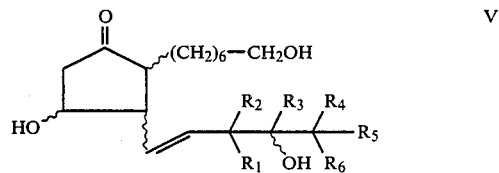

V wherein:
- $R_1$ is hydrogen;
- $R_2$ is hydrogen or together with $R_4$ is a methylene chain of 2 carbon atoms such that a cycloalkyl of 5 carbon atoms inclusive is formed;
- $R_3$ is hydrogen or methyl, or together with $R_4$ is a methylene or a lower alkylated methylene chain of 2 carbon atoms, to form a lower alkylated-substituted cycloalkyl of 4 carbon atoms inclusive, or together with $R_4$ is a bicycloalkyl moiety having the formula:

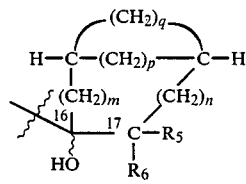

such that a bicycloalkyl compound is formed, wherein m and n are integers having a value of 0, p is an integer having a value of 1 and q is an integer having a value of 2;
- $R_4$ is hydrogen or methyl, or together with $R_2$ or $R_3$ forms a cycloalkyl, bicycloalkyl or bicycloalkenyl as defined above, with the proviso that when $R_5$ is methyl, $R_4$ is hydrogen;
- $R_5$ is hydrogen or methyl; and
- $R_6$ is hydrogen or a straight-chain alkyl having 3 carbon atoms.

(g) a therapeutic method for producing bronchodilation in an individual for whom such therapy is indicated, comprising: administering to the individual an effective bronchodilating amount of a compound having the structural formula V:

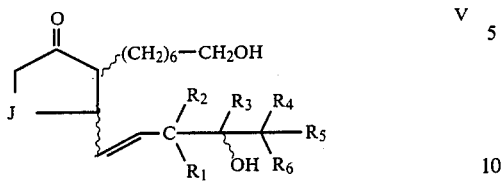

wherein:
J is selected from the group consisting of R-hydroxymethylene and S-hydroxymethylene;
$R_1$ and $R_2$ are hydrogen;
$R_3$ is selected from the group consisting of hydrogen and methyl, or together with $R_4$ is a methylene or a lower alkylated methylene chain of 2 to 5 carbon atoms such that a cycloalkyl or a lower alkylated cycloalkyl of 4 to 7 carbon atoms inclusive is formed, or together with $R_4$ is a bicycloalkyl or bicycloalkenyl moiety having the formula:

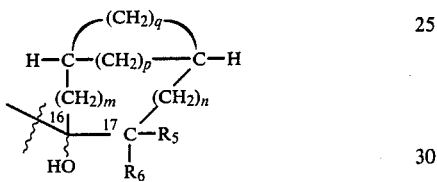

such that a bicycloalkyl or bicycloalkenyl compound is formed, wherein m and n are integers having a value of from 0 to 3, p is an integer having a value of from 1 to 4 and q is an integer having a value of from 1 to 3 and wherein the double bond of such bicycloalkenyl is in the m, n, p or q bridge;
$R_4$ together with $R_3$ forms a cycloalkyl or a lower alkylated cycloalkyl, bicycloalkyl or bicycloalkenyl as defined above, or together with $R_5$ is a methylene chain of 3 to 5 carbon atoms such that a cycloalkyl of 4 to 6 carbon atoms inclusive is formed;
$R_5$ is selected from the group consisting of hydrogen, straight-chain alkyl having from 1 to 3 carbon atoms or together with $R_4$ forms a cycloalkyl as defined above; and
$R_6$ is selected from the group consisting of hydrogen or straight-chain alkyl having from 1 to 3 carbon atoms.

(h) prostaglandin E analogues having the structural formula VI:

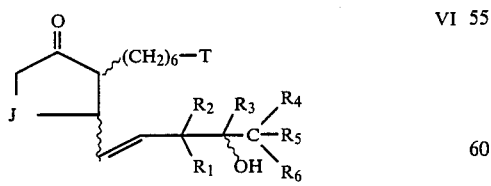

wherein:
J is selected from the group consisting of R-hydroxymethylene and S-hydroxymethylene;
T is alkloxycarbonyl having from 1 to 2 carbon atoms inclusive in the alkyl group;
$R_1$ is hydrogen;

$R_2$ is hydrogen or together with $R_4$ is a methylene chain of 2 to 3 carbon atoms such that a cycloalkyl of 5 to 6 carbon atoms inclusive is formed;
$R_3$ is hydrogen or together with $R_4$ is a methylene or a lower alkylated methylene chain of 3 to 5 carbon atoms such that a cycloalkyl of 5 to 7 carbon atoms inclusive is formed, or together with $R_4$ is a bicycloalkyl or bicycloalkenyl moiety having the formula:

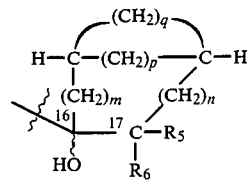

such that a bicycloalkyl or bicycloalkenyl compound is formed, wherein m and n are integers having a value of from 0 to 3, p is an integer having a value of from 0 to 4 and q is an integer having a value of from 1 to 3 and wherein the double bond of such bicycloalkenyl is in the m, n, p or q bridge;
$R_4$ together with $R_5$ is a methylene chain of 3 to 5 carbon atoms such that a cycloalkyl of 4 to 6 carbon atoms inclusive is formed or together with $R_2$ or $R_3$ forms a cycloalkyl, bicycloalkyl or bicycloalkenyl as defined above; and
$R_6$ is hydrogen or a straight-chain alkyl of 1 to 3 carbon atoms.

Included in this $C_{16}$-hydroxy alkoxy genus are the following subgenera of prostaglandins;
(i) $E_1$ wherein $R_1$ is hydrogen and $R_2$ and $R_4$ are closed to form a cycloalkyl having from 5 to 6 carbon atoms inclusive;
(j) $E_1$ wherein $R_1$ and $R_2$ are hydrogen and $R_3$ and $R_4$ are closed to form a bicycloalkyl or bicycloalkenyl;
(k) $E_1$ wherein $R_1$ is hydrogen and $R_3$ and $R_4$ are closed to form a cycloalkyl of 5 to 6 carbon atoms inclusive;
(l) $E_1$ wherein $R_1$ is hydrogen and $R_4$ and $R_5$ are closed to form a cycloalkyl of 4 to 5 carbon atoms inclusive;
(m) a therapeutic method for producing bronchodilation in an individual for whom such therapy is indicated, comprising: administering to the individual an effective bronchodilating amount of a compound having the structural formula VII:

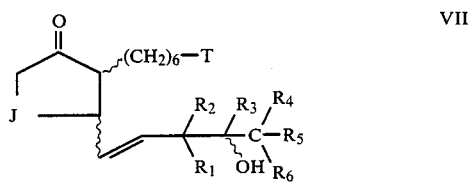

wherein:
J is selected from the group consisting of R-hydroxymethylene and S-hydroxymethylene;
T is alkoxycarbonyl having from 1 to 2 carbon atoms inclusive in the alkyl group;
$R_1$ is hydrogen;
$R_2$ is hydrogen or together with $R_4$ is a methylene chain of 3 carbon atoms such that cycloalkyl of 6 carbons atoms inclusive is formed;

$R_3$ is hydrogen or together with $R_4$ is a methylene or a lower alkylated methylene chain of 4 carbon atoms such that a cycloalkyl of 6 carbon atoms inclusive is formed, or together with $R_4$ is a bicycloalkyl or bicycloalkenyl moiety having the formula:

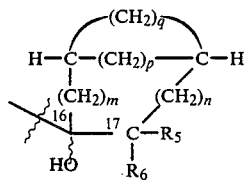

such that a bicycloalkyl of bicycloalkenyl compound is formed, wherein m and n are integers having a value of from 0 to 3, p is an integer having a value of from 0 to 4 and q is an integer having a value of from 1 to 4, and wherein the double bond of such bicycloalkenyl is in the m, n, p or q bridge;

$R_4$ is as defined above or together with $R_5$ is a methylene chain of 3 to 4 carbon atoms such that cycloalkyl of 4 to 5 carbon atoms inclusive is formed; and $R_6$ is H or a straight-chain alkyl of 1 to 3 carbon atoms;

(n) a therapeutic method for inhibiting gastric secretion in an individual for whom such therapy is indicated, comprising: administering to the individual an effective gastric inhibiting amount of a compound which can be methyl, $11\alpha$, 16RS-dihydroxy-16, 20-methano-9-oxoprost-13E-en-1-oate; methyl $11\alpha$, 16RS-dihydroxy-16, 18-methano-17, 20-methano-9-oxoprosta-13E, 19-dien-1-oate; methyl $11\alpha$ 16RS-dihydroxy-16, 18-methano-17, 20-methano-9-oxoprost-13E-en-1-oate or methyl $11\alpha$, 16RS-dihydroxy-16, 20-methano-17, 20-methano-9-oxoprost-13E-en-1-oate;

(o) organolithiocuprates having the formula:

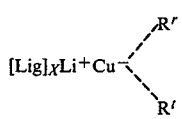

wherein Lig represents a solubilizing ligand. Generally Lig is a tri-(di-alkylamino) phosphine of 6–12 carbon atoms, trialkylphosphine having 3–12 carbon atoms, diarylphosphine, dialkylsulfide having 4–8 carbon atoms, arylsulfide, or di-(trialkylsilyl) amino having 6–12 carbon atoms. Specifically Lig can be a tri-(dimethylamino)phosphine, tri-(n-butyl)phosphine, diphenylphosphine, diisopropylsulfide, dibutylsulfide, phenylsulfide, or di-(trimethylsilyl)amino group.

$R^r$ is iodide, thiophenylate, alkyn-1-yl having 3 to 8 carbon atoms or $R^t$;

$R^t$ is a radical having the formula:

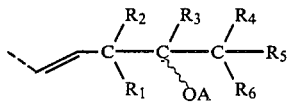

A is an acid-labile hydroxyl-protecting group, generally a tetrahydropyran-2-yl, trialkylsilyl, triarylsilyl, alkoxyalkyl having 2–6 carbon atoms, or a triarylmethyl group; and specifically is tetrahydropyran-2-yl, dimethyl(t-butyl)silyl, dimethylisopropylsilyl, trimethylsilyl, 1-ethoxyethyl, ethoxymethyl, 1-methoxyethyl, methoxymethyl, 2-ethoxyprop-2-yl, 2-methoxyprop-2-yl; or triphenylmethyl; wherein $R_2$ and $R_4$; $R_3$ and $R_4$ and $R_4$ and $R_5$ form a cycloalkyl as defined hereinbefore or $R_3$ and $R_4$ form a bicycloalkyl or bicycloalkenyl as defined hereinbefore; and $R_6$ is as defined hereinbefore; and X is an integer of the set 1 to 2.

(p) methods of preparing organolithiocuprates having the formula VII:

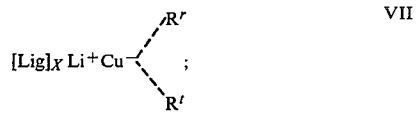

(q) a method of synthesizing a prostaglandin analogue having the structural formula VIII:

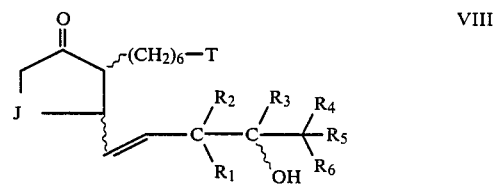

wherein T is $CH_2OH$,

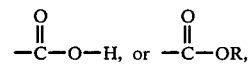

wherein R is a lower alkyl of 1 to 3 carbon atoms, by reacting an organolithiocuprate having the formula VII with a substituted 2-cyclopenten-1-one having the structural formula IX:

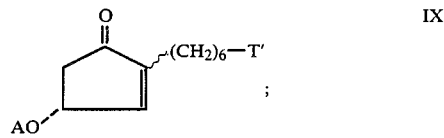

wherein T' is $-CH_2OA$ or

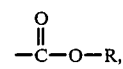

to form an intermediate having the structural formula X:

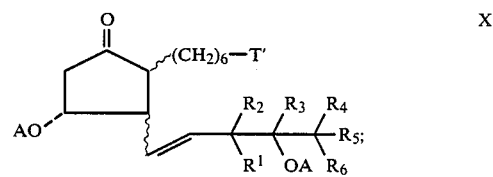

and hydrolyzing X with a weak acid to obtain the prostaglandin;

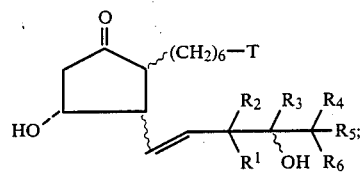

wherein T is CH$_2$OH, $$\underset{\parallel}{\text{O}} \quad \underset{\parallel}{\text{O}}$$
$$-\text{C}-\text{OH, or } -\text{C}-\text{OR}.$$

(r) iodovinyl alcohols having the structural formula VIII:

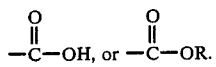

wherein R$_2$ and R$_4$, R$_3$ and R$_4$, or R$_4$ and R$_5$ form a cyloalkyl as defined hereinbefore or R$_3$ and R$_4$ form a bicycloalkyl or bicycloalkenyl as defined hereinbefore;

(s) methods of preparing iodovinyl alcohols having the structural formula VIII:

(t) protected-iodovinyl alcohols having the structural formula IX:

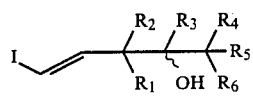

and (u) methods of preparing protected-iodovinyl alcohols having the structural formula IX.

DETAILED DESCRIPTION OF THE INVENTION

The compounds of the present invention, formula IV and VI, are prepared via the 1,4-conjugate addition of a 2-cyclopenten-1-one and an organolithiocuprate as reported by Sih, et. al., (J. Amer. Chem. Soc., 97: 857 and 865 [1975] and reference cited therein). The reaction proceeds in a variety of inert solvent systems of which ether, tetrahydrofuran, hexane, pentane or toluene are representative. The inert atmosphere can be provided by the use of argon or nitrogen. The prostaglandin analogues of formula IV and VI are prepared according to the reaction sequence depicted in Table A, described hereinafter.

TABLE A

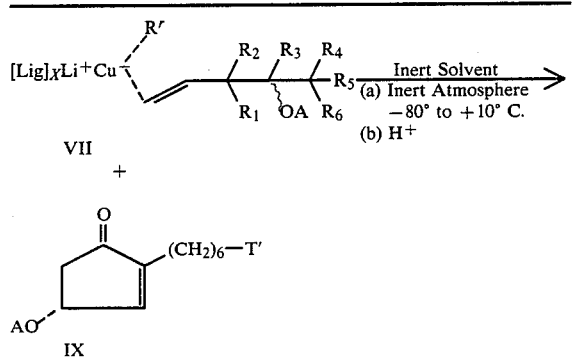

TABLE A-continued

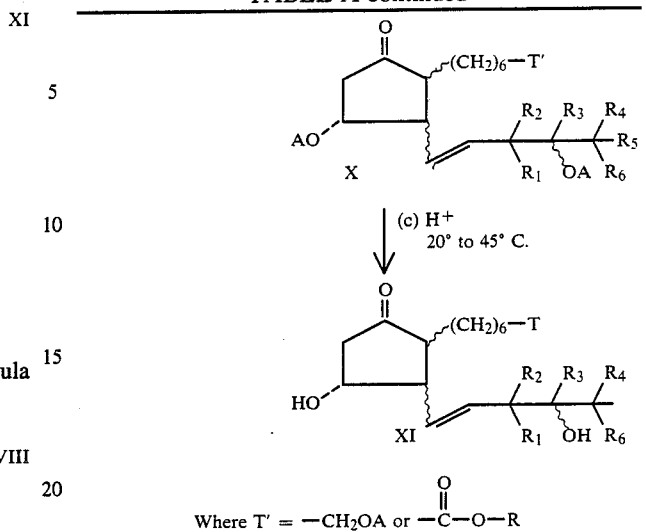

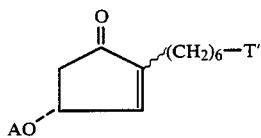

Where T′ = —CH$_2$OA or $-\underset{\parallel}{\overset{\text{O}}{\text{C}}}-\text{O}-\text{R}$ The reaction of the appropriate substituted 2-cyclopenten-1-one having the structural formula IX:

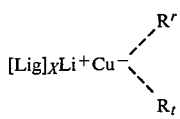

with the organolithiocuprate of formula VII:

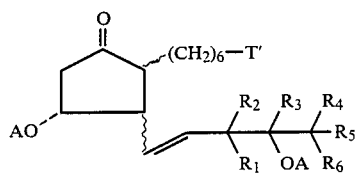

in an inert solvent, under an inert atmosphere at a temperature of from −80° to +10° for about 0.25 to three hours provides the intermediate having the structural formula X:

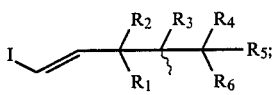

Hydrolysis of the intermediate X provides compound XI. Chemical hydrolysis can be accomplished by treatment with a weakly-acidic water mixture, e.g., acetic acid-water (65:35VV) with 10 percent tetrahydrofuran, at a temperature of about 20° to 45° C. for about 0.5 to 48 hours.

All compounds of this invention can be isolated from reaction mixtures and purified by well-known organic chemistry procedures. For example, the compounds can be isolated by dilution of the reaction mixture with water, extraction with a water-immiscible solvent such as benzene, cyclohexane, ether, ethyl acetate, methylene chloride, toluene and the like; chromatography; distillation or a combination of these procedures. Purification of these compounds can be accomplished by methods which are well-known in the art for the purification of prostaglandins, lipids, fatty acids, and fatty esters. Such methods as reverse phase partition chromatography; counter-current distribution; adsorption chromatography on acid washed magnesium silicate, neutral or acid washed silica gel, alumina or silicic acid; preparative paper chromatography; preparative thin layer chromatography; high pressure liquid-liquid chromatography; gas-liquid chromatography; and combinations thereof can be used to purify the compounds produced by the processes of this invention.

NMR spectra were determined in $CDCl_3$ and infrared (ir) spectra in $CHCl_3$ unless otherwise noted. Analytical thin layer chromatography was performed on 0.2 mm Silica Gel 60 F254 plates and preparative thin-layer chromatography was performed using 2.0 mm Silica Gel 60 F254 plates. "System II" is defined as the organic layer from a mixture of ethyl acetate, acetic acid, isooctane, and water in a ratio of 11:2:5:10. Spots were visualized under uv light and/or by ceric sulfate spray reagent [See K. Schreiber, et al., *J. Chromatography*, 12, 63 (1962)]. Column chromatographic separations were performed on 85:15 silicic acid-diatomaceous earth, such as Celite, or silica gel 60 using a benzene-ethyl acetate or hexane-ethyl acetate gradient elution unless otherwise specified. Mass spectra were determined by WARF, Inc., Madison, Wis., or Morgan Schaffer, Inc., Montreal, Canada.

A. Preparation of Substituted 2-Cyclopenten-1-one

When T' of substituted 2-cyclopenten-1-one IX is

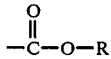

the substituted 2-cyclopenten-1-one is prepared as described by Sih et al., *J. Amer. Chem. Soc.*, 97, 865 (1975).

When T' is $-CH_2OA$, the substituted 2-cyclopenten-1-one is the natural "left-hand piece" described in *Tetrahedron Letters*, 2063 (1977) synthesized as outlined in Table B and summarized below.

Assymmetric, microbiological reduction of an appropriate 2-(ω-hydroxyalkyl)-cyclopentane-1,3,4-trione XV provides the corresponding 2-(ω-hydroxyalkyl)-4R-hydroxy-cyclopentan-1,3-dione XVI (Step A, Table B). The conversion of XV to XVI follows the procedures disclosed in U.S. Pat. No. 3,773,622 and utilizes microorganisms of the orders Endomycetales, Moliliales, and Eurotiliales in general and species *Dipodascus uninucleatus* and *Dipodascus albidus* in particular. Such microorganisms are in the public domain and can be obtained from depositories (American Tissue Type Collection [Bethesda, Md.] or the National Regional Research Laboratory, U.S.D.A., [Peoria, Ill.]). The advantage of microbiological reduction to the $C_4$ carbonyl group of XV is that it provides the chirality of the hydroxyl group requisite for analogues of $PGE_1$. Chemical reduction on the other hand provides a mixture of 2-(ω-hydroxyalkyl)-4RS-hydroxy-cyclopentane-1,3-diones.

Acylation or alkylation of XVI under alkaline conditions at a temperature of from $-25°$ C. to $100°$ C. (step B, Table B) gives a mixture of corresponding enol isomers, XVII and

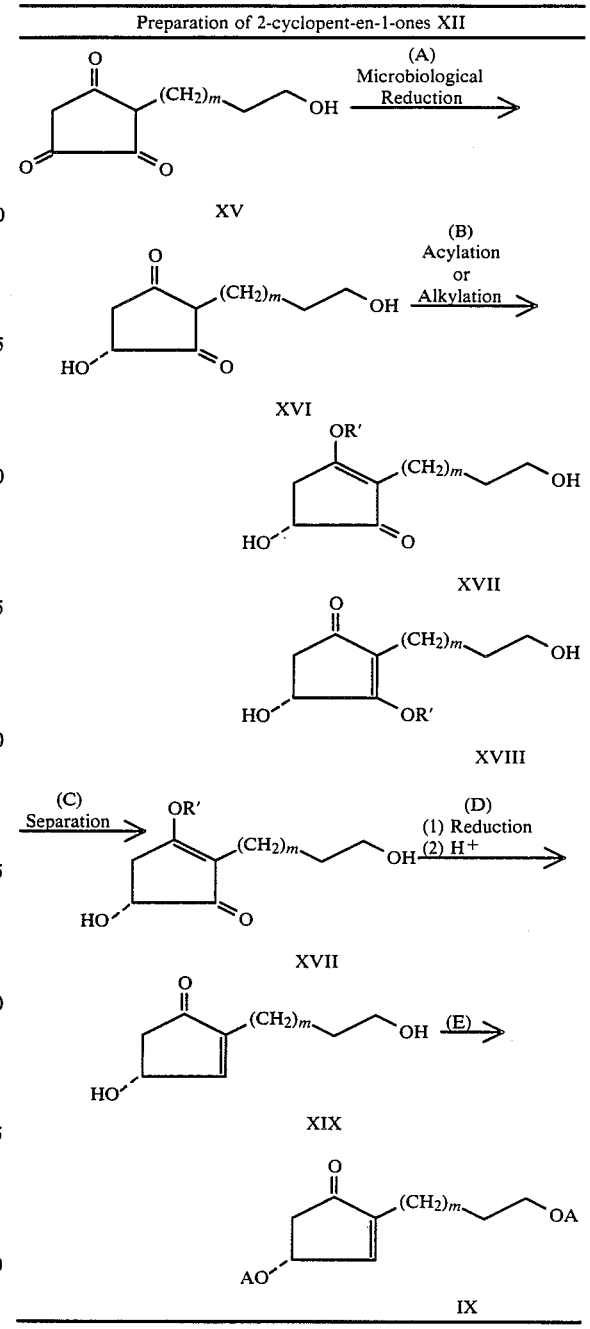

XVIII. Acylating agents useful in that step are benzoyl chloride, mesitylenesulfonyl chloride, pivaloyl chloride, and acetyl chloride (1 equivalent); alkylating agents include 2-iodopropane, 1-iodopropane, 1-iodo-2-methylpropane, and 1-iodo-3-methylbutane. Symbol R' in each of formulas XVII and XVIII corresponds to the respective acyl or alkyl group of the reagent utilized: benzoyl, mesitylenesulfonyl, pivaloyl, acetyl, prop-1-yl, 1-prop-2-yl, 2-methylprop-1-yl, and 3-methyl-but-1-yl. Conditions for acylation or alkylation follow the teachings of the Sih reference (p. 866-867, and Table 1 on 867).

Separation of isomer XVII (step C, Table B), reduction with lithium aluminum hydride, lithium borohydride or sodium bis-(2-methoxyethoxy) aluminum hydride at a temperature of from −80° C. to +80° C. depending on the solvent utilized (step D1, Table B), and subsequent removal of the acyl or alkyl group under acidic conditions at a temperature of from 20° C. to 35° C. (step D2, Table B) yields the corresponding 2-(ω-hydroxylalkyl)-4R-hydroxy-2-cyclopenten-1-one, XIX. Conditions for those procedures again are disclosed in the Sih reference (p. 867).

Reaction of XIX with dihydropyran or an alkyl vinyl ether (methyl vinyl ether, ethyl vinyl ether, propyl vinyl ether) under acid-catalyzed conditions or with a trialkylsilyl chloride (trimethylsilyl chloride, t-butyldimethylsilyl chloride) or triphenylmethyl bromide under basic conditions and at room temperature (step E, Table B) provides a substituted 2-cyclopenten-1-one IX in which the hydroxyl groups are masked with a group A corresponding to the reagent utilized in the reaction.

The 2-(ω-hydroxylalkyl)-cyclopentane-1,3,4-triones XV are prepared from ketoalkanols having the formula

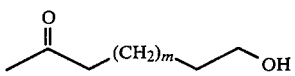  XX in which m is an integer of the set 1–8 or preferably of the subset 4–6. Condensation of an appropriate ketoalkanol XX with a dialkyloxalate in a suitable solvent and in the presence of an alkali metal base at reflux temperatures provides a 2-(ω-hydroxyalkyl)-5-(alkoxalyl)cyclopentane-1,3,4-trione of the formula,

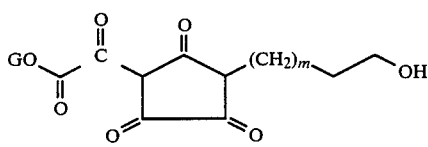  XXI wherein and subsequently elsewhere G is an alkyl group having 1–3 carbon atoms. The dialkyloxalate can be a dimethyl-, a diethyl-, or a dipropyl- oxalate of the general formula, $(GO_2G)_2$. Methanol, ethanol, dimethoxymethane, or benzene serve as suitable solvents for the reaction, and choice of solvent determines the reflux temperature. Alkali metal bases useful in the above reaction include, among others: sodium metal, sodium hydride, sodium methoxide, sodium ethoxide, sodium propoxide, potassium t-butoxide, or lithium hydride. Treatment of XXI with heat, acid catalysis, heavy-metal salts (barium hydroxide, manganese carbonate, calcium hydroxide, or thorium oxide), or dilute aqueous bases ($NaHCO_3$) removes the 5-alkoxalyl group to give the corresponding 2-(ω-hydroxyalkyl)-cyclopentane-1,3,4-trione XV.

Ketoalkanols XX are prepared by two routes of synthesis. One utilizes certain alkyl ketoalkanoates as starting materials, the other certain alkane dienes.

The first synthetic pathway is schematically presented in Table C and explained below.

Reaction of the appropriate compound XXII with a glycol of the formula,

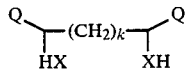

wherein and subsequently elsewhere, X is an oxygen or sulfur atoms, Q is a hydrogen atom or alkyl group having 1-2 carbon atoms and k is either 0 or 1, under acid catalysis under reflux (e.g., p-toluene sulfonic acid) yields the corresponding alkyl ketoalkanote-ketal, XXIV (step A, Table C). Reduction of XXIV with lithium aluminum hydride, lithium borohydride, diisobutylaluminum hydride, sodium bis-(2-methoxymethoxy)aluminum hydride, with an alkali-metal in liquid ammonia (Bouveault-Blanc reaction), or by hydrogenating under pressure with catalysis (Raney Nickel, Pd/C, Ag) gives the corresponding ketoalkanol ketal XXV. Hydrolysis of the ketal group under acidic conditons at room temperature affords XX. Starting materials XXII are commercially

TABLE C

Synthesis of Ketoalkanols XX From Alkyl Ketoalkanotes

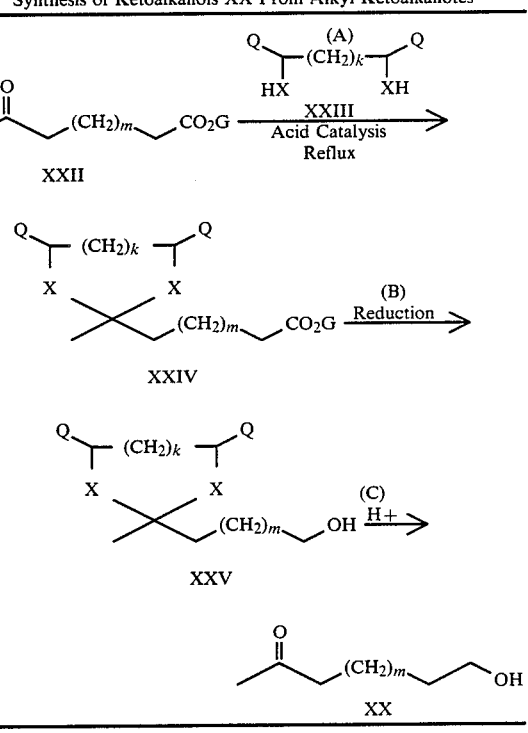

TABLE D

Synthesis of Keotalkanols XX from Alkane Dienes

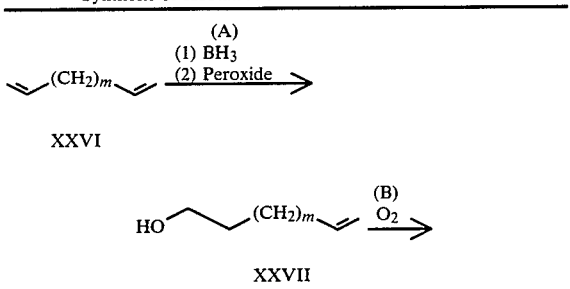

TABLE D-continued
Synthesis of Keotalkanols XX from Alkane Dienes

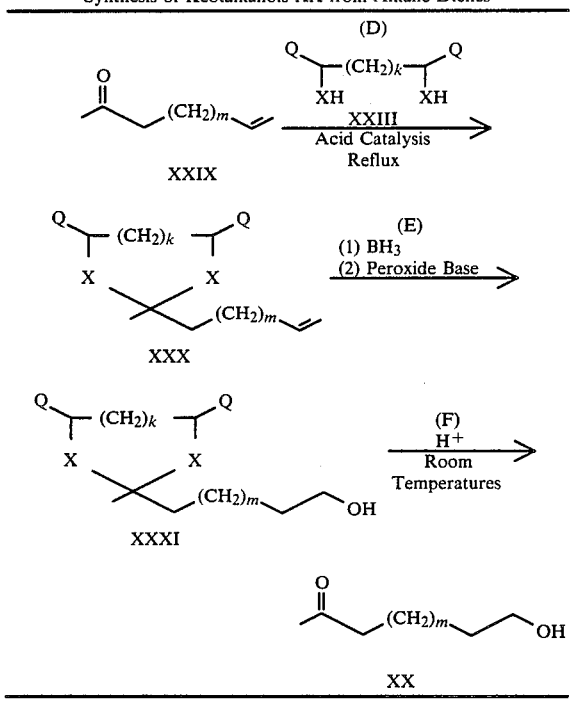

available or have been reported in the literature (*Agr. Biol. Chem.* [Japan], 33: 1079 [1969]). Compounds XXII are prepared by reacting methyl cadmium with appropriate ω-alkoxycarbonyl-alkanoyl chlorides, which in turn are prepared from appropriate dicarboxylic acids or alkane dienes (*J. Chem. Soc.*, 718 [1937]); (*J. Am. Chem. Soc.*, 68: 832 [1946]). Compounds XXI include 1,2-ethandiol, 1,2-propandiol, 1,3-propandiol, 1,3-butandiol, 2,3-butandiol, 2,4-pentandiol, and 1,2-ethanedithiol.

Table D provides an outline of a second method of synthesizing ketoalkanols XX.

Starting materials for the synthesis are alkane dienes XXVI such as 1,4-pentadiene, 1,5-hexadiene, 1,6-heptadiene, 1,7-octadiene, 1,8-nonadiene, 1,9-decadiene, 1,10-undecadiene, 1,11-dodecadiene. Such dienes are commercially available or are prepared from corresponding dicarboxylic acids.

Reaction of XXVI with borane (less than 1 equivalent) in an inert solvent followed by treatment with a peroxide ($H_2O_2$ or acetic peroxide) in the presence of base and at a temperature of from −25° C. to +25° C. yields a corresponding alkenol XXVII (step A, Table D).

Oxidation of XXVII by known methods provides the alkenoic acid XXVII (step B, Table D). Any oxidizing means can be used in that step: Jones reagent (*J. Chem. Soc.*, 39 [1946]); silver(II)oxide; oxygen with platinum catalyst; t-butyl chromate. Conditions of reaction will depend upon the selected means.

Reaction of XXVIII with methyllithium in an aprotic solvent at a temperature of from about −25° C. to +60° C. provides the ketoalkene XXIX (step C, Table D). Alternately, XXVIII is converted to an alkenoyl halide. The alkenoyl halide is then reacted with methylmagnesium chloride, dimethyl cadium or dimethyl zinc to give XXIX or is reacted with the magnesium salt of dialkyl-malonate (dimethyl, diethyl, or dipropyl malonate), hydrolyzed, and then decarboxylated to yield XXIX.

The carbonyl function of XXIX is protected by reacting the compound with a glycol XXIII (previously described) under acidic conditions and reflux to obtain the ketoalkene ketal, XXX (step D, Table D).

Reaction of XXX with borane and subsequently with peroxide in the presence of base at a temperature of from −25° C. to +25° C. provides the ketoalkanol ketal, XXXI (step E, Table D). Hydrolysis of the ketal to the corresponding ketoalkanol XX is performed under acidic conditions and at room temperature (step F, Table D).

B. Preparation of Organolithiocuprates

The preparation of various organolithiocuprates used in the present invention is depicted in Table E below and described in detail following Table E.

The organolithiocuprate utilized in the reaction is prepared in solution prior to reaction with the 2-cyclopenten-1-one, and is represented by formula VII;

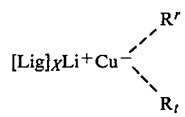

The organolithiocuprate is prepared from the iodovinyl alcohol of structure XXXVII. In turn, the iodovinyl alcohol of structure XXXVII is prepared from the appropriate ketone or aldehyde through an acetylenic alcohol intermediate. As depicted in Table E, the acetylenic alcohol intermediate can be prepared by alternate pathways. The acetylenic alcohol intermediate is then converted to the corresponding iodovinyl alcohol. The hydroxyl function of the iodovinyl alcohol is protected with an acid-labile hydroxy-protecting group. Alternately, the hydroxyl group of the acetylenic alcohol can be protected prior to conversion of the alcohol to the corresponding iodovinyl compound.

The hydroxy-protected iodovinyl alcohol is then lithiated with t-butyllithium and reacted with a solubilized Lig complex of a copper(I) compound such as (hexamethylphosphoroustriamide)₂copper(I)pentyne to yield the desired organolithiocuprate.

TABLE E

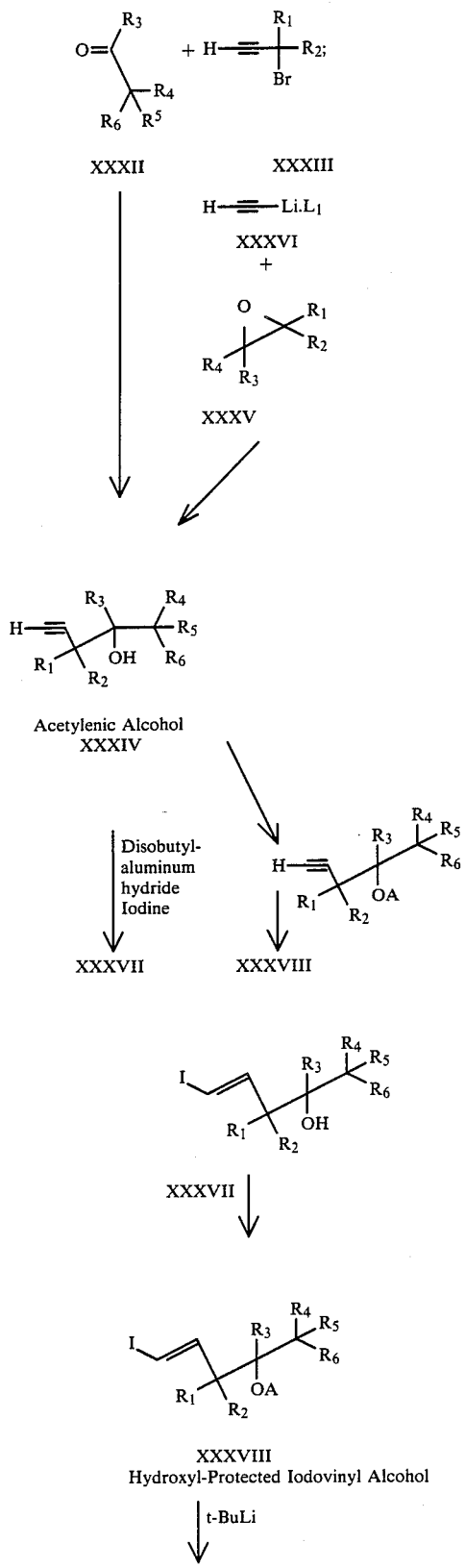

TABLE E-continued

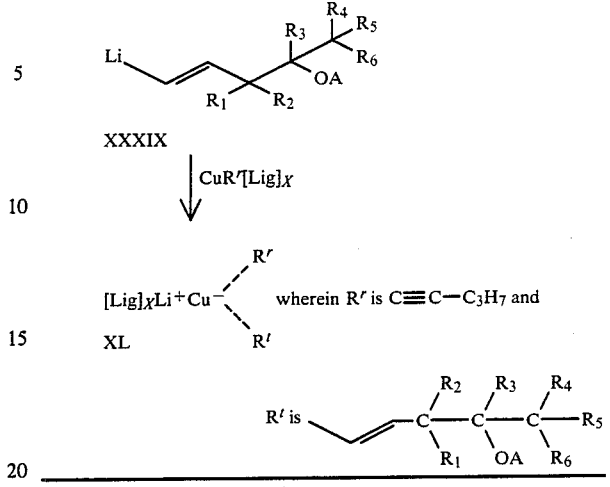

Preparation of Iidovinylalcohol and Organolithiocuprate

As shown in Table E, the appropriate ketone XXXII was reacted with the appropriate acetylenic bromide XXXIII in the presence of magnesium metal. The acetylenic alcohol XXXIV intermediate was recovered after refluxing the mixture. (See J. Amer. Chem. Soc., 93: 6967 [1971]).

Alternately, the acetylenic alcohol intermediate XXXIV can be prepared by reacting the appropriate alkene oxide XXXV with lithium acetylide ethylene diamine complex XXXVI in hexamethylphosphoramide. (See Bio. 89: 853 [1956]).

As shown in Table E, the acetylenic alcohol intermediate XXXIV can be converted into the corresponding iodovinylalcohol XXXVII by adding to the acetylenic alcohol diisobutylaluminum hydride in a solvent such as dry toluene followed by iodine in a solvent such as dry tetrahydrofuran (THF). (See J. Amer. Chem. Soc., 97: 857 [1975]). The hydroxyl-group of the iodovinyl alcohol XXXVII is then protected by masking the hydroxyl function with acid-catalyzed dihydropyran or ethyl vinyl ether or basic-catalyzed trialkylsilyl chloride or triphenylmethyl bromide to obtain the protected alcohol XXXVIII. (See J. F. W. McOmie, "Protective Groups in Organic Chemistry", Plenum Press, New York, 1973, p. 95f).

Alternately, the hydroxyl function of the acetylenic alcohol can be protected as described above, and the protected alcohol converted into the corresponding protected iodovinyl alcohol as taught in J. Amer. Chem. Soc., 94: 7827 (1972) and 83: 1241 (1961).

The iodovinyl alcohols have utility as intermediates in producing the prostaglandin analogues of the present invention.

The protected iodovinyl alcohol is lithiated with metallic lithium or an alkyllithium (n-butyl, sec-butyl or tert-butyl) to form the lithio complex XXXIX. The lithio complex XXXIX is reacted with the solubilized copper(I) species, for example, the hexamethylphosphorous trimide complex of copper n-propyl acetylide, to produce the desired organolithiocuprate XL. Specifically, (hexamethylphosphorous triamide)$_2$-copper(I)-pentyne is disclosed in J. Amer. Chem. Soc., 94: 7211 (1972) and in J. Org. Chem., 31: 4071 (1966). Tri-n-butylphosphine-copper-(I)iodide is described in *Inorg. Synth.,* 7: 9 (1963). Hexamethylphosphorous triamide-copper-(I)-iodide is taught in *Prostaglandins,* 7: 38 (1974). Preparation of phenylthio-copper is disclosed in *Synthesis,* 602 (1974). For a thorough review of organolithiocuprates and their utility in the synthesis of natural prostaglandins, see *J. Amer. Chem. Soc.,* 97: 857 and 865 (1975). The organolithiocuprate is reacted with the desired substituted 2-cyclopenten-1-one of formula IX as depicted in Table A.

The following Table F illustrates embodiments of the prostaglandin analogues of the present invention compiled by Example No. and Compound No. and identified by the Chemical Abstracts system of nomenclature.

TABLE F

| Example Number | Compound Number | Chemical Abstracts Nomenclature |
|---|---|---|
| 1 | TR 4698 | 16-methyl-1, 11α, 16RS—trihydroxyprost-13E—en-9-one |
| 2 | TR 4706 | 1, 11α, 16RS—trihydroxyprost-13E—en-9-one |
| 3a | TR 4752 | 1, 11α, 16R or S—trihydroxy-17-dimethylprost-13E—en-9-one |
| 3b | TR 4751 | 1, 11α, 16R or S—trihydroxy-17,17-dimethylprost-13E—en-9-one |
| 4 | TR 4749 | 1, 11α, 16RS—trihydroxy-17RS—methylprost-13E—en-9-one |
| 5a | TR 4848 | 15,20-Cyclo-1,11α,16S—trihydroxy-prost-13E—en-9-one |
| 5b | TR 4840 | 15,20-cyclo-1, 11α, 16R—trihydroxy-prost-13E—en-9-one |
| 6a | TR 4844 | 15, 19-cyclo-20-nor-1, 11α, 16R—trihydroxy-prost-13E—en-9-one |
| 6b | TR 4846 | 15, 19-cyclo-20-nor-1, 11α, 16S—trihydroxy-prost-13E—en-9-one |
| 7 | TR 4703 | 16, 20-methano-1, 11α, 16-trihydroxyprost-13E—en-9-one |
| 8 | TR 4753 | 20-nor-16, 19-cyclo-1, 11α, 16-trihydroxyprost-13E—en-9-one |
| 9 | TR 4851 | 16, 20-methano-18RS—methyl-1, 11α, 16RS—trihydroxyprost-13E—en-9-one |
| 10 | TR 4770 | 16, 18-methano-1, 11α, 16RS—trihydroxyprost-13E—en-9-one |
| 11 | TR 4803 | 16, 18-methano-17, 20-methano-1, 11α, 16RS—trihydroxyprosta-13E, 19-dien-9-one |
| 12a | TR 4804 | 16, 18-methano-17, 20-ethano-1, 11α, 16RS—trihydroxyprost-13E—en-9-one |
| 12b | TR 4806 | 16, 18-methano-17, 20-ethano-1, 16RS—dihydroxyprosta-10, 13E—dien-9-one |
| 13a | TR 4799 | 16, 18-methano-17, 20-methano-1, 11α, 16RS—trihydroxyprost-13E—en-9-one |
| 13b | TR 4805 | 16, 18-methano-17, 20-methano-1, 16RS—trihydroxyprosta-10, 13E—diene-9-one |
| 14 | TR 4903 | 16,20-methano-17,20-methano-1, 11α, 16RS—trihydroxyprost-13E—en-9-one |
| 15a | TR 4982 | 17, 20-methano-17-methyl-1, 11α, 16R and S—trihydroxyprost 13E—en-9-one |
| 15b | TR 4983 | 17, 20-methano-17-methyl-1, 11α, 16RS—trihydroxyprost-13E—en-9-one |
| 16a | TR 4984 | 17,17-Propano-1, 11α, 16R—trihydroxyprost-13E—en-9-one |
| 16b | TR 4985 | 17,17-Propano-1, 11α, 16S—trihydroxyprost-13E—en-9-one |

TABLE F-continued

| Example Number | Compound Number | Chemical Abstracts Nomenclature |
|---|---|---|
| Comp. Proc. A | TR 4704 | Methyl 11α, 16RS—dihydroxy-16-methyl-9-oxoprost-13E—oate |
| Comp. Proc. B | TR 4705 | Methyl 11α, 16RS—dihydroxy-9-oxoprost-13E—en-1-oate |
| Comp. Proc. C | TR 4836 | Methyl 11α, 16R and S—dihydroxy-17, 17-dimethyl-9-oxoprost-13E—en-1-oate |
| Comp. Proc. D | TR 4814 | Methyl 11α, 16RS—dihydroxy-17-methyl-9-oxoprost-13E—oate |
| 17a | TR 4838 | Methyl 15R, 19-cyclo-11α, 16-trans-dihydroxy-20-nor-9-oxoprost-13E—en-1-oate |
| 17b | TR 4839 | Methyl 15S, 19-cyclo-11α, 16-trans-dihydroxy-20-nor-9-oxoprost-13E—en-1-oate |
| 18a | TR 4767 | Methyl 15R, 20-cyclo-11α, 16-trans-dihydro-9-oxoprost-13E—en-1-oate |
| 18b | TR 4768 | Methyl 15S, 20-cyclo-11α, 16-trans-dihydro-9-oxoprost-13E—en-1-oate |
| 19 | TR 4717 | Methyl 11α, 16RS—dihydroxy-16, 20-methano-9-oxoprost-13E—en-1-oate |
| 20a | TR 4800 | Methyl 11α, 16RS—dihydroxy-16, 18-methano-17, 20-methano-9-oxoprosta-13E, 19-dien-1-oate |
| 20b | TR 4802 | Methyl 16RS—hydroxy-16, 18-methano-17, 20-methano-9-oxoprosta-10, 13E, 19-trien-1-oate |
| 21a | TR 4808 | Methyl 11α, 16RS—dihydroxy-17, 20-ethano-16, 18-methano-9-oxoprost-13E—en-1-oate |
| 21b | TR 4807 | Methyl 17, 20-ethano-16RS—hydroxy-16, 18-methano-9-oxoprosta-10, 13E—dien-1-oate |
| 22a | TR 4809 | Methyl 11α, 16RS—dihydroxy-16, 18-methano-17, 20-methano-9-oxoprost-13E—en-1-oate |
| 22b | TR 4801 | Methyl 16RS—hydroxy-16, 18-methano-17, 20-methano-9-oxoprosta-10, 13E—dien-1-oate |
| 23 | TR 4883 | Methyl 11α, 16RS—dihydroxy-16, 20-methano-17, 20-methano-9-oxoprost-13E—en-1-oate |
| 24a | TR 4978 | Methyl 11α, 16R and S—dihydroxy-17, 17-propano-9-oxoprost-13E—ene-1-oate |
| 24b | TR 4979 | Methyl 11α, 16RS—dihydroxy-9-oxo-17, 17-propanoprost-13E—en-1-oate |
| 25a | TR 4980 | Methyl 11α, 16R—dihydroxy-17, 20-methano-17-methyl-9-oxoprost-13E—en-1-oate |
| 25b | TR 4981 | Methyl 11α, 16S—dihydroxy-17, 2-methano-17-methyl-9-oxoprost-13E—en-1-oate |

DESCRIPTION OF THE PREFERRED EMBODIMENTS

Example 1

16-methyl-1,11α,16RS-trihydroxyprost-13E-en-9-one (TR4698)

The reaction pathway is shown below.

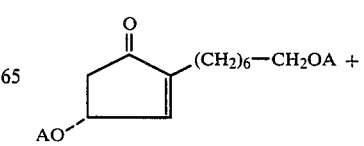

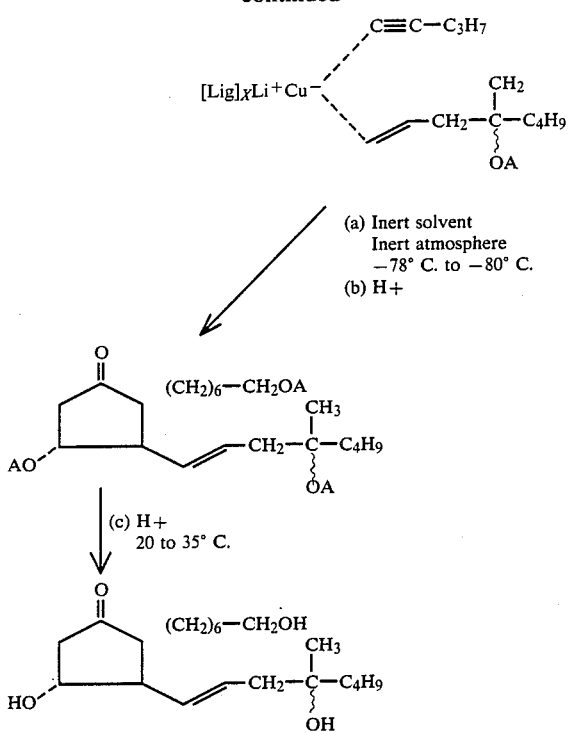

A. Preparation of Iodovinylalcohol [1-Iodo-4-methyloct-1E-en-4RS-ol]

A 12.2 g portion of magnesium turnings was heat dried under argon in a 500 ml flask fitted with an air stirrer, condensor and addition funnel. After cooling the flask, 60 ml of dry ether was added, followed by a small portion of a solution of 33.9 ml of propargyl bromide in 60 ml of dry ether followed by 50 mg of mercuric chloride. After spontaneous ether reflux indicated that the reaction had commenced, the remainder of the propargyl bromide solution was added dropwise to the mixture to maintain gentle reflux. After the addition was complete, the reaction mixture was stirred for an additional one-half hour. A solution of 25 g of 2-hexanone, commercially available, in 25 ml of dry ether was then added to the reaction mixture, again at a rate to maintain gentle reflux. A heated oil bath was then used to reflux the final mixture for another hour. The final mixture was then quenched by the addition of water, followed by 10 percent hydrochloric acid to dissolve solid salts. The phases were separated and the ether extract was washed with brine and saturated sodium bicarbonate solution. It was then dried over MgSO$_4$ and then distilled using a water pump to successively remove ether and a trace of 2-hexanone (bp ca 30°). A 22.4 g portion (64 percent) of the acetylenic alcohol intermediate, methyloct-1-yn-4RS-ol, bp 70°-76° (ca 20 mm) was recovered. Glc analysis of this product showed a 20 percent impurity thought to be 4-methylocta-1,2-dien-4RS-ol. The distilled 80 percent pure alcohol was used in successive experiments. The material had the following spectral characteristics: nmr (CDCl$_3$) δ 0.93 (3H, broad t, J=5 Hz), 1.0 to 1.7 (6H, m), 1.28 (3H, S), 1.82 (1H, s), 2.12 (1H, t, J=3 Hz) and 2.39 ppm (2H, d, J=3 Hz); ir (CHCl$_3$) 1120, 1380, 1460, 2120, (weak), 2870, 2930, 2960, 3300, 3200 to 3600 broad and 3590 cm$^{-1}$.

The 4-methyloct-1-yn-4RS-ol was converted to the corresponding iodovinylalcohol, 1-Iodo-4-methyloct-1E-en-4RS-ol as described below.

A solution of 30 ml (169 mmol) of diisobutylaluminum hydride in 75 ml of dry toluene was stirred under argon with ice water bath cooling as a second solution of 7.0 g (50 mmol) of the 4-methyloct-1-yn-4RS-ol, in 25 ml of dry toluene was added dropwise over a period of one hour. Stirring was then continued without cooling for one hour and then with oil bath warming (50°-60° C.) for three hours. The oil bath was then replaced with a dry ice-acetone (−78° C.) bath as a third solution of 42.8 g (169 mmol) of iodine in dry tetrahydrofuran to total 100 ml was added dropwise to the reaction mixture maintaining a stirring of the reaction mixture. The cooling bath was then removed and the reaction mixture was allowed to come to 20° slowly before it was quenched by being forced under a slight argon pressure through polyethylene tubing into a vigorously stirred mixture of ether and two percent aqueous sulfuric acid. The ether phase was removed and then washed successively with another portion of two percent sulfuric acid, brine, saturated aqueous sodium bicarbonate and brine. It was dried over Na$_2$SO$_4$ and evaporated under reduced pressure. The residue (10.3 g) was chromatographed on silica gel to yield 1.4 g of partially pure and 1.2 g of pure 1-Iodo-4-methyloct-1E-en-4RS-ol, along with several grams of highly contaminated material. The impure fractions were each distilled at 0.1 mm to yield a total of 2.35 g of recovered acetylenic alcohol (bp 50°-55° C.) and 2.55 g of reasonably pure iodovinylalcohol (bp 60°-65° C.). The total yield of pure iodovinylalcohol was thus 3.8 g; nmr (CDCl$_3$) δ 0.93 (3H, broad t, J=5 Hz), 1.18 (3H, s), 1.0-1.7 (6H, m), 2.20 (1H, s), 2.25 (2H, d, J=7 Hz), 6.20 (1H, d, J=15 Hz) and 6.73 ppm (1H, d of t, J=15, 7 Hz); ir (film) 750, 900, 940, 1140, 1380, 1465, 2870, 2930, 2960, and 3200-3600 cm$^{-1}$ (broad).

The conversion of the acetylenic alcohol can be carried out by replacing diisobutylaluminum hydride with disiamylborane; a base, for example an alkali metal hydroxide such as sodium or potassium hydroxide; a trialkylamine oxide such as trimethylamine oxide; and iodine.

B. Preparation of Organolithiocuprate from Iodovinylalcohol

(1) Preparation of 1Iodo-4-methyl-4RS-(tetrahydropyranyloxy)oct-1E-ene

The hydroxyl function of the iodovinylalcohol prepared as described above was protected as described below.

A solution of 0.806 g (3.00 mmol) of 1-iodo-4-methyloct-1E-en-4RS-ol, 0.34 ml (3.73 mmol) of dihydropyran and a 5 mg portion of toluenesulfonic acid in 1.5 ml of dry ether was stirred in a flask under argon. Tlc (CHCl$_3$, silica gel) analysis after one and one-half hours indicated that the reaction was not completed; an additional 0.2 ml portion of dihydropyran and about 5 mg of toluene-sulfonic acid were added, followed after another hour with another 0.5 ml portion of dihydropyran and toluenesulfonic acid. After a period of one and one-half hours, solid potassium carbonate was added to the reaction mixture. After stirring for several minutes the resultant mixture was washed with water. The washed solution was back extracted with ether three times. The combined extract was dried (Na$_2$SO$_4$) and evaporated in vacuo to yield 1.16 g of the title compound: nmr (CDCl$_3$) δ 0.95 (3H, m), 1.20 (3H, s), 1.0–1.8 (12H, m), 2.3 (2H, d, J=8 Hz), 3.3–4.2 (2H, m), 4.82 (1H, broad s), 6.12 (1H, d, J=14 Hz) and 6.73 ppm (1H, d of t, J=14, 7 Hz); ir (CHCl$_3$) 870, 950, 990, 1020, 1070, 1125, 1380, 1470, 1610, 2870 and 2930 cm$^{-1}$.

(2) Preparation of Organolithiocuprate from Protected Iodovinylalcohol

A solution of 1.06 g (3.00 mmol) of 1-iodo-4-methyl-4RS(tetrahydropyranyloxy)-oct-1E-ene, in 10 ml of dry ether was stirred in a flask under argon with −78° bath cooling as 5.5 ml (6.0 mmol) of a 1.18M solution of t-butyllithium in pentane was added dropwise via syringe. The resultant solution was stirred at −78° for two hours.

A second solution was prepared by stirring under argon a suspension of 0.392 g (3.00 mmol) of dry copper (I) pentyne in 5 ml of dry ether solubilized with 1.10 ml of hexamethylphosphorous triamide, until it became homogeneous. This second solution was then transferred via syringe to the above alkenyllithium reaction mixture as it was stirred with −78° bath cooling. The desired lithiocuprate reagent, an orange mixture, was stirred 15 minutes after addition was complete.

C. Substituted 2-Cyclopenten-1-one 4R-(tetrahydropyran-2-yloxy)-2-[7-(tetrahydropyran-2-yloxy)heptyl]-2-cyclopenten-1-one was prepared from the appropriate 2-(ω-hydroxyalkyl)-cyclopenten-1,3,4-trione as described in *Tetrahedron Letters*, 2063 (1977) and described in detail hereinbefore.

D. Prostaglandin Synthesis

The synthesis of the prostaglandin E$_1$ analogue was achieved as described below.

A solution of 0.785 g (2.06 mmol) of 4R-(tetrahydropyran-2-yloxy)2-[7-(tetrahydropyran-2-yloxy)heptyl]-cyclopent-2-enone, in 3 ml of dry ether was added dropwise to the lithiocuprate reaction mixture as stirring was continued at −78°. After addition was complete, the resultant orange mixture was stirred for 10 min. at −78° and then at −20° for three hours.

The reaction was quenched at −20° by the addition of sufficient two percent aqueous sulfuric acid to give an acidic aqueous phase after stirring. The resultant mixture was thoroughly shaken and then filtered through Celite. The filter pad was rinsed thoroughly with ether. The filtrate phases were separated and the organic phase was washed with brine and saturated aqueous sodium bicarbonate. It was then dried over MgSO$_4$ and evaporated in vacuo to yield 1.5 g of residue containing the tetrahydropyran-protected form of TR 4698.

This residue was dissolved in 20 ml of acetic acid-water-tetrahydrofuran (65:35:10) and left to stand under argon for 41.5 hours at room temperature and the resultant solution evaporated in vacuo to remove the solvent. The residue was dissolved in ethyl acetate and washed with saturated aqueous sodium bicarbonate. The wash solution was back extracted with ethyl acetate. The combined extract was dried over MgSO$_4$ and evaporated in vacuo to yield 1.29 g of a yellow residue. This residue was chromatographed on silicic acid-diatomaceous earth (85:15) using benzene-ethyl acetate gradient elution to yield 193.1 mg (26.5 percent) of the pure PGE$_1$ analogue along with less polar materials that appeared to contain the PGE$_1$ analogue, and as a side-product, and PGA analogue, both protected as tetrahydropyran-2-yl-ethers. These less polar materials were dissolved in another portion of acetic acid-water-tetrahydrofuran and left under argon for three days. The product was isolated as earlier described, and the resultant residue was purified by thin layer chromatography on silica gel (ether elution, 2 mm layer) to yield 23.5 mg of the PGA side-product designated as TR 4702. No attempt was made to recover the small amount of additional PGE$_1$ analogue which was also present. The spectral characteristics of TR 4698 and the side-product PGA were:

TR 4698 [α]$_D$−58.6° (c 1.0, CHCl$_3$); R$_f$ (system II) 0.29; nmr (CDCl$_3$) δ 0.93 (3H, m), 1.17 (3H, s), 1.0–2.7 (24H, m), 3.63 (5H, broad s over broad t, J=6.0 Hz), 4.20 (1H, q, J=7.0 Hz) and 5.64 ppm (2H, m); ir (CDCl$_3$) 895, 970, 1065, 1150, 1740, 2860, 2930, and 3200–3600 cm$^{-1}$; ms (70 eV) 336 (p—H$_2$O), 318 (p—2H$_2$O), 278, 264, 253, 235, 217, 193.

TR 4702 [α]$_D$+70.7° (c 1.17, CHCl$_3$); R$_f$(ether) 0.19; nmr (CDCl$_3$) δ 0.96 (3H, m), 1.20 (3H, s)., 1.0–2.5 (23H, m), 3.37 (1H, m), 3.73 (2H, m), 5.73 (2H, m), 6.30 (1H, m) and 7.67 ppm (1H, m); ir (CHCl$_3$) 900, 970, 1030, 1075, 1125, 1700, 2860, 2930, 3200–3600 and 3600 cm$^{-1}$; ms (70 eV) 321 (p—CH$_3$), 318 (p—H$_2$O), 279, 261, 236, 218.

Example 2

1,11α,16RS-trihydroxyprost-13E-en-9-one (TR 4706)

The method described in Example 1 was used to prepare TR 4706 by replacing the 2-hexanone with commericially available pentanal. The acetylenic alcohol intermediate, oct-1-yn-4RS-ol had the following spectral characteristics: nmr (CDCl$_3$) δ 0.93 (3H, broad t, J=5 Hz), 1.0 to 2.6 (10H, m) and 3.87 (1H, broad m); ir (CHCl$_3$) 925, 1210, 2420, 2850, 2920, 2960, 3010, 3300, 3200 to 3600 (broad) and 3590 cm$^{-1}$.

The 1-iodooct-1E-en-4RS-ol had the following spectral characteristics: nmr (CDCl$_3$) δ 0.93 (3H, broad t, J=6 Hz), 1.0–1.7 (6H, m), 1.87 (1H, s), 2.27 (2H, t, j=6 Hz), 3.77 (1H, broad m), 6.24 (1H, d, J=15 Hz) and 6.73 ppm (1H, d of t, J=15, 6 Hz); ir (CHCl$_3$) 900, 950, 1470, 2860, 2930, 2960, 3200–3600 (broad) and 3600 cm$^{-1}$.

The iodovinyl alcohol was protected to yield 1-iodo-4RS-(tetrahydropyranyloxy)oct-1E-ene having the following spectral characteristics: nmr (CDCl$_3$) δ 0.93 (3H, m), 1.0–2.8 (14H, m), 3.3–4.2 (3H, m), 4.84 (1H, broad s), 6.20 (1H, d, J=14 Hz) and 6.73 ppm (1H, d of d, J=14, 7 Hz).

The resulting PGE$_1$ analogue had the following spectral characteristics: [α]$_D$−56.4° (c 1.0 CHCl$_3$); R$_f$(system II) 0.30; nmr (CDCl$_3$) δ 0.98 (3H, m), 1.0–2.7 (24H, m); 3.75 (2H, broad t, J=6.0 Hz), 3.86 (3H, s), 4.2 (2H, m), and 5.73 ppm (2H, m); ir (CHCl$_3$) 900, 970, 1070, 1110, 1150, 1240, 1380, 1460, 1740, 2860, 2930, 3200–3600 and 3600 cm$^{-1}$; ms (70 eV) m/e 322 (p—H$_2$O), 304 (p—2H$_2$O), 254, 236.

Example 3

1,11α,16R-trihydroxy-17,17-dimethylprost-13E-en-9-one and
1,11α,16S-trihydroxy-17,17-dimethylprost-13E-en-9-one (TR4752 and TR 4751)

A solution of 2,2-dimethylpentanal was substituted for the 2-hexanone of Example 1. The 2,2-dimethylpentanal was produced from commercially available 2-methylpropionic acid as described below.

A 240 ml (285 mmol) portion of a solution of t-butyllithium in pentane (1.18M) was added dropwise to a solution of 42 ml (290 mmol) of diisopropylamine in 300 ml of dry tetrahydrofuran while it was stirred with −5° bath cooling under argon. A 12.7 ml (135 mmol) portion of 2-methylpropionic acid in 15 ml of dry tetrahydrofuran was then added dropwise to the reaction mixture. A 14.3 ml (140 mmol) portion of n-propyliodide was then added dropwise to the reaction mixture as stirring was continued with ice bath cooling. The resultant mixture was stirred two hours without cooling and then acidified by the slow addition of 10% hydrochloric acid. The resultant mixture was extracted several times with ether and the combined extracts were washed with brine, dried ($Na_2SO_4$) and evaporated in vacuo to yield 16.3 g of 2,2-dimethylpentanoic acid, having the following spectral characteristics: nmr ($CDCl_3$) δ 0.94 (3H, t, J=8.5 Hz), 1.20 (6H, s), 1.2–1.8 (4H, m) and 11.3 ppm (1H, broad s); ir ($CHCl_3$) 860, 945, 1185, 1240, 1290, 1310, 1370, 1410, 1480, 1700 and 2400–3400 $cm^{-1}$ (broad).

The 2,2-dimethylpentanoic acid was converted to 2,2-dimethylpentanol as described below.

A solution of 16.3 g (125 mmol) of 2,2-dimethypentanoic acid in 10 ml of dry ether was added dropwise to a stirred slurry of 7.11 g (187 mmol) of lithium aluminum hydride in 250 ml of dry ether, under argon. After addition was complete, the resultant mixture was refluxed for three hours. It was then cooled with an ice bath and excess hydride was destroyed by the dropwise addition of 10 ml of ethyl acetate. This was followed by the careful dropwise addition, with vigorous stirring, of 8 ml of water, 8 ml of 15 percent aqeous sodium hydroxide and 16 ml of water, sequentially. The resultant mixture was stirred several minutes until the solid had turned uniformly white. It was then filtered through a diatomaceous earth filter. The filter pad was rinsed thoroughly with ether. The combined filtrate was evaporated in vacuo to yield 11.3 g. The pentanol had the following spectral characteristics: nmr ($CDCl_3$) δ 0.87 (9H, broad s), 1.0–1.5 (4H, m), 2.3 (1H, broad s) and 3.36 ppm (2H, broad s); ir ($CHCl_3$) 655, 730, 900, 1030, 1205, 1360, 1470, 2880, 2950, 3200–3600 (broad) and 3600 $cm^{-1}$.

A solution of 1.0 g (10 mmol) of 2,2-dimethypentanol in 3 ml of methylene chloride was added rapidly to a stirred suspension of 4.0 g of pyridinium chlorochromate in 20 ml of methylene chloride under argon. A black gum quickly settled from the reaction mixture. The resultant mixture was stirred for two hours. It was then diluted with ether and the supernatant was decanted. The residue left in the reaction flask was extracted four more times with ether. The combined decanted extracts were filtered and evaporated. The yield of 2,2-dimethylpentanal was 0.9 g.

The process was repeated on a larger scale using 9.5 g of 2,2-dimethylpentanol with 40 g of pyridinium chlorochromate in a total of 130 ml of methylene chloride to yield 9.7 g of 2,2-dimethylpentanal: nmr ($CDCl_3$) δ 9.67 (1H, S), 1.04 (6H, S) and 0.8 to 1.6 ppm (7H, m); ir ($CDCl_3$) 905, 1230, 1365, 1470, 1725, 2720, 2880, and 2970 $cm^{-1}$.

The 2,2-dimethypentanal was substituted for the 2-hexanone of Example 1. The procedure of Example 1 was followed to obtain the corresponding acetylenic alcohol, the corresponding iodovinyl alcohol and the corresponding hydroxyl-protected iodovinyl alcohol. The acetylenic alcohol, 5,5-dimethyloct-1-yn-4RS-ol, had the following spectral characteristics: nmr ($CDCl_3$) δ 0.90 (6H, s), 0.8–1.6 (7H, m), 2.08 (1H, t, J=2.7 Hz), 2.38 (2H, m), 2.28 (1H, broad s) and 3.60 ppm (1H, d of d, J=5.0, 9.0 Hz); ir ($CHCl_3$) 860, 1030, 1365, 1470, 2100 (weak), 2860, 2950, 3300, 3200–3600 (broad) and 3580 $cm^{-1}$.

1-Iodo-5,5-dimethyloct-1E-en-4RS-ol had the following spectral characteristics: nmr ($CDCl_3$) δ 0.88 (9H, broad s), 1.0–2.0 (5H, m), 2.23 (2H, m), 3.4 (1H, m), 6.17 (1H, d, J=15 Hz) and 6.72 ppm (1H, d of t, J=15, 7 HZ); ir ($CHCl_3$) 945, 1050, 1365, 1470, 1610, 2860, 2930, 2970, 3200–3600 (broad) and 3600 $cm^{-1}$.

1-Iodo-5,5-dimethyl-4RS-(tetrahydropyranyloxy)oct-1E-ene had the following spectral characteristics: nmr ($CDCl_3$) δ 0.9 (9H, broad s), 1.0–2.0 (10H, m), 2.25 (2H, m), 3.2–4.2 (3H, m), 4.50 (1H, broad s), 6.02 (1H, d, J=14 Hz) and 6.3–7.0 (1H, m); ir ($CHCl_3$) 1020, 1070, 1130, 1380, 2860 and 2950 $cm^{-1}$.

As described in Example 1, the organolithiocuprate was prepared from the tetrahydropyranyloxy-protected iodovinyl alcohol and reacted with 4R-(tetrahydropyran-2-yloxy)-2-[7-tetrahydropyran-2-yloxy)heptyl]cyclopent-2-enone to produce the following $PGE_1$ analogue isomers, TR 4751 and 4752. The isomers were separated by chromatographic procedures.

TR 4752 Polar Isomer—$[\alpha]_D$−78.7° (c 1.11, $CHCl_3$); $R_f$ (system II) 0.40; nmr ($CDCl_3$) δ 0.83 (9H, broad s), 1.0–3.1 (21H, m), 3.1–4.3 (7H, m) and 5.48 ppm (2H, m); ir ($CHCl_3$) 970, 1080, 1160, 1240, 1740, 2860, 2940, and 3100–3600 $cm^{-1}$; ms (70 eV) m/e 368 (p), 350, 332, 317, 307, 283, 265, 254, 236.

TR 4751 Less Polar Isomer—$[\alpha]_D$−37.0° (c 1.01, $CHCl_3$); $R_f$ (system II) 0.41; nmr, ir and ms are essentially the same as those for the polar isomer above.

Example 4

1,11α,16RS-trihydroxy-17RS-methylprost-13E-en-9-one (TR 4749)

A solution of 2RS-methylpentanal was substituted for the 2,2-dimethylpentanal of Example 3. The 2RS-methylpentanal was produced as described in Example 3 by replacing 2,2-dimethylpentanoic acid with commercially available 2-methylvaleryl chloride and converting the chloride into 2-methylpentanol. The 2-methylpentanol had the following spectral characteristics: nmr ($CDCl_3$) δ 0.92 (6H, m), 1.0–2.0 (5H, m), 2.87 (1H, broad s) and 3.48 ppm (2H, d, J=5.5 Hz); ir ($CHCl_3$) 980, 1020, 1245, 1385, 1465, 2870, 2930, 2970, 3200–3600 (broad) and 3600 $cm^{-1}$.

The 2-methylpentanol was converted to 2RS-methylpentanal as described in Example 3. The product had the following spectral characteristics: nmr ($CDCl_3$) δ 9.83 (1H, d, J=2 Hz) and 0.8–1.8 ppm (11H, m); ir ($CHCl_3$) 900, 1040, 1105, 1720, 2870, 2930 and 2970 $cm^{-1}$.

The 5RS-methyloct-1-yn-4RS-ol had the following spectral characteristics: nmr ($CDCl_3$) δ 0.8–1.8 (11H, m), 2.08 (1H, t, J=3.0 Hz), 2.22 (1H, broad s), 2.40 (2H, d of d, J=3.0, 6.0 Hz) and 3.66 ppm (1H, m); ir ($CHCl_3$) 905, 1040, 1385, 1460, 2120 (weak), 2880, 2930, 2970, 3310 3200–3600 (broad) and 3600 $cm^{-1}$.

The acetylenic alcohol was converted to the corresponding iodovinyl alcohol, 1-iodo-5RS-methyloct-1E-en-4RS-ol and the hydroxyl-protected iodovinyl alcohol as described in Example 1. The iodovinyl alcohol had the following spectral characteristics: nmr (CDCl₃) 0.90 (6H, m), 1.0–2.0 (6H, m), 2.20 (2H, t, J=14 Hz) and 6.58 (1H, d of t, J=14, 7 Hz); ir (CHCl₃) 905, 950, 1205, 1385, 1460, 1612, 2880, 2940, 2960, 3200–3600 (broad) and 3600 cm⁻¹.

1-iodo-5RS-methyl-4RS-(tetrahydropyranyloxy)oct-1E-ene had the following spectral characteristics: nmr (CDCl₃) δ 0.9 (6H, m), 1.0–2.5 (13H, m), 3.3–4.2 (3H, m), 4.60 (1H, broad s), 6.06 (1H, d, J=14 Hz) and 6.53 ppm (1H, d of t, J=14, 7 Hz).

As described in Example 1, the organolithiocuprate was prepared from the tetrahydropyranyloxy-protected iodovinyl alcohol and reacted with the 2-cyclopenten-1-one of Example 1 to produce TR 4749 having the following spectral characteristics: [α]_D −62.4° (c 1.04, CHCl₃); R_f (system II) 0.29; nmr (CDCl₃) δ 0.93 (6H, m), 1.0–3.0 (23H, m), 3.3–4.3 (7H, m) and 5.52 ppm (2H, m); ir (CHCl₃) 970, 1070, 1160, 1240, 1380, 1460, 1740, 2860, 2940, and 3100–3600 cm⁻¹; ms (70 eV) m/e 354 (p) 336, 318, 307, 231, 218.

Compounds of the present invention were prepared wherein R₂ and R₃ are closed to form cycloalkyl having from 5 to 6 carbon atoms inclusive and wherein R₃ and R₄ are closed to form cycloalkyl having from 4 to 8 carbon atoms inclusive. Example 5 describes the preparation of an R₂ and R₃ ring-closed compound from a cycloalkene oxide as indicated in Table E.

Example 5

15,20-Cyclo-1,11α,16S-trihydroxy-prost-13E-en-9-one and 15,20-Cyclo-1,11α,16R-trihydroxy-prost-13E-en-9-one (TR 4848 and TR 4840)

A solution of 4.0 g of commercially available cyclohexene oxide and 41 ml of hexamethylphosphoramide (HMPA) was stirred under argon at 25°. Commerically available lithium acetylide ethylene diamine complex (9.65 g) was added and the reaction mixture heated at 80° for two hours. The reaction mixture was cooled to 0° and 20 percent aqueous ammonium chloride added. The mixture was extracted with ether. The extracts were washed with 10 percent HCl, water (five times), saturated aqueous NaHCO₃ and brine, then dried, filtered, and distilled using aspirator vacuum to yield 2.98 g of (±)-trans-2-ethynylcyclohexanol, bp 73°–75°. The product had the following spectral characteristics: nmr (CDCl₃) δ 0.8–2.5 (10H, m), 2.58 (1H, broad s) and 3.55 (1H, broad m); ir (CHCl₃) 840, 1010, 1070, 1110, 1270, 1450, 2110, 2860, 2950, 3300, 3200–3600 (broad) and 3575 cm⁻¹.

The acetylenic alcohol was converted into the corresponding iodovinyl alcohol and protected iodovinyl alcohol as described in Example 1. The 4-methyloct-1-yn-4RS-ol of Example 1 was replaced with trans-2-ethynylcyclohexan-1RS-ol; the following change was made in the procedure. When the iodine solution was added to the reaction mixture, it was added only until color persisted for one minute or more. Product isolation proceeded as in Example 1. The resultant product, trans-2-(2E-iodoethenyl) cyclohexan-1RS-ol had the following spectral characteristics: nmr (CDCl₃) 0.8–2.3 (10H, m), 3.3 (1H, broad m), 6.13 (1H, d, J=14 Hz) and 6.50 Hz (1H, d of d, J=14, 7 Hz).

The tetrahydropyranyloxy-protected iodovinyl alcohol, trans-2-(2E-iodoethenyl)-1RS-(tetrahydropyranyloxy)cyclohexane, had the following spectral characteristics: nmr (CDCl₃) δ 0.8–2.2 (15H, m), 3.2–4.2 (3H, M), 4.5 (1H, broad s), 6.02 (1H, d, J=14 Hz) and 6.53 ppm (1H, d of t, J=14, 7 Hz); ir (CHCl₃) 860, 900, 980, 1020, 1075, 1120, 1360, 1450, 1610, 2850, and 2950 cm⁻¹.

The synthesis of the PGE₁ analogue was carried out as described in Example 1. Chromatography of the crude product yielded 15S, 20-cyclo-1,11α,16R-trihydroxyprost-13E-en-9-one and 15R, 20-cyclo-1,11α,16S-trihydroxyprost-13E-en-9-one. The physical characteristics of the isomers were:

Less polar—R_f (system II) 0.38 nmr (CDCl₃) δ 0.9–2.5 (23H, complex), 2.28 (3H, broad s), 3.62 (2H, broad t), 3.2–4.2 (2H, complex) and 5.57 (2H, m); ir (CHCl₃) 970, 1460, 1740, 3200–3600 and 3600 cm⁻¹; ms (70 eV) m/e 338, 320, 302, 389.

More polar—[α]_D −70.5° (c 0.54, CHCl₃); R_f (system II) 0.33 nmr (CDCl₃) δ 0.9–2.5 (23H, complex), 2.8–4.2 (5H, complex), 3.6 (2H, broad t) and 5.42 ppm (2H, m); ir (CHCl₃) 970, 1450, 1740, 3200–3600 adn 3600 cm⁻¹; ms as above for the less polar isomer.

Example 6

15,19-cyclo-20-nor-1,11α,16R-trihydroxy-prost-13E-en-9-one and 15,19-cyclo-20-nor-1,11α,16S-trihydroxy-prost-13E-en-9-one (TR 4844 and TR 4846)

The cyclohexene oxide of Example 5 was replaced with commercially available cyclopentene oxide. The procedure of Example 5 was followed to convert the cyclopentene oxide into the corresponding acetylenic alcohol, trans-2-ethynylcyclopentan-1RS-ol. The acetylenic alcohol had the following spectral characteristics: bp 72° (20 mm); nmr (CDCl₃) δ 1.0 to 3.0 (9H, m) and 4.25 ppm (1H, m); ir (CHCl₃) 860, 900, 995, 1080, 1215, 1450, 2110, 2860, 2960, 3300, 3200–3600 (broad) and 3600 cm⁻¹.

The procedure of Example 5 was followed to obtain the corresponding iodovinyl alcohol and the corresponding protected iodovinyl alcohol by replacing trans-2-ethynylcyclohexan-1RS-ol with trans-2-ethynylcyclopentan-1RS-ol. The iodovinyl alcohol, trans-2-(2E-iodoethenyl)-cyclopentan-1RS-ol had the spectral characteristics: nmr (CDCl₃) δ 0.8–2.7 (8H, m), 3.85 (1H, broad m), 6.10 (1H, d, J=14 Hz) and 6.50 (1H, d of d, J=14, 7 Hz); ir (CHCl₃) 870, 910, 960, 1040, 1080, 2870, 2940, 3200–3600 (broad) and 3580 cm⁻¹.

The trans-2-(2E-iodoethenyl)-1RS-(tetrahydropyranyloxy)cyclopentane had the following spectral characteristics: nmr (CDCl₃) δ 0.8–2.3 (13H, m) 3.2–4.2 (3H, m), 4.65 (1H, broad s), and 5.9 to 6.8 ppm (2H, m); ir (CHCl₃) 865, 910, 975, 1030, 1075, 1130, 2880 and 2960 cm⁻¹.

The synthesis of the PGE₁ analogue was carried out as described in Example 1. Chromatography of the crude product yielded the two isomers referred to earlier. The isomers had the following spectral characteristics:

Less polar—[α]_D −22.9° (c 0.65, CHCl₃); R_f (System II) 0.24 nmr (CHCl₃) δ 1.0–2.4 (23H, complex), 2.82 (3H, broad s), 3.6 (2H, broad t), 3.3–4.2 (2H, complex) and 5.57 ppm (2H, m); ir (CHCl₃) 970, 1460, 1740, 3200–3600 and 3600 cm⁻¹; ms (70 eV) m/e 324, 306, 288, 278, 236.

More polar—[α]_D −65.9° (c 0.61, CHCl₃); R_f (system II) 0.20 nmr (CDCl₃) δ 0.9–2.5 (23H, complex), 2.7–4.2 (7H, complex) and 5.52 (2H, m); ir (CHCl₃) 970, 1460, 1740, 3200–3600 and 3600 cm$^{-1}$; ms as above for the less polar isomer.

The following $R_3$ and $R_4$ ring-closed compounds wherein $R_3$ and $R_4$ form a cycloalkyl having from 4 to 8 carbon atoms inclusive, were prepared as described in Example 1.

Example 7

16,20-Methano-1,11α,16-trihydroxyprost-13E-en-9-one (TR 4703)

A solution of commercially available cyclohexanone was substituted for the 2-hexanone of Example 1. The procedure of Example 1 was followed to obtain the corresponding acetylenic alcohol, the corresponding iodovinyl alcohol and the corresponding hydroxyl-protected iodovinyl alcohol. The acetylenic alcohol, 1-(prop-2-ynyl)cyclohexanol, had the following spectral characteristics: nmr (CDCl$_3$) δ 1.0–2.0 (10H, m), 2.0–2.2 (2H, m) and 2.39 ppm (2H, m); ir (CHCl$_3$) 870, 980, 1060, 1150, 1270, 1450, 2120 (weak), 2860, 2930, 3300, 3200–3600 (broad) and 3570 cm$^{-1}$.

The cyclohexanol was converted into the corresponding iodovinyl alcohol by replacing 4-methyloct-1-yn-4RS-ol with 1-(prop-2-ynyl)cyclohexanol. The yield was low (0.54 g from 7.0 g of the hexanol). An alternate procedure, described below, was devised to prepare additional amounts of the iodovinyl alcohol and corresponding protected iodovinyl alcohol from 1-(prop-2-ynyl)cyclohexanol.

A solution of 2.9 g (21 mmol) of (prop-2-ynyl)cyclohexanol in 10 ml of dry ether was stirred under argon as 0.24 ml (26 mmol) of dihydropyran was added followed by about 5 mg of toluenesulfonic acid. After one hour, tlc (CHCl$_3$, silica gel) analysis indicated that significant starting material remained. Another 0.2 ml of dihydropyran and about 5 mg of toluenesulfonic acid were added. Twice more at one hour intervals, 0.2 ml portions of dihydropyran along with a small amount of toluenesulfonic acid were added to the reaction mixture. It was left to stir under argon at room temperature for 15 hours. Potassium carbonate was then added to the mixture and it was stirred for several minutes before it was washed with water. The wash solution was back extracted with ether and the combined extracts were then washed with brine, dried (Na$_2$SO$_4$) and evaporated in vacuo to yield 4.6 g of 1-(tetrahydropyran-2-yloxy)-1-(prop-2-ynyl)cyclohexane) having the following spectral characteristics: nmr (CDCl$_3$) δ 1.0–2.5 (19H, m), 3.6 (2H, broad m) and 4.65 ppm (1H, broad s); ir (CHCl$_3$) 980, 1030, 1050, 1070, 1120, 1150, 1270, 1450, 2120, (weak) 2760, 2930 and 3300 cm$^{-1}$.

A 200 ml portion of 1M borane in tetrahydrofuran was stirred under argon with −10° bath cooling in a flask fitted with a dry ice condensor. A total of 46 ml (400 mmol) of 2-methyl-2-butene was then added slowly via syringe below the surface of the borane solution. The reaction mixture was then stirred one hour at 0° and then left overnight in a refrigerator.

A 10 ml portion of the above disiamylborane solution was stirred under argon with ice bath cooling as 2.4 g of 1-(tetrahydropyran-2-yloxy)-1-(prop-2-ynyl)-cyclohexane, was added slowly. The resultant solution was stirred at room temperature for two hours. Tlc (CHCl$_3$, silica gel) showed that the reaction was not complete. A second 10 ml portion of disiamylborane solution was added to the reaction mixture. After another 1.5 hour the reaction was quenched by the addition of 3.3 g of trimethylamine oxide dihydrate portionwise over 30 minutes. The resultant mixture was stirred at 0° for one hour. A 33 ml portion of 1M aqueous sodium hydroxide was then added, quickly followed by a solution of 7.6 g of iodine in 40 ml of dry tetrahydrofuran. The resultant mixture was stirred one hour without a cooling bath and then poured into 100 ml of water. Sodium thiosulfate was then added until the color of excess iodine had dissipated. The resultant mixture was extracted with ether. The extract was washed with water and then brine. It was evaporated in vacuo to yield 9.00 g of residue. This residue was dissolved in methanol and benzene which were then removed by evaporation in vacuo to yield 5.0 g of residue. This residue was chromatographed on silica gel using chloroform elution to yield 2.4 g of pure material.

The 1-(3-iodoprop-2E-enyl)-1-(tetrahydropyranyloxy)cyclohexane had the following spectral characteristics: nmr (CDCl$_3$) δ 0.90 (3H, m), 1.0–2.0 (16H, m), 2.35 (2H, d, J=8 Hz), 3.3–4.3 (2H, m), 4.83 (1H, broad s), 6.09 (1H, d, J=14 Hz) and 6.77 ppm (1H, d of t, J=14, 7 Hz); ir (CHCl$_3$) 960, 990, 1030, 1075, 1125, 1460, 1610, 2870 cm$^{-1}$.

The synthesis of the PGE$_1$ analogue was carried out as described in Example 1. The prostaglandin analogue had the following spectral characteristics: [α]$_D$ −55.5° (c 1.0, CHCl$_3$); R$_f$ (system II) 0.22; nmr (CDCl$_3$) δ 1.0–2.8 (29H, m), 2.99 (3H, broad s), 3.73 (2H, t, J=6.0 Hz), 4.17 (1H, m) and 5.70 ppm (2H, m); (CHCl$_3$) 910, 970, 1070, 1150, 1240, 1340, 1380, 1450, 1740, 2860, 2950 and 3200–3600 cm$^{-1}$; ms (70 eV) m/e 334 (p—H$_2$O), 262, 253, 235, 217.

Example 8

20-Nor-16,19-cyclo-1,11α,16-trihydroxyprost-13E-en-9-one (TR 4753)

A solution of commercially available cyclobutanone was substituted for the 2-hexanone of Example 1. The procedure of Example 1 was followed to obtain the corresponding acetylenic alcohol, the corresponding iodovinyl alcohol, and the corresponding hydroxyl-protected iodovinyl alcohol. The acetylenic alcohol, 1-(prop-2-ynyl)cyclobutanol, had the following spectral characteristics: bp 60–62° (20 mm); nmr (CDCl$_3$) complex m at δ 0.8–2.5 ppm; ir (CHCl$_3$) 850, 1060, 1130, 1250, 1370, 1455, 2240, 2860, 2930, 2970, 3300, 3200–3600 (broad) and 3600 cm$^{-1}$.

The acetylenic alcohol was converted into the corresponding iodovinyl alcohol and the corresponding protected iodovinyl alcohol by replacing 4-methyloct-1-yn-4RS-ol with 1-(prop-2-ynyl)cyclobutanol. The 1-(3-iodoprop-2E-enyl)cyclobutanol had the following spectral characteristics: nmr (CDCl$_3$) δ 1.0–2.5 (9H, m), 6.12 (1H, d, J=14 Hz) and 6.60 ppm (1H, d of t, J=14, 7 Hz).

The 1-(3-iodoprop-2E-enyl)-1-(tetrahydropyranyloxy)cyclobutane had the following spectral characteristics: nmr (CDCl$_3$) δ 1.2–2.3 (13H, m), 2.4 (2H, d, J=7 Hz), 3.3–4.2 (2H, m), 4.70 (1H, broad s), 6.08 (1H, s, J=14 Hz) and 6.63 ppm (1H, d of t, J=14, 7 Hz); ir (CHCl$_3$) 860, 980, 1020, 1070, 1120, 1275, 1440, 1610, 2850, 2940 cm$^{-1}$.

The synthesis of the PGE$_1$ analogue was carried out as described in Example 1. The prostaglandin analogue had the following spectral characteristics: [α]$_D$ −37.1° (c 0.97, CHCl$_3$); R$_f$ (system II) 0.16; nmr (CDCl$_3$) δ 0.8–2.7 (24H, m), 3.2–4.3 (6H, m) and 5.57 ppm (2H, m); ir (CHCl$_3$) 970, 1020, 1075, 1160, 1220, 1265, 1345, 1440, 1740, 2860, 2930, and 3100–3600 cm$^{-1}$; ms (70 eV) m/e 306 (p—H$_2$O), 278, 236.

Example 9

16,20-Methano-18RS-methyl-1,11α,16RS-trihydroxy-prost-13E-en-9-one (TR 4851)

A solution of commercially available 3RS-methylcyclohexanone was substituted for the 2-hexanone of Example 1. The procedure of Example 1 was followed to obtain the corresponding acetylenic alcohol, the corresponding iodovinyl alcohol and the corresponding hydroxyl-protected iodovinyl alcohol. The acetylenic alcohol, 3RS-methyl-1RS-(prop-2-ynyl)cyclohexanol, had the following spectral characteristics: nmr (CDCl$_3$) δ 0.88 (3H, d, J=6 Hz), 1.0–2.0 (10H, m), 2.07 (1H, t, J=2.5 Hz) and 2.32 ppm (2H, d, J=2.5 Hz); ir (CHCl$_3$) 950, 1000, 1100, 1165, 1260, 1380, 1450, 2110 (weak), 2860, 2930, 3300, 3200–3600 (broad) and 3570 cm$^{-1}$.

The acetylenic alcohol was converted into the corresponding iodovinyl alcohol and the corresponding protected iodovinyl alcohol by replacing the 4-methyloct-1-yn-4RS-ol with the above 3RS-methyl-1RS-(prop-2-ynyl)cyclohexanol. The resultant product, 1RS-(3-iodoprop-2E-enyl)-3RS-methylcyclohexanol had the following spectral characteristics: (CDCl$_3$) δ 0.90 (3H, d, J=6 Hz) 1.0–1.9 (10H, m), 2.18 (2H, d, J=7 Hz), 6.10 (1H, d, 7=14 Hz) and 6.65 ppm (1H, d of t, J=14, 7 Hz); ir (CHCl$_3$) 945, 995, 1155, 1380, 1450, 1608, 2860, 2930, 3200–3600 (broad) and 3600 cm$^{-1}$.

The 1RS-(3-iodoprop-2E-enyl)-3RS-methyl-1RS-(tetrahydropyranyloxy)cyclohexane had the following spectral characteristics: nmr (CDCl$_3$) δ 0.86 (3H, broad d, J=5.5 Hz), 1.0–2.2 (15H, m), 2.27 (2H, broad d, J=7.0 Hz), 3.2–4.2 (2H, m), 4.71 (1H, broad s), 5.98 (1H, d, J=14.5 Hz) and 6.73 ppm (1H, d of t, J=14.5, 7.5 Hz); ir (CHCl$_3$) 865, 950, 995, 1025, 1070, 1125, 1360, 1445, 2870, and 2950 cm$^{-1}$.

The synthesis of the PGE$_1$ analogue was carried out as described in Example 1. The prostaglandin analogue had the following spectral characteristics: [α]$_D$ −51.7° (c 0.99, CHCl$_3$); R$_f$(system II) 0.26; mass spectrum m/e 348 (M$^+$—H$_2$O) 330 (M$^+$—2H$_2$) 254 (M$^+$—C$_7$H$_{13}$O); NMR (CDCl$_3$) δ 0.90 (broad d, 3) 2.6–4.3 (complex, 4) 3.60 (broad t, 2) 5.52 (m, 2); ir (CHCl$_3$) 3600, 3400 (broad) 1740, 970, 950 cm$^{-1}$.

Example 10

16,18-Methano-1,11α,16RS-trihydroxyprost-13E-en-9-one (TR 4770)

A solution of 3-ethylcyclobutanone, prepared as described below, was substituted for the 2-hexanone of Example 1.

A −10° slurry of 11.4 g of lithium aluminum hydride and 160 ml of ether was stirred together in a 2 liter 3-necked flask equipped with a reflux condenser, argon inlet, addition funnel and mechanical stirring. A solution of 37.6 g of diethyl ethylmalonate, in 40 ml ether was added dropwise. After addition was complete, the reaction mixture was refluxed for 1.5 hours. The reaction mixture was cooled in an ice bath and 16 ml of ethyl acetate added, followed by 12 ml of water, 12 ml of 15 percent aqueous sodium hydroxide and 20 ml of water. The reaction mixture was stirred at 25° for one hour, then filtered and the cake washed with ether. The organic layer was isolated, washed with brine, dried over MgSO$_4$, filtered, and evaporated in vacuo. The resultant oil was distilled (aspirator vacuum) to yield 10.5 g of (2-ethylpropane)-1,3-diol as a clear oil (bp 115°). The material had the following spectral characteristics: nmr (CDCl$_3$) δ 0.8 to 1.9 (6H, m) and 3.75 ppm (6H, m); ir (film) 960, 1000, 1035, 1090, 1380, 1460, 2870, 2930, 2960, and 3200 to 3600 cm$^{-1}$.

A solution of 10.5 g of the (2-ethyl)propane-1,3-diol, in 155 ml of dry pyridine was stirred at −10° under argon and 48 g of toluenesulfonyl chloride was added in small portions. The reaction mixture was stirred for 4.5 hours at −10°, then poured into 620 ml 6N HCl (chilled). The mixture was acidified and the aqueous layer extracted with ether. The extracts were combined and washed with saturated aqueous sodium bicarbonate, and brine, dried over MgSO$_4$, filtered and evaporated in vacuo to yield an orange oil. NMR spectrum indicated 50 percent reaction. The oil was redissolved in 155 ml pyridine, cooled to −10° and treated with 31.0 g of toluenesulfonyl chloride. The reaction mixture was stirred for 1.5 hours at −10°, then stored at 0° for 16 hours. The 1,1-di(toluenesulfonyloxymethyl)propane was a white solid. The material had the following spectral characteristics: nmr (CDCl$_3$) δ 0.6 to 2.5 (6H, m), 2.42 (6H, s), 3.92 (4H, d, J=5 Hz), 7.32 (4H, d, J=8 Hz) and 7.74 pm (4H, d, J=8 Hz); ir (CHCl$_3$) 810, 840, 950, 1100, 1175, 1360, 2890, 2970 and 3030 cm$^{-1}$.

A portion of 5.9 g sodium metal g was granulated in 40 ml xylene by stirring vigorously at 120° under argon in a 1 liter three-necked round-bottomed flask equipped with a reflux condenser, argon inlet, addition funnel and mechanical stirring. An additional 138 ml of xylene was added and the heating bath removed. Diethyl malonate (39 ml) was added dropwise and the reaction mixture heated to 95° for 15 minutes. A solution of 48.0 g of 1,1-di(toluenesulfonyloxymethyl)propane in 150 ml xylene was added dropwise. The yellow reaction mixture was refluxed at 150°–160° and stirred 18 hours, then cooled and 170 ml water added. The layers were separated and the aqueous layer acidified with 10 percent HCl. The aqueous layer was extracted with ether. The organic layers were combined, washed with brine, dried over MgSO$_4$, filtered through Celite, evaporated in vacuo and distilled (oil pump vacuum) to afford 11.4 g of 1,1-bis(ethoxycarboxy)-3-ethylcyclobutane as a clear oil (bp 98°–105°). The material had the following spectral characteristics: nmr (CDCl$_3$) δ 0.76 (3H, t, J=7.0 Hz), 1.24 (6H, t, J=7.0 Hz), 1.9–2.8 (7H, m) and 4.18 ppm (4H, q, J=7.0 Hz); ir (CHCl$_3$) 860, 1015, 1060, 1145, 1265, 1370, 1460, 1725, 2870, 2930 and 2960 cm$^{-1}$.

A solution of 15.7 g of the 1,1-bis(ethoxycarbonyl)-3-ethyl cyclobutane, in 13 ml of ethanol was added to a stirred solution of 15 g of potassium hydroxide in 155 ml of ethanol. The reaction mixture was refluxed for 2.5 hours under argon. The reaction mixture was cooled and ethanol removed by evaporation in vacuo. The residue was dissolved in water. The aqueous solution was extracted twice with ether. The ether was back-extracted twice with water. The combined aqueous layers were acidified with 6N HCl and extracted with ether. The extracts were washed with brine, dried, filtered and evaporated in vacuo to yield 12.7 grams of a yellow solid. An NMR spectrum indicated that the hydrolysis had not gone to completion. The crude product was dissolved in ethanol (75 ml) and 7.5 g of KOH added. The reaction mixture was stirred 18 hours at 25°, then processed as above to yield 10.9 g of 3-ethylcyclobutane-1,1-dicarboxylic acid, a light yellow solid. The material had the following spectral characteristics: nmr (CDCl$_3$) δ 0.80 (3H, t, J=7.0 Hz) 1.41, (2H, m), 1.6–3.2 (5H, m) and 11.5 ppm (2H, broad s); ir (CHCl$_3$) 940, 1040, 1170, 1290, 1420, 1705 and 2400–3400 cm$^{-1}$ (broad).

A 10.9 g portion of the 3-ethylcyclobutane-1,1-dicarboxylic acid, was heated to 180°–190° for two hours, followed by distillation (oil pump vacuum) to obtain 6.6 g of 3-ethylcyclobutane carboxylic acid as a clear oil (bp 95°–97°). The material had the following spectral characteristics: nmr (CDCl$_3$) δ 0.75 (3H, t, J=7.0 Hz), 1.4 (2H, m), 1.5–2.7 (5H, m), 2.98 (1H, m) and 11.8 ppm (1H, broad s); ir (CHCl$_3$) 940, 1120, 1250, 1420, 1460, 1700 and 2400–3400 cm$^{-1}$ (broad).

A solution of 6.61 g of 3-ethylcyclobutane-1-carboxylic acid, in 52 ml of distilled ether was stirred under argon at 0°. Methyllithium (85.0 ml of a 1.53M solution in ether) was added dropwise over a 30 minute period. The reaction mixture was stirred for three hours at 25°, then quenched with 7.3 water-methanol. The layers were separated, and the aqueous layer extracted with ether. The combined organic layers were washed with brine, dried, filtered and the solvents evaporated in vacuo. The resultant oil was distilled (aspirator vacuum) to afford 5.5 g of 1-acetyl-3-ethylcyclobutane, as a clear oil (bp 64°–67°). The material had the following spectral characteristics: nmr (CDCl$_3$) δ 0.80 and 0.82 (3H total, pair of t, each J=7.0 Hz), 1.10 and 1.12 (ca. 1.5H total, pair of s, side product 1-[2-hydroxyprop-2-yl]-3-ethylcyclobutane), 1.0–2.4 (7H, m), 2.07 and 2.09 (3H total, pair of s) and 2.7–3.5 ppm and (1H, m); ir (CHCl$_3$) 935, 1175, 1370, 1460, 1705, 2870, 2930 and 2970 cm$^{-1}$, also small 3200–3600 broad and 3600 cm$^{-1}$ for the side product noted above.

A solution of 5.5 g of the 1-acetyl-3-ethylcyclobutane, and 10.7 g of m-chloroperbenzoic acid in 107 ml chloroform was allowed to stand for five days in the dark. The reaction mixture was cooled via external ice cooling and filtered. The filtrate was diluted with CHCl$_3$ and washed with 10 percent aqueous sodium thiosulfate, 10 percent aqueous sodium carbonate and brine, dried over Na$_2$SO$_4$, and filtered. The solution was subjected to distillation (aspirator vacuum) to afford 3.55 g of 1-acetoxy-3-ethylcyclobutane, as a clear oil (bp 65°–67°). The material had the following spectral characteristics: nmr (CDCl$_3$) δ 0.82 (3H, t, J=7.0 Hz) 1.10 and 1.12, (same side product noted in the 1-acetyl compound spectra), 1.0–2.5 (7H, m), 2.01 (3H, s) and 4.9 (1H, m); ir (CHCl$_3$) 950, 1040, 1085, 1205, 1250, 1375, 1460, 1720, 2870, 2925 and 2960 cm$^{-1}$ along with trace of 3200–3600 (broad) and 3600 cm$^{-1}$ for the same side product noted in the 1-acetyl the compound spectra.

A solution of the 1-acetoxy-3-ethylcyclobutane, in 200 ml of KOH in 3:1 methanol-water was stirred at 25° for 24 hours. The mixture was poured into 130 ml of brine and 130 ml of ether. The layers were separated and the aqueous NaHCO$_3$ and brine, then dried and filtered. The product was isolated by vacuum distillation (aspirator) to yield 3.55 g of 3-ethyl-cyclobutanol (bp 59°–62°). The material had the following spectral characteristics: ir (CHCl$_3$) 935, 1050, 1090, 1110, 1220, 1310, 1380, 1460, 2860, 2930, 2970, 3200–3600 (broad) and 3600 cm$^{-1}$.

A solution of 3.55 g of 3-ethylcyclobutanol in 135 ml dry acetone was stirred under argon at −10°. Standard Jones Reagent (30.5 ml) was added dropwise. The reaction mixture was stirred for two hours at −10°, then 25 ml of isoproponol was added dropwise and the reaction mixture stirred at −10° for 10 minutes. The supernatant liquid was decanted and filtered into a separatory funnel. The residue was washed three times with ether and each wash was decanted and filtered. Brine (80 ml) was added to the combined filtrates and the layers separated. The aqueous layer was extracted with ether. The combined extracts were washed with saturated aqueous NaHCO$_3$ and brine, then dried (MgSO$_4$) and filtered. Distillation by water aspirator vacuum afforded 1.67 ml of 3-ethylcyclobutanone as a clear oil (bp 74°–75°) having the following spectral characteristics: ir (CHCl$_3$) 1080, 1110, 1310, 1380, 1460, 1780, 2870, 2925, and 2955 cm$^{-1}$.

The procedure of Example 1 was used to prepare the corresponding iodovinyl alcohol and the corresponding hydroxyl-protected iodovinyl alcohol. The acetylenic alcohol, 3-ethyl-1-(prop-2-ynyl)cyclobutanol had the following spectral characteristics: nmr (CDCl$_3$) δ 0.83 (3H, broad t, J=7.0 Hz) and 1.0–2.5 ppm (11H, m); ir (CHCl$_3$) 850, 1050, 1125, 1245, 2240 (weak), 2870, 2925, 2970, 3300, 3200–3600 (broad) and 3600 cm$^{-1}$.

The acetylenic alcohol was converted into the corresponding iodovinyl alcohol and the corresponding protected iodovinyl alcohol by replacing the 4-methyloct-1-yn-4RS-ol with the above 3-ethyl-1-(prop-2-ynyl)cyclobutanol. The resultant product, 1-(3-iodoprop-2E-enyl)-3-ethylcyclobutanol, had the following spectral characteristics: nmr (CDCl$_3$) δ 0.80 (3H, t, J=5 Hz), 1.0–2.2 (7H, m), 2.2–2.5 (3H, m) 6.17 (1H, d, J=15 Hz), and 6.67 ppm (1H, d of t, J=15, 7 Hz); ir (CHCl$_3$) 945, 1115, 1285, 1460, 1610, 2860, 2930, 2960, 3200 to 3600 (broad) and 3600 cm$^{-1}$.

The 1-(3-iodoprop-2E-enyl)-3-ethyl-1-(tetrahydropyranyloxy)cyclobutane had the following spectral characteristics: nmr (CDCl$_3$) δ 0.80 (3H, broad t, J=6 Hz), 1.0–2.4 (15H, m), 3.2–4.2 (2H, m), 4.78 (1H, broad s), 6.13 (1H, d, J=14 Hz) and 6.63 (1H, d of t, J=14, 7 Hz); ir (CHCl$_3$) 860, 945, 980, 1020, 1070, 1125, 1280, 1610, 2850, 2950 cm$^{-1}$.

The synthesis of the PGE$_1$ analogue was carried out as described in Example 1. The prostaglandin analogue had the following spectral characteristics: [α]$_D$ −50.6° (c 0.97, CHCl$_3$); R$_f$(system II) 0.23; mnr (CDCl$_3$) δ 0.81 (3H, m), 1.0–3.0 (25H, m), 3.60 (5H, broad s), 4.0 (1H, m) and 5.57 (2H, m); ir (CHCl$_3$) 900, 970, 1080, 960, 1740, 2860, 2940 and 3100–3600 cm$^{-1}$; ms (70 eV) m/e 334 (p—H$_2$O), 316 (p—2H$_2$O), 278, 236, 235.

The following R$_3$ and R$_4$ ring-closed compounds wherein R$_3$ and R$_4$ form a bicycloalkyl or bicycloalkenyl compound were prepared as described below.

Example 11

16,18-methano-17,20-methano-1,11α,16RS-trihydroxyprosta-13E, 19-dien-9-one (TR 4803)

A solution of bicyclo[3.2.0]hept-2-en-6-one was substituted for the 2-hexanone of Example 1. The bicyclo[3.2.0]hept-2-en-6-one was produced as described below [See *Tetrahedron Letters* 307 (1970)].

The bicyclo[3.2.0]hept-2-en-6-one had the following spectral characteristics: (CDCl$_3$) δ 2.2–4.2 ppm (6H, m) and 5.83 ppm (2H, m); ir (CHCl$_3$) 1080, 1150, 1345, 1775, 2860 and 2920 cm$^{-1}$.

The procedure of Example 1 was followed to obtain the corresponding acetylenic alcohol, the corresponding iodovinyl alcohol and the corresponding protected iodovinyl alcohol by replacing the 4-methyloct-1-yn-4RS-ol with the acetylenic alcohol, 6-(prop-2-ynyl)-bicyclo[3.2.0]hept-2-en-6RS-ol.

The acetylenic alcohol had the following spectral characteristics: nmr (CDCl$_3$) δ 1.5–3.2 (10H, m) and 5.83 (2H, m); ir (CHCl$_3$) 690, 930, 1170, 1260, 1350, 1415, 2120 (weak), 2850, 2930, 3300, 3200–3600 (broad) and 3570 cm$^{-1}$.

The 6-(3-iodoprop-2E-enyl)bicyclo[3.2.0]hept-2-en-6RS-ol had the following spectral characteristics: nmr (CHCl$_3$) δ 1.5–3.2 (9H, m), 5.82 (2H, m), 6.10 (1H, d, J=14 Hz) and 6.59 ppm (1H, d of t, J=14, 7 Hz).

The 6-(3-iodoprop-2E-enyl)-6RS-(tetrahydropyranyloxy)bicyclo[3.2.0]hept-2-ene had the following spectral characteristics: nmr (CDCl$_3$) δ 1.2–3.0 (14H, m), 3.2–4.2 (2H, m), 4.60 (1H, broad s), 5.77 (2H, broad s), 6.08 (1H, d, J=14 Hz) and 6.60 ppm (1H, d of t, J14, 7 Hz); ir (CHCl$_3$) 870, 910, 990, 1030, 1075, 1130, 1610, 2860 and 2950 cm$^{-1}$.

The synthesis of the PGE$_1$ analogue was carried out as described in Example 1. The prostaglandin analogue had the following spectral characteristics:

[α]$_D$−43.9° (c 1.0, CHCl$_3$); R$_f$(system II) 0.27; nmr (CDCl$_3$) δ 1.0–3.2 (28H, m), 3.63 (2H, t, J=6.0 Hz), 4.0 (1H, m) and 5.5–6.1 ppm (2H, m); ir (CHCl$_3$) 970, 1070, 1160, 1230, 1350, 1430, 1740, 2860, 2930 and 3200–3600 cm$^{-1}$; ms (70 eV) m/e 362 (p), 344 (p—H$_2$O), 326, 296, 278, 261, 233.

Example 12

16,18-Methano-17,20-ethano-1,11α,16RS-trihydroxyprost-13E-en-9-one and 16,18-Methano-17,20-ethano-1,16RS-dihydroxyprosta-10,13E-dien-9-one (TR 4804 and TR 4806)

A solution of bicyclo[4.2.0]octan-7-one was substituted for the 2-hexanone of Example 1. The bicyclo[4.2.0]octan-7-one was prepared as described in *Tetrahedron Letters* 4753 (1971).

The bicyclo[4.2.0]oct-2-en-7-one compound was converted into bicyclo[4.2.0]octan-7-one as follows.

A solution of 4.2 g of bicyclo[4.2.0]oct-2-en-7-one in isopropanol, total solution of 100 ml, was hydrogenated over 0.5 g of platinum oxide at 50 PSI of hydrogen in a Parr shaker for 18 hours. The catalyst was removed by filtration and the filtrate was evaporated to yield 3.2 g of the compound, having the following spectral characteristics: nmr 0.8 to 3.5 ppm (m); ir 1040, 1090, 1450, 1765, 2860 and 2930 cm$^{-1}$.

The procedure of Example 1 was followed to obtain the corresponding acetylenic alcohol, the corresponding iodovinyl alcohol and the corresponding protected iodovinyl alcohol by replacing 4-methyloct-1-yn-4RS-ol wih the acetylenic alcohol, 7-(prop-2-ynyl)bicyclo[4.2.0]octan-7RS-ol. The acetylenic alcohol had the following spectral characteristics: nmr (CDCl$_3$) δ 1.0–2.2 (13H, m), 2.28 (1H, s) and 2.47 ppm (2H, d, J=2.5 Hz); ir (CHCl$_3$) 900, 1070, 1140, 1260, 1460, 2120 (weak), 2860, 2930, 3300, 3200 to 3600 (broad) and 3570 cm$^{-1}$.

The 7-(3-iodoprop-2E-enyl)bicyclo[4.2.0]octan-7RS-ol had the following spectral characteristics: nmr (CDCl$_3$) δ 1.0–2.2 (13H, m), 2.37 (2H, d, J=6 Hz), 6.10 (1H, d, J=41 Hz) and 6.72 ppm (1H, d of t, J=14, 7 Hz); ir (CHCl$_3$) 905, 950, 1075, 1100, 1130, 1260, 1455, 1610, 2850, 2930, 3200–3600 (broad) and 3600 cm$^{-1}$.

The 7-(3-iodoprop-2E-enyl)-7RS-(tetrahydropyranyloxy)bicyclo[4.2.0]octane had the following spectral characteristics: nmr (CDCl$_3$) δ 0.8–2.6 (20H, m), 3.2–4.2 (2H, m), 4.57 (1H, broad s), 6.02 (1H, d, J=14 Hz) and 6.3–6.9 (1H, m); ir (CHCl$_3$) 870, 945, 975, 1020, 1070, 1120, 1270, 1450, 2850 and 2940 cm$^{-1}$.

The synthesis of the PGE$_1$ analogue was carried out as described in Example 1. A small amount of the PGA$_1$ prostaglandin analogue was produced as a sideproduct. The prostaglandin analogues had the following spectral characteristics:

TR 4804—[α]$_D$−44.6° (c 1.0, CHCl$_3$); R$_f$(system II) 0.34; nmr(CDCl$_3$) δ 1.0–3.2 (32H, m), 3.58 (2H, t, J=6.0 Hz), 3.98 (1H, m) and 5.56 ppm (2H, m); ir (CHCl$_3$) 900, 970, 1070, 1150, 1240, 1345, 1460, 1740, 2860, 2970 and 3200–3600 CM$^{-1}$; ms (70 eV) m/e 378 (p), 360 (p—H$_2$O), 296, 278, 236.

TR 4806—[α]$_D$+64.4° (c 1.0, CHCl$_3$); R$_f$(system II) 0.51; nmr (CDCl$_3$) 1.0–2.7 (29H, m), 3.24 (1H, m), 3.62 (2H, t, J=6.0 Hz), 4.03 (1H, m), 5.60 (2H, m) 6.14 (1H, m) and 7.50 ppm (1H, m); ir (CHCl$_3$) 930, 970, 1050, 1140, 1215, 1340, 1455, 1595, 1700, 2860, 2930, 3200–3600 and 3600 cm$^{-1}$; ms (70 eV) m/e (360 (p), 278, 236, 217.

Example 13

16,18-Methano-17,20-methano-1,11α,16RS-trihydroxyprost-13E-en-9-one and 16,18-Methano-17,20-methano-1,11α,16RS-trihydroxyprosta-10,13E-dien-9-one (TR 4799 and TR 4805)

A solution of bicyclo[3.2.0]hept-2-en-6-one, prepared as described in Example 11, was substituted for the bicyclo[4.2.0]oct-2-en-7-one of Example 12 to prepare bicyclo[3.2.0]heptan-6-one. The bicyclo[3.2.0]heptan-6-one had the following spectral characteristics: nmr (CDCl$_3$) δ 1.0–3.8 ppm(m); ir (CHCl$_3$) 905, 1080, 1220, 1385, 1450, 1770, 2870 and 2950 cm$^{-1}$.

The procedure of Example 1 was followed to obtain the corresponding acetylenic alcohol, corresponding iodovinyl alcohol and corresponding protected iodovinyl alcohol by replacing the 4-methyloct-1-yn-4RS-ol with the acetylenic alcohol, 6-(prop-2-ynyl)bicyclo[3.2.0]heptan-6RS-ol. The acetylenic alcohol had the following spectral characteristics: nmr (CDCl$_3$) δ 1.0–2.2 (11H, m), 2.15 (1H, s) and 2.45 ppm (2H, d, J=2.5 Hz); ir (CHCl$_3$) 910, 1775, 1140, 1265, 1460, 2115 (weak), 2870, 2930 3300, 3200 to 3600 (broad) and 3590 cm$^{-1}$.

The 6-(3-iodoprop-2E-enyl)bicyclo[3.2.0]heptan-6RS-ol had the following spectral characteristics: nmr (CDCl$_3$) δ 1.0–2.0 (10H, m), 2.30 (2H, d, J=6.5 Hz), 2.4 (1H, broad s), 6.13 (1H, d, J14 Hz) and 6.63 ppm (1H, d of t, J14, 7 Hz); ir (CHCl$_3$) 950, 1070, 1200, 1260, 1605, 2850, 2940, 3200–3600 (broad) and 3600 cm$^{-1}$.

The 6-(3-iodoprop-2E-enyl)-6RS-(tetrahydropyranyloxy)bicyclo[3.2.0]heptane had the following spectral characteristics: nmr (CDCl$_3$) δ 1.0–2.7 (18H, m), 3.2–4.2 (2H, m), 4.58 (1H, broad s), 6.02 (1H, d, J=14 Hz) and 6.2–6.9 ppm (1H, m); ir (CHCl$_3$) 865, 970, 1010, 1070, 1120, 1180, 1270, 1430, 1610, 2850, and 2940 cm$^{-1}$.

The synthesis of the PGE$_1$ analogue was carried out as described in Example 1. A small amount of the PGA$_1$ prostaglandin analogue was produced as a sideproduct. The prostaglandin analogues had the following spectral characteristics:

TR 4799—[α]$_D$−52.8° (c 1.0, CHCl$_3$); R$_f$(system II) 0.26; nmr (CDCl$_3$) 1.0–3.0 (31H, m), 3.65 (2H, t, J=6.0 Hz), 4.01 (1H, m) and 5.60 ppm (2H, m); ir (CHCl$_3$) 900, 970, 1070, 1260, 1740, 2860, 2930, and 3200–3600 cm$^{-1}$;

ms (70 eV) m/e 364 (p), 346 (p—H$_2$O), 328, 278, 260, 236, 217.

TR 4805—[α]$_D$+77.8° (c 1.0, CHCl$_3$); R$_f$(system II) 0.55; mnr (CDCl$_3$) δ 1.1–2.8 (27H, m), 3.29 (1H, m), 3.66 (2H, t, J=6.0 Hz), 4.06 (1H, m), 5.61 (2H, m), 6.17 (1H, m) and 7.49 ppm (1H, m); ir (CHCl$_3$) 910, 970, 1060, 1245, 1350, 1705, 2860, 2930, and 3200–3600 cm$^{-1}$; ms (70 eV) m/e 346 (p), 278, 260, 236, 217.

Example 14

16,20-Methano-17,20-methano-1,11α,16RS-trihydroxyprost-13E-en-9-one (TR 4903)

The procedures of Example 1 were followed to obtain the corresponding acetylenic alcohol, corresponding iodovinyl alcohol and corresponding protected iodovinyl alcohol by replacing the 2-hexanone with commercially available bicyclo[2.2.1]heptan-2-one.

The acetylenic alcohol had the following spectral characteristics; nmr (CDCl$_3$) δ 1.0–2.8 (10H, m), 2.03 (1H, t, J=2.2 Hz) and 2.42 ppm (2H, d, J=2.2 Hz); ir (CHCl$_3$) 995, 1035, 1160, 1270, 1735, 2950, 3300 and 3200–3600 cm$^{-1}$ (broad).

The 2-(2-iodoprop-2E-enyl)bicyclo[2.2.1]heptan 2RS-ol had the following spectral characteristics: nmr (CDCl$_3$) δ 0.8–2.6 (13H, m), 6.07 (1H, d, J=14.5 Hz) and 6.60 ppm (1H, d of t, J=14.5, 7 Hz); ir (CHCl$_3$) 950, 1030, 1180, 1205, 1305, 2950 and 3300–3700 cm$^{-1}$ (broad).

The 2-(3-iodoprop-2E enyl)-2RS-(tetrahydropyranyloxy)bicyclo[2.2.1]heptane had the following spectral characteristics: nmr (CDCl$_3$) δ 0.8–2.6 (18H, m), 3.2–42 (2H, m), 4.65 (1H, broad s), 6.0 (1H, d, J=14.5 Hz) and 6.1–6.9 ppm (1H, m); ir (CHCl$_3$) 860, 970, 1020, 1070, 1120 and 2940 cm$^{-1}$.

The synthesis of the PGE$_1$ analogue was carried out as described in Example 1. The prostaglandin analogue had the following spectral characteristics:

TR 4903—[α]$_D$—43.4° (c 1.07, CHCl$_3$); R$_f$(system II) 0.25; nmr (CDCl$_3$) δ 0.8–3.0 (31H, m), 3.65 (2H, t, J=5.8 Hz), 4.0 (1H, m) and 5.6 ppm (2H, m); ir (CHCl$_3$) 900, 970, 1070, 1155, 1260, 1740, 2930 and 3200–3600; ms (70 eV) m/e 346 (p—H$_2$O).

Example 15

17,20-Methano-17-methyl-1,11α,16R and S-trihydroxyprost-13E-en-9-one (TR 4982 and TR 4983)

The procedures of Example 3 were followed to obtain 1-methyl-1-cyclopentane carboxaldehyde by replacing 2-methylpropionic acid with commercially available cyclopentanecarboxylic acid and further replacing n-propyliodide with commercially available methyliodide. The procedures of Example 1 were then followed to obtain the corresponding acetylenic alcohol, corresponding iodovinyl alcohol and corresponding protected iodovinyl alcohol by replacing the 2-hexanone with 1-methyl-1-cyclopentanecarboxaldehyde.

The 1-methyl-1-cyclopentanecarboxylic acid had the following spectral characteristics: nmr (CDCl$_3$) δ 1.27 (3H, s), 1.0–2.5 (8H, m) and 11.2 ppm (1H, s); ir (CHCl$_3$) 940, 1200, 1280, 1410, 1455, 1700 and 2400–3400 cm$^{-1}$ (broad).

The intermediate 1-methyl-1-cyclopentanemethanol had the following spectral characteristics: nmr (CDCl$_3$) δ 1.0 (3H, s), 1.0–2.0 (8H, m), 2.42 (1H, broad s) and 3.38 ppm (2H, broad s).

The 1-methyl-1-cyclopentanecarboxaldehyde had the following spectral characteristics: nmr (CDCl$_3$) δ 1.12 (3H, s), 1.0–2.2 (8H, m) and 9.50 ppm (1H, s).

The acetylenic alcohol had the following spectral characteristics: nmr (CDCl$_3$) δ 0.93 (3H, s), 1.0–2.5 (11H, m), 3.0 (1H, broad s) and 3.6 ppm (1H, m); ir (CHCl$_3$) 840, 1060, 1200, 1380, 1450, 1660, 2950, 3300 and 3300–3650 cm$^{-1}$.

The 4-(1-methylcyclopentyl)-1-iodobut-1E-en-4RS-ol had the following spectral characteristics: nmr (CDCl$_3$) δ 0.93 (3H, s), 1.0–2.4 (11H, m), 3.43 (1H, m), 6.12 (1H, d, J=14.5 Hz) and 6.70 ppm (1H, d of t, J=14.5, 7.2 Hz); ir (CHCl$_3$) 945, 1060, 1270, 1380, 1450, 2960 and 3300–3600 cm$^{-1}$.

The 4-(1-methylcyclopentyl)-1-iodo-4RS-(2-ethoxyethoxy)but-1R-ene had the following spectral characteristics: nmr (CDCl$_3$) δ 0.90 (3H, s), 1.0–2.0 (14H, m), 2.30 (2H, t, J=6.2 Hz), 3.2–3.9 (3H, m), 4.75 (1H, m), 6.10 (1H, d, J=14.5 Hz) and 6.3–7.1 ppm (1H, m); ir (CHCl$_3$) 950, 1050, 1090, 1120, 1380, 1450 and 2950 cm$^{-1}$.

The synthesis of the PGE$_1$ analogue was carried out as described in Example 1. The prostaglandin analogue isomers were separated by column chromatography and had the following spectral characteristics:

TR 4983—More Polar Isomer—[α]$_D$—57.7° (c 1.0, CHCl$_3$); R$_f$(system II) 0.31; nmr (CDCl$_3$) δ 0.93 (3H, s), 1.0–3.0 (29H, m), 3.2–4.3 (4H, m) and 5.51 ppm (2H, m); ir (CHCl$_3$) 970, 1070, 1160, 1230, 1740, 2930 and 3200–3650 cm$^{-1}$; ms (70 eV) m/e 348 (p—H$_2$O).

TR 4982—Less Polar Isomer—[α]$_D$—42.5° (c 1.0, CHCl$_3$); R$_f$(system II) 0.33; nmr, ir and ms essentially the same as TR 4983 above.

Example 16

17,17-Propano-1,11α,16R-trihydroxyprost-13E-en-9-one and 17,17-Propano-1,11α,16S-trihydroxyprost-13E-en-9-one (TR 4984 and TR 4985)

The procedures of Example 3 were followed to obtain 1-propyl-1-cyclobutanecarboxaldehyde by replacing 2-methylpropionic acid with commercially available cyclobutanecarboxylic acid. The procedures of Example 1 were then followed to obtain the corresponding acetylenic alcohol, corresponding iodovinyl alcohol and corresponding protected iodovinyl alcohol by replacing the 2-hexanone with 1-propyl-1-cyclobutanecarboxaldehyde.

The 1-propyl-1-cyclobutanecarboxylic acid had the following spectral characteristics: nmr (CDCl$_3$) δ 0.7–2.8 (13H, complex m) and 11.2 ppm (1H, s); ir (CHCl$_3$) 930, 1160, 1230, 1255, 1300, 1330, 1410, 1695 and 2400–3500 cm$^1$.

The intermediate 1-propyl-1-cyclobutane-methanol had the following spectral characteristics: nmr (CDCl$_3$) δ 0.7–2.2 (14H, m) and 3.52 ppm (2H, s); ir (CHCl$_3$) 1005, 1230, 1380, 1460, 2930 and 3200–3600 cm$^{-1}$.

The 1-propyl-1-cyclobutanecarboxaldehyde had the following spectral characteristics: nmr (CDCl$_3$) δ 0.8–2.6 (13H, m) and 9.60 (1H, s); ir (CHCl$_3$) 1150, 1190, 1460, 1695 and 2970 cm$^{-1}$.

The acetylenic alcohol had the following spectral characteristics: nmr (CDCl$_3$) δ 0.8–2.7 (16H, m) and 3.77 ppm (1H, m); ir (CHCl$_3$) 1060, 1220, 1460, 2450, 3300 and 3300–3650 cm$^{-1}$.

The 4-(1-propylcyclobutyl)-1-iodubut-1E-en-4RS-ol had the following spectral characteristics: nmr (CDCl$_3$) δ 0.8–2.5 (16H, m), 3.62 (1H, m), 6.13, (1H, d, J14.5 Hz)

and 6.67 ppm (1H, d of t, J14.5, 7.3 Hz); ir (CHCl$_3$) 940, 1050, 1230, 1270, 1460, 2950 and 3300–3650 cm$^{-1}$.

The 4-(1-propylcyclobutyl)-1-iodo-4RS-(2-ethoxyethoxy)but-1E-ene had the following spectral characteristics: nmr (CDCl$_3$) δ 0.8–2.3 (21H, m), 3.6 (3H, m), 4.7 (1H, m), 6.05 (1H, d, J=14.5 Hz) and 6.6 ppm (1H, d of t, J=14.5, 7.3 Hz); ir (CHCl$_3$) 950, 1020, 1050, 1090, 115, 1380 and 2940 cm$^{-1}$.

The synthesis of the PGE$_1$ analogue was carried out as described in Example 1. The prostaglandin analogue isomers were separated by column chromatography and had the following spectral characteristics:

TR 4985—Polar Isomer—[α]$_D$−56.3° (c 1.04, CHCl$_3$); R$_f$ (system II) 0.34; nmr (CDCl$_3$) δ 0.8–2.7 (34H, m), 3.4–4.3 (4H, m) and 5.57 ppm (2H, m); ir (CHCl$_3$) 960, 1060, 1150, 1210, 1460, 1740, 2930 and 3200–3600 cm$^{-1}$; ms (70 eV) m/e 362 (p—H$_2$O).

TR 4984—Less Polar Isomer—[α]$_D$−39.5° (c 0.98, CHCl$_3$); R$_f$ (system II) 0.35; nmr, ir and ms essentially the same as TR 4985 above.

As referred to earlier, the Searle and Lederle prior art discloses 16-hydroxy compounds which are acids and esters. The methyl ester analogues of the carbinols of Examples 1 (TR 4698); Example 2 (TR 4706); Example 3 (TR 4752) and Example 4 (TR 4749) were prepared in order that biological activities of the methyl esters and the carbinols of the present invention could be compared.

COMPARATIVE PROCEDURE A

Methyl 11α,16RS-dihydroxy-16-methyl-9-oxoprost-13E-oate (TR 4704)

The methyl ester were prepared as described in Example 1 by replacing 4R-(tetrahydropyran-2-yloxy)-2-[7-(tetrahydropyran-2-yloxy)heptyl]2-cyclopenten-1-one with 4R-(tetrahydropyran-2-yloxy)-2-(6-carbomethoxyhexyl)cyclopent-2-en-1-one was prepared as described by Sih et al., *J. Amer. Chem. Soc.*, 97, 865.

The PGE$_1$ ester analogue had the following spectral characteristics: [α]$_D$−71.8° (c 1.0, CHCl$_3$); R$_f$ (system II) 0.41; nmr (CDCl$_3$) δ 0.93 (3H, m), 1.0–2.8 (24H, m), 1.18 (3H, s), 3.47 (2H, broad s), 3.72 (3H, s), 4.07 (1H, m) and 5.66 ppm (2H, m); ir (CHCl$_3$) 900, 970, 1075, 1160, 1230, 1380, 1440, 1730, 2860, 2930, and 3200–3600 cm$^{-1}$; ms (70 eV) m/e 367 (p—CH$_3$), 364 (p—H$_2$O), 351, 346, 333, 325, 315, 306.

COMPARATIVE PROCEDURE B

Methyl 11α,16RS-dihydroxy-9-oxoprost-13E-en-1-oate (TR 4705)

The methyl ester was prepared as described in Example 2 by replacing 4R-(tetrahydropyran-2-yloxy)-2-[7-(tetrahydropyran-2-yloxy)heptyl]2-cyclopenten-1-one with the cyclopentanone ester prepared as described by Sih et al., Comparative Procedure A.

The PGE$_1$ methyl ester analogue had the following spectral characteristics: [α]$_D$−62.2° (c 1.0, CHCl$_3$); R$_f$ (system II) 0.43; nmr (CDCl$_3$) δ 0.95 (3H, m), 1.0–2.8 (26H, m), 3.73 (3H, s), 3.89 (2H, broad s), 4.15 (2H, m), and 5.67 ppm (2H, m); ir (CHCl$_3$) 900, 970, 1080, 1170, 1250, 1340, 1440, 1730, 2860, 2970 and 3200-3600 cm$^{-1}$; ms (70 eV) m/e 350 (p—H$_2$O), 319 (p—H$_2$O—CH$_3$O), 301, 282, 279, 264, 232, 222, 210, 204.

COMPARATIVE PROCEDURE C

Methyl 11α,16R and S-dihydroxy-17,17-dimethyl-9-oxoprost-13E-en-1-oate (TR 4836)

The methyl ester was prepared as described in Example 3 by replacing 4R-(tetrahydropyran-2-yloxy)-2-[7-(tetrahydropyran-2-yloxy)heptyl]2-cyclopenten-1-one with the cyclopentanone ester prepared as described by Sih et al., Comparative Procedure A.

The PGE$_1$ methyl ester analogue had the following spectral characteristics:

TR 4836—More Polar Isomer—[α]$_D$−59.1° (c 1.12, CHCl$_3$); R$_f$ (system II) 0.49; nmr (CDCl$_3$) δ 0.90 (9H, broad s), 1.0–3.1 (22H, m), 3.1–4.2 (4H, m), 3.67 (3H, s) and 5.52 ppm (2H, m); ir (CHCl$_3$) 870, 970, 1075, 1170, 1220, 1370, 1445, 1730, 2860, 2930 and 3200–3600 cm$^{-1}$; ms (70 eV) m/e 378 (p—H$_2$O), 365, 360, 347, 329, 311, 293, 282, 264, 262, 232, 222, 210, 204, 200.

TR 4835—Less Polar Isomer—[α]$_D$−54.9° (c 0.69, CHCl$_3$); R$_f$ (system II) 0.54; nmr, ir and ms essentially the same as isomeric TR 4836, ie, more polar isomer above.

COMPARATIVE PROCEDURE D

Methyl 11α,16RS-dihydroxy-17-methyl-9-oxoprost-13E-oate (TR 4814)

The methyl ester was prepared as described in Example 4 by replacing 4R-(tetrahydropyran-2-yloxy)-2-[7-(tetrahydropyran-2-yloxy)heptyl]2-cyclopenten-1-one with the cyclopentanone ester prepared as described in Sih et al., Comparative Procedure A.

The PGE$_1$ methyl ester analogue had the following spectral characteristics: [α]$_D$−65.0° (c 0.98, CHCl$_3$); R$_f$ (system II) 0.49; nmr (CDCl$_3$) δ 0.90 (6H, m), 1.0–3.1 (23H, m), 3.57 (2H, broad s), 3.66 (3H, s), 4.10 (2H, m) and 5.54 ppm (2H, m); ir (CHCl$_3$) 970, 1070. 1160, 1230, 1370, 1440, 1735, 2860, 2940 and 3200–3600 cm$^{-1}$; ms (70 eV) m/e 382 (p), 364, 351, 346, 333, 315, 311, 282, 264, 232, 222, 210, 204, 200.

Compounds of this invention were screened to detect the following biological activities:

BIOLOGICAL ACTIVITIES (A) effects on the rat stomach, rat colon, chick rectum, and rabbit aorta in vitro (cascade assay);

(B) effect on the rat uterus in vitro;

(C) effect on the guinea pig trachea in vitro;

(D) antagonism of the effects of PGE$_1$ and PGF$_{2\alpha}$ on the guinea pig ileum in vitro;

(E) effect on human platelet aggregation in vitro; and (F) effect on gastric secretion in the rat.

In addition, certain of the compounds were tested for the following biological activities;

(G) effect on blood pressure and heart rate in the anesthetized cat;

(H) effect on femoral blood flow in the anesthetized dog; and (I) effect on systolic blood pressure in the hypertensive rat.

A. Evaluation of Cascade Assay Effects

The smooth muscle stimulant effects of the test compounds were determined simultaneously in four different tissues that are known to be reactive to naturally occurring prostaglandins. Segments of rat stomach fundus, rat colon, chick rectum and rabbit aortic strip were obtained as described by: Vane, J. R., *Brit. J. Pharmacol.*, 12: 344 (1957); Regoli, D. and Vane, J. R., *Brit. J. Pharmacol.*, 23: 351 (1964); Mann, M. and West, G. B., *Brit J. Pharmacol.*, 5: 173 (1950); and Furchgott, R. F. and Bhadrakom, R., *J. Pharmacol. Exper. Ther.*, 108: 129 (1953). One end of each preparation was tied to the bottom of a 10 ml tissue chamber and the other to a force displacement transducer (Grass FT-03) for continuous tension recording. The stomach, colon, and rectum segments are stretched to an initial tension of 1 g, while the aortic strip was subjected to 4 g. All preparations were left undisturbed for 1 hour prior to ptesting. The chambers were equipped with an external jacket through which water, maintained at 40° C., was circulated. Preparations were arranged one beneath the other in descending order (aorta, stomach, colon and rectum). Provision was made for bathing the four tissues successively so that they were superfused with the same fluid (Gaddum, J. H., *Brit. J. Pharmacol.*, 6: 321 [1953]). The bathing fluid consisted of: Krebs bicarbonate solution aerated with a mixture of 95% $O_2$ and 5% $CO_2$ and warmed at 37° C.; atropine sulphate (0.1 mcg/ml), phenoxybenzamine hydrochloride (0.1 mcg/ml), propranolol hydrochloride (3.0 mcb/ml), methysergide maleate (0.2 mcb/ml) and brompheniramine maleate (0.1 mcg/ml) were added to eliminate the possibility of smooth muscle responses being due to stimulation of cholinergic, adrenergic, serotonin or histamine receptors. The fluid was circulated by means of a roller pump and was allowed to drip over the preparations at a rate of 10 ml/minute.

Test compounds were diluted from stock solutions so as to administer quantities ranging from 0.0001 to 100,000 ng in a volume of 0.5 ml. The compounds were applied by dripping on the uppermost tissue, at intervals of 10 to 20 minutes. Maximal increases in tension after each dose were measured and the results were used to plot dose-response curves. $ED_{50}$ data (doses necessary to produce a response 50% of maximum) were then calculated graphically for each tissue. Maximum responses utilized were those elicited by $PGE_1$ in gastric and rectal tissue, by $PGF_{2\alpha}$ in colonic tissue, and by $PGA_2$ in aortic tissue.

Activity in each tissue was scored according to the following scale:

| $ED_{50}$, ng | Activity Value |
|---|---|
| >10000 | 0 |
| 1001–10000 | 1 |
| 101–1000 | 2 |
| 10–100 | 3 |
| <10 | 4 |

B. Evaluation of the Effects on the Rat Uterus in Vitro

The uterine stimulant effect of test compounds was determined in segments of uterus obtained from rats (140–160 g) pretreated subcutaneously with 1 mg/kg of diethylstilbesterol 18 hours before the experiment. The tissues were placed in 10 ml chambers filled with de-Jalon solution at 29° C., were aerated and bubbled with 95% $O_2$ and 5% $CO_2$, and were prepared for isometric recording with force displacement transducers. Preparations were stretched to an initial tension of 1 g and were left undisturbed for 30 minutes. Carbachol (1 mcg/ml) was then added to the bath and a response was recorded. After a ten minute interval the carbachol procedure was repeated. Responses to increasing concentrations of a test compound (0.001 to 10 mcg/ml with one log intervals) were then recorded every 10 minutes. Preparations were washed four times after each response. All doses of compounds were administered in a 0.1 ml volume. Because it has been observed that the magnitude of the second response to carbachol (approximately 10% greater than the first) is close to the maximal response of the tissue, such value was taken as a measure of the sensitivity of a particular segment. Responses to each concentration of the test compound were expressed in terms of percentage of the second response to carbachol and the $ED_{50}$ (dose producing a response 50% that of carbachol) was calculated graphically. Activity was scored according to the following scale:

| $ED_{50}$ (mcg/ml) | Activity Value |
|---|---|
| >10 | 0 |
| 1.001–10 | 1 |
| 0.101–1.0 | 2 |
| 0.01–0.1 | 3 |
| <0.01 | 4 |

C. Evaluation of the Effects on the Guinea Pig Trachea in Vitro

A male guinea pig weighing 200–500 g was killed by a blow on the head. A 20 mm length of the trachea was dissected from the animal, transferred to a petri dish containing Krebs' solution (aerated with 95% $O_2$ and 5% $CO_2$ at 37° C.), and cut longitudinally opposite the tracheal muscle. The tissue was then cut transversely three quarters of the distance across, a second cut in the opposite direction (again three quarters of the distance across the tissue) was made and the procedure was continued for the whole tissue. The ends of the trachea were pulled to form a zig-zig shaped strip. The tracheal strip used in the experiment was approximately 30 mm when extended under 0.25–0.5 g load in the tissue bath. Cotton thread was tied to one end of the tissue, and linen thread to the other. It was attached via the linen thread to a glass hook in a 5 ml isolated tissue bath containing Krebs' solution (37° C., aerated with a mixture of 95% $O_2$ and 5% $CO_2$). The opposite end was attached via cotton to an isotonic Harvard transducer (Model 386 Heart/Smooth Muscle Transducer, Harvard Apparatus). The load on the transducer lever was small, usually 0.3 g, with a range of 0.25–0.5 g, and the magnification high, 80 fold using an appropriate twin-channel pen recorder. A minimum of thirty minutes was allowed before applying a test compound to the tissue. Test compounds were then applied (in volumes of 0.5 ml) at thirty minute intervals, being in contact with the tissue for five minutes followed by an overflow washout time of twenty seconds.

Prostaglandin $E_1$, at a bath concentration of 0.1 mcg/ml, was then tested repeatedly on two such strips, obtained from two different animals, until two responses (the values of which are recorded) differing by no more than 25% occur. A test compound was then added to the same two strips at bath concentrations of 0.01, 0.1, 1.0, and 10.0 mcg/ml and the effects of the compound were recorded. After the test compound had been evaluated at the highest concentration, $PGE_1$ was retested at 0.1 mcg/ml (and the value of the response recorded) to insure that the viability of the strips was retained during the experiment. The mean of the effects of the test compound on the two strips was then calculated for each concentration, and, based on the resulting values, an activity value was assigned as follows:

| Response | Activity Value |
| --- | --- |
| More relaxation at 0.01 mcg/ml than that elicited by $PGE_1$ | R4 |
| More relaxation at 0.1 mcg/ml than that elicited by $PGE_1$ | R3 |
| More relaxation at 1.0 mcg/ml than that elicited by $PGE_1$ | R2 |
| More relaxation at 10.0 mcg/ml than that elicited by $PGE_1$ | R1 |
| No effect at any concentration greater than that elicited by $PGE_1$ | 0 |
| More contraction at 10.0 mcg/ml than the degree of relaxation elicited by $PGE_1$ | C1 |
| More contraction at 1.0 mcg/ml than the degree of relaxation elicited by $PGE_1$ | C2 |
| More contraction at 0.1 mcg/ml than the degree of relaxation elicited by $PGE_1$ | C3 |
| More contraction at 0.01 mcg/ml than the degree of relaxation elicited by $PGE_1$ | C4 |

D. Evaluation of Antagonistic Effects on the Guinea Pig Ileum in Vitro

The degree and specificity of antagonism of test compounds to the smooth muscle stimulant effects of prostaglandins were assessed in segments of terminal guinea pig ileum. Preparations were placed in tissue chambers filled with Ringer-Tyrode solution at 37° C., bubbled with a mixture of 95% $O_2$ and 5% $CO_2$, and arranged for isometric recording with force displacement transducers. The segments were stretched to an initial tension of 1 g, and responses to a test concentration of acetylcholine (0.1 mcg/ml) were obtained every 5 minutes until two similar responses were observed (usually after four administrations). Responses to acetycholine (0.1 mcg/ml), $PGE_1$ (0.1 mcg/ml), $BaCl_2$ (100 mcg/ml) and $PGF_{2\alpha}$ (1 mcg/ml) were obtained (and recorded) in that order at 5 minute intervals before and after 100 seconds of incubation with 0.1 and 1.0 mcg/ml of the test compound. Any direct contractile effect of the test compound was recorded and evaluated in terms of mean values in grams of tension developed at each concentration. Responses to the different agonists observed after incubation with the test compound were expressed as percent of control responses. All drugs were administered in a volume of 0.1 ml.

Antagonism to prostaglandins was scored independently for $PGE_1$ and $PGF_{2\alpha}$ according to the following criteria:

| Response | Activity Value |
| --- | --- |
| Less than 50% blockade of PG responses | 0 |
| More than 50% blockade of PG responses and more than 10% antagonism of Ach and/or $BaCl_2$, or production of direct contraction | 1 |
| More than 50% blockage of PG responses at 1 mcg/ml with less than 11% antagonism of Ach and $BaCl_2$ without production of direct contraction | 2 |

E. Evaluation of Inhibition of Human Platelet Aggregation

The ability of test compounds to inhibit platelet aggregation was determined by a modification of the turbidometric technique of Born, G. V. R. (Nature, 194: 927 [1962]). Blood was collected from human volunteers, who had not ingested aspirin or aspirin-containing products within the preceding two weeks, in heparinized containers and was allowed to settle for one hour. The platelet rich plasma (prp) supernates were collected and pooled. Siliconized glassware was used throughout.

In a representative assay, 1.9 ml of PRP and 0.2 ml of test compound at the appropriate concentration (0.001 to 100 mc/gm), or 0.2 ml of distilled water (control procedure) were placed in sample cuvettes. The cuvettes were placed in a 37° C. incubation block for 15 minutes, and then in a spectrophotometer linked to a strip chart recorder. After 30–60 seconds, 0.2 ml of a solution, prepared by diluting a calf-skin collagen solution 1:9 with Tyrodes' Solution, was added to each cuvette. Platelet aggregation was evidenced by a decrease in optical density.

Calculation of the degree of inhibition of platelet aggregation exhibited by each concentration of test compound was accomplished according to the method of Caprino et al., (Arzneim-Forsch., 23: 1277 [1973]). An $ED_{50}$ value was then determined graphically. Activity of the compounds was scored as follows:

| $ED_{50}$ (mcg/kg) | Activity Value |
| --- | --- |
| >1.0 | 0 |
| >0.1 and <1.0 | 1 |
| >0.01 and <0.1 | 2 |
| >0.001 and <0.01 | 3 |
| <0.001 | 4 |

F. Evaluation of the Effects on Gastric Secretion in the Rat

A procedure based on that described by Lipman, W. (J. Pharm. Pharmacol., 210 335 [1968]) was used to assess the influence of test compounds on gastric secretion. Rats of one sex weighing 150 to 200 g were randomly divided into groups of six animals each and fasted for 48 hours previous to the experiments, water being available ad libitum. The animals were anesthetized with ether, the abdomen opened through a midline incision, and the pylorus ligated. Test compounds were diluted from stock solution so as to administer a dose of 1.5 mg/kg in a volume equivalent to 1 ml/kg. Subcutaneous injections were applied immediately after surgery and again 2 hours later, so that a total dose of 3.0 mg/kg was administered. Dilutions were made with phosphate buffer (pH 7.38) as recommended by Lee et al. (Prostaglandins, 3: 29 [1973]) in order to insure adequate stability of drugs at the subcutaneous depot. Each compound was tested in one group of rats; an additional control group received only the vehicle.

Four hours after pyllric ligation the animals were killed with ether, the cardias ligated, and the stomachs removed. The volume of gastric secretion was measured and the contents centrifuged at 5000 rpm for 10 minutes. Total acid in the supernatant was titrated against a 0.1N sodium hydroxide solution and the amount expressed in mEq.

Volume and total acid values of the treated group were compared with those of the controls of the t-test. Anti-secretory activity was scored according to the following scale:

| % decrease in acidity | Activity Value |
|---|---|
| <26 | 0 |
| 26–50, not significant | 1 |
| 26–50, significant | 2 |
| 51–75 | 3 |
| 76–100 | 4 |

G. Evaluation of the Effects on Blood Pressure and Heart Rate in the Anesthetized Cat The acute effects of test compounds on blood pressure and heart rate were determined in cats of either sex anesthetized with a mixture of pentobarbital sodium (35 mg/kg, i.v.) and barbital sodium (100 mg/kg, i.v.). Cannulas were placed in the trachea to allow adequate spontaneous ventilation, in a femoral artery for blood pressure recording with a strain gage transducer, and in a saphenous vein for drug administration. Heart rate was recorded by means of a cardiotachometer driven by the R wave of the electrocardiogram. After a period of 10 minutes of stable recordings of blood pressure and heart rate, the test compound was administered intravenously at doses increasing from 0.01 to 10.0 mcg/kg, spaced one log and injected at 10 minute intervals. All doses were injected in a volume of 0.1 ml/kg. Modifications of blood pressure and heart rate induced by the test compound were expressed both in absolute units (mmHg and beats/minute) and as percent of values recorded immediately before administration of each dose. Biphasic responses were tabulated in the order in which they occurred. The direction of the observed changes is also noted (+ for increases, and − for decreases).

Activity of compounds in this test was judged only on the basis of the degree of hypotension observed. Thus, the $ED_{50}$ mmHg (dose decreasing blood pressure by 50 mmHg) was calculated graphically, and the compound scored according to the following scale:

| $ED_{50}$ mmHg, mcg/kg | Activity Value |
|---|---|
| >10.0 | 0 |
| 1.01–10.0 | 1 |
| 0.11–1.0 | 2 |
| 0.01–0.1 | 3 |
| <0.01 | 4 |

H. Evaluation of Effects on Femoral Blood Flow in the Anesthetized Dog

The peripheral vasodilator or constrictor effects of test compounds were determined in mongrel dogs of either sex, weighing between 10 and 20 kg, anesthetized intravenously with 35 mg/kg of pentobarbital sodium. An external iliac artery was dissected immediately above the femoral arch for a length of approximately 5 cm, and a previously calibarated, non-cannulating electromagnetic-flowmeter sensor with a lumen between 2.5 and 3.5 mm was placed snugly around the vessel. Cannulas were placed in a branch of the artery arising distally to the location of the flowmeter sensor for intraarterial drug administrations, in the contralateral femoral artery for systemic blood pressure recording, and in the trachea for artificial respiration with room air. Femoral blood flow and systemic blood pressure were continuously recorded with an electromagnetic flowmeter and pressure transducer, respectively.

After an adequate control period, test compounds were injected intraarterially at one log-spaced doses ranging from 0.001 to 10 mcg, in a volume of 0.5 ml and at 5 to 10 minute intervals. Maximum changes in blood flow, as well as any variations in blood pressure, were tabulated for each dose in absolute values (ml/min. and mmHg), and the former were also expressed in percent. Those calculations were made taking as control values those existing immediately before administration of each dose. The direction of the observed change (+ for increase and − for decrease) was also noted. The dose changing blood flow by 100 ml/min ($ED_{100}$ ml/min) was calculated graphically and was used for scoring activity as follows:

| $ED_{100}$ ml/min. mcg | Activity Value |
|---|---|
| >10.0 | 0 |
| 1.01–10.0 | 1 |
| 0.11–1.0 | 2 |
| 0.0–0.1 | 3 |
| <0.01 | 4 |

I. Evaluation of the Effects on Blood Pressure in the Hypertensive Rat

The acute anithypertensive activity of test compounds was determined in rats made hypertensive by the procedure of Grollman (*Proc. Soc. Exper Biol. Med.*, 57: 102 [1944]). Female rats weighing between 60 and 100 g were anesthetized with ether, the right kidney approached through a flank retroperitoneal incision, decapsulated and tied with a figure-of-eight-ligature. The animals were left to recover and two weeks later were again anesthetized and the contralateral kidney removed. Four weeks after the second operation the rats were subjected to indirect blood pressure measurements and those showing systolic pressure values greater than 160 mmHg were selected for drug testing.

Blood pressure was measured in the tail with an inflatable occluding cuff placed at the base of the extremity and a pulse detector located distally. The cuff was inflated to approximattely 300 mmHg and was slowly deflated until pulsations appeared, indicating the level of systolic pressure; diastolic pressure was not recorded by this procedure. All measurements were carried out in unanesthetized, unsedated animals maintained in a warm environment during the recording procedure and for at least 6 hours before. In all cases, three pressure readings were obtained in succession and mean values were calculated thereof.

Experiments were carried out in groups of five hypertensive rats in which systolic pressure was determined immediately before and 2, 4, 6 and 9 hours after intraperiotoneal administration of the test compound at a dose of 1 mg/kg. Drugs were diluted from stock solutions with phosphate buffer (Lee et. al., *Prostaglandins,* 29 [1973]), so as to inject this quantity in a volume of 1 ml/kg. Changes from control blood pressure values were calculated for each interval both in mmHg and in percent, and evaluated for significance by means of Wilcoxon's signed rank test (Wilcoxon, R. and Wilcox, R. A., "Some Rapid Approximate Statistical Procedures", Lederle Laboratories, Pearl River [1964]). Activity of the compound was scored as follows:

biological activity, in comparison with the corresponding acid and ester analogues.

TABLE G

| Example No. | TR Number | Cascade | | | Rat Uterus | Guinea Pig Trachea | Feline Blood Pressure, Heart Rate | Femoral Blood Flow | Blood Pressure Hypertensive Rat | Gastric Secretion | Antagonism | | Platelet Aggregation |
|---|---|---|---|---|---|---|---|---|---|---|---|---|---|
| | | Stomache | Colon | Rectum | Aorta | | | | | | | PGE1 | PGF2A | |
| 1 | 4698 | 0 | 1 | 1 | 0 | — | R4 | 0 | 0 | 1 | 4 | 0 | 0 | +0 |
| Comp. A | 4704 | 2 | 1 | 2 | 0 | — | R3 | 2 | 3 | 0 | 4 | 0 | 0 | +0 |
| 2 | 4706 | 1 | 1 | 1 | 0 | — | R2 | 0 | 0 | 0 | 4 | 1 | 1 | +0 |
| Comp. B | 4705 | 2 | 1 | 2 | 0 | — | R2 | 0 | 1 | 0 | 4 | 1 | 1 | +0 |
| 3 | 4752 | 0 | 0 | 0 | 0 | 0 | R4 | 0 | 0 | 0 | 0 | 0 | 0 | +0 |
| Comp. C | 4836 | 0 | 0 | 0 | 0 | 0 | R4 | — | — | — | 4 | 0 | 0 | +1 |
| 4 | 4749 | 0 | 0 | 0 | 0 | 0 | R2 | 0 | 0 | 0 | 3 | 0 | 0 | +0 |
| Comp. D | 4814 | 0 | 0 | 0 | 0 | 0 | R4 | 0 | 2 | 1 | 4 | 0 | 0 | +0 |

| Blood pressure decrease | Activity Value |
|---|---|
| Not significant at any time interval | 0 |
| Significant at one time interval | 1 |
| Significant at two time intervals | 2 |

As earlier discussed, the Searle prior art discloses the methyl ester analogous to presently claimed TR 4698 and TR 4706. Searle contains no experimental data or examples to support the alleged utility of inhibition of gastric secretion without the "undesirable side-affects displayed by related substances." The acid and ester analogues are further alleged to be inhibitors of blood platelet aggregation and to display anti-fertility and bronchodilating properties.

The Lederle prior art discloses the methyl ester of presently claimed TR 4752 and TR 4749. Lederle alleges utility of the acid and ester analogues as agents for the "treatment of gastric hypersecretion and gastric erosia" and as bronchodilators. Anti-ulcer, gastric antisecretory and bronchodilator properties are given for 16-hydroxy acid analogues, 9-oxo-10-hydroxy-13-prostanoic acid and 9-oxo-16-hydroxy-13-trans-prostanoic acid.

The experimental test data summarized in Table G demonstrates the nonobviousness of the claimed alkyl-substituted PGE$_1$ carbinol analogues over the Searle and Lederle ester and acid analogues. Examples 1–4 demonstrate that the alkyl-substituted carbinols of the present invention have a unexpected clean separation of The gastric antisecretory (GAS) and guinea pig trachea values for TR 4698 and its methyl ester analogue TR 4704 are the same. However, the feline blood pressure and heart rate, femoral blood flow and cascade values are significantly and undesirably higher for the methyl ester analogue. The carbinol analogue shows a significantly cleaner separation of biological activity, that is, a greater reduction of undesirable side-effects then the methyl ester analogue.

Similarly, the GAS and guinea pig trachea values for TR 4706 and its methyl ester analogue TR 4705 are the same. The femoral blood flow for the TR 4705 analogue is slightly higher than the TR 4706 value; the stomache and colon values for the cascade are higher for the TR 4705 in comparison to TR 4706, indicating that TR 4706 shows a significantly cleaner separation of biological activity.

The biological activity of TR 4752 and its methyl ester analogue TR 4836 are similar. However, TR 4752 shows no GAS activity, indicating usefulness of TR 4752 for a single indication, tracheal relaxation.

The GAS and guinea pig trachea values for TR 4749 are both lower than the values for its methyl ester analogue. The femoral blood flow and hypertensive rat blood pressure are both higher for the methyl ester than the carbinol, indicating that TR 4749 shows a significantly cleaner separation of biological activity.

Experimental test data values, for the compounds of Examples 5–16 are located in Table H.

TABLE H

| Example No. | TR Number | Cascade | | | | Rat Uterus | Guinea Pig Trachea | Feline Blood Pressure, Heart Rate | Femoral Blood Flow | Blood Pressure Hypertensive Rat | Gastric Secretion | Antagonism | | Platelet Aggregation |
|---|---|---|---|---|---|---|---|---|---|---|---|---|---|---|
| | | Stomache | Colon | Rectum | Aorta | | | | | | | PGE1 | PGF2A | |
| 5 | 4840 | 0 | 0 | 0 | 0 | 0 | R0 | — | — | — | 0 | 0 | 0 | +1 |
| | 4848 | 0 | 0 | 0 | 0 | 0 | R1 | — | — | — | 0 | 0 | 0 | +1 |
| 6 | 4844 | 0 | 0 | 0 | 0 | 0 | C0 | — | — | — | 0 | 0 | 0 | +1 |
| | 4846 | 0 | 0 | 0 | 0 | 0 | R0 | — | — | — | 1 | 0 | 0 | +1 |
| 7 | 4703 | 0 | 0 | 0 | 0 | 0 | R2 | 0 | 0 | 0 | 0 | 0 | 0 | +1 |
| 8 | 4753 | 0 | 0 | 0 | 0 | 0 | R2 | — | — | — | 0 | 0 | 1 | +1 |
| 9 | 4851 | 0 | 0 | 1 | 0 | 0 | R3 | 0 | — | 0 | 0 | 0 | 0 | +1 |
| 10 | 4770 | 0 | 0 | 1 | 0 | 0 | R3 | 0 | 0 | — | 3 | 0 | 0 | +1 |
| 11 | 4803 | 0 | 0 | 0 | 0 | 0 | R4 | — | — | — | 1 | 0 | 0 | +1 |
| 12 | 4804 | 0 | 0 | 0 | 0 | 0 | R0 | — | — | — | 0 | 1 | 1 | +1 |
| | 4806 | 0 | 0 | 0 | 0 | 0 | C0 | — | — | — | 0 | 0 | 0 | +1 |
| 13 | 4799 | 0 | 0 | 0 | 0 | — | R4 | — | — | 0 | 0 | 0 | 0 | — |
| | 4805 | 0 | 0 | 0 | 0 | 0 | R0 | — | — | — | 0 | 0 | 0 | +1 |
| 14 | 4903 | 0 | 0 | 0 | 0 | 0 | R3 | — | — | — | 2 | 0 | 0 | +1 |
| 15 | 4982 | — | — | — | — | — | R1 | — | — | — | 1 | — | — | +1 |
| | 4983 | — | — | — | — | — | R2 | — | — | — | 1 | — | — | +1 |
| 16 | 4984 | 0 | 0 | 0 | — | — | R0 | — | — | — | 0 | — | — | +1 |

TABLE H-continued

| Example No. | TR Number | Cascade Stomache | Colon | Rectum | Aorta | Rat Uterus | Guinea Pig Trachea | Feline Blood Pressure, Heart Rate | Femoral Blood Flow | Blood Pressure Hypertensive Rat | Gastric Secretion | Antagonism PGE1 | PGF2A | Platelet Aggregation |
|---|---|---|---|---|---|---|---|---|---|---|---|---|---|---|
| | 4985 | 0 | 0 | 0 | — | — | R1 | — | — | — | 0 | — | — | +1 |

The following ester prostaglandin analogues, containing a cycloalkyl, bicycloalkyl or bicycloalkenyl moiety, were prepared as described below.

Example 17

Methyl 15R,19-cyclo-11α,16-trans-dihydroxy-20-nor-9-oxoprost-13E-en-1-oate and Methyl 15S,19-cyclo-11α,16-trans-dihydroxy-20-nor-9-oxoprost-13E-en-1-oate (TR 4838 and TR 4839)

A. Preparation of Iodovinyl Alcohol

A solution of 4.0 g of commercially available cyclopentene oxide and 30 ml of hexamethylphosphoramide (HMPA) was stirred under argon at 25°. Commercially available lithium acetylide ethylene diamine complex (5.6 g) was added and the reaction mixture heated at 80° for two hours. The reaction mixture was cooled to 0° and 20 percent aqueous ammonium chloride added. The mixture was extracted with ether. The extracts were washed with 10 percent HCl, water (five times), saturated aqueous NaHCO$_3$ and brine, then dried, filtered, and distilled using aspirator vacuum to yield 2.15 g trans-2-ethynylcyclopentan-1RS-ol, bp 72°. The product had the following spectral characteristics: nmr (CDCl$_3$) δ 1.0 to 3.0 (9H, m) and 4.25 ppm (1H, m); ir (CHCl$_3$) 860, 900, 995, 1080, 1215, 1450, 2110, 2860, 2960, 3300, 3200–3600 (broad) and 3600 cm$^{-1}$.

The trans-2-ethynylpentan-1RS-ol was converted to the corresponding iodovinyalcohol, trans-2-(2E-iodoethenyl)cyclopentan-1RS-ol as described below.

A 130 ml portion (150 mmol) of a solution of (1.15M) diisobutylaluminum hydride in dry toluene was stirred under argon with ice water bath cooling as a second solution of 5.24 g (52.4 mmol) of the trans-2-enthynyl-cyclopentan-1RS-ol, in 10 ml of dry toluene was added dropwise over a period of one hour. Stirring was then continued without cooling for one hour and then with oil bath warming (60° C.) for three hours. The oil bath was then replaced with a dry ice-acetone (−78° C.) bath as a third solution of 26.8 g (105 mmol) of iodine in dry tetrahydrofuran to total 100 ml was added dropwise to the reaction mixture maintaining a stirring of the reaction mixture. The cooling bath was then removed and the reaction mixture was allowed to come to 20° slowly before it was quenched by being forced under a slight argon pressure through polyethylene tubing into a vigorously stirred mixture of ether and two percent aqueous sulfuric acid. The ether phase was removed and then washed successively with another portion of two percent sulfuric acid, brine, saturated aqueous sodium bicarbonate and brine. It was dried over Na$_2$SO$_4$ and evaporated under reduced pressure. The residue (6.36 g) was distilled at high vacuum to remove the most volatile contaminants. The iodovinyalcohol remained undistilled at 560 and was used as is.

The iodovinyl alcohol had the following spectral characteristics: nmr (CDCl$_3$) δ 0.8–2.7 (8H, m), 3.85 (1H, broad m), 6.10 (1H, d, J=41 Hz) and 6.50 (1H, d of d, J=14, 7 Hz); ir (CHCl$_3$) 870, 910, 860, 1040, 1080, 2870, 2940, 3200–3600 (broad) and 3580 cm$^{-1}$.

B. Preparation of Organolithiocuprate from Iodovinylalcohol (1) Preparation of trans-2-(2E-iodoethenyl)-1RS-(tetrahydropyranyloxy)-cyclopentane The hydroxyl function of the above iodovinyalcohol was protected as described below.

A mixture of 4.8 g (2.02 mmol) of trans-2-(2E-iodoethenyl)cyclopentan-1RS-ol 3.7 ml dihyropyran and a 20 mg portion of toluenesulfonic acid in 1.5 ml of dry ether was stirred in a flask under argon. After 18 hours, the product solution was washed with aqueous NaHCO$_3$ solution. The wash solution was back-extracted with ether and the extracts combined. The combined extract was dried (Na$_2$SO$_4$) and evaporated in vacuo to yield 7.2 g of residue which was chromatographed on silica gel 60 using chloroform elution. The yield of pure protected iodovinyalcohol was 3.2 g. The iodovinyl alcohol had the following spectral characteristics: nmr (CDCl$_3$) δ 0.8–2.3 (13H, m) 3.2–4.2 (3H, m), 4.65 (1H, broad s), and 5.9 to 6.8 ppm (2H, m); ir (CHCl$_3$) 865, 910, 975, 1030, 1075, 1130, 2880 and 2960 cm$^{-1}$.

(2) Preparation of Organolithiocuprate from Protected Iodovinylalcohol

A solution of 0.715 g (2.2 mmol) of trans-2-(2E-iodoethyl)-1RS-(tetrahydropyranyloxy)cycloptentane in 12 ml of dry ether was stirred in a flash under argon with −78° bath cooling as 4.2 ml (4.4 mmol) of a 1.1M solution of t-butyllithium in pentane was added, dropwise via syringe. The resultant solution was left to stir at −78° for two hours.

A second solution was prepared by stirring under argon a suspension of 0.275 g (2.1 mmol) of dry copper (I) pentyne in 5.1 ml of dry ether solubilized with 0.84 ml of hexamethylphosphorous triamide, until it became homogeneous. This first solution was then transferred via polyethylene tubing to the above coper(I)pentyne solution as it was stirred with −78° bath cooling. The desired lithiocuprate reagent, an orange mixture, was stirred 30 minutes after addition was complete.

C. Substituted 2-Cyclopenten-1-one 4R-(tetrahydropyran-2-yloxy)-2-(6-carbomethoxyhexyl)cyclopent-2-en-1-one was prepared as described by C. J. Sih et al., *J. Amer. Chem. Soc.*, 97, 865 (1975).

D. Prostaglandin Synthesis

The synthesis of the prostaglandin E$_1$ analogue was achieved as described below.

A solution of 0.650 g of the above substituted cyclopent-2-en-1-one in 7.6 ml of dry ether was added dropwise to the lithiocuprate reaction mixture as stirring was continued at −78°. After addition was complete, the resultant orange mixture was stirred for 30 minutes at −78° then at −20° for 1.5 hours, and then at 0° for 1.5 hours.

The reaction was quenched by addition of 20 percent aqueous ammonium sulfate and the aqueous layer extracted with ether. The combined organic layers were washed with 2 percent aqueous sulfuric acid and filtered through celite. The filtrate was washed with saturated aqueous sodium bicarbonate and brine, then dried (MgSO4), filtered and evaporated in vacuo to yield 1.1 g of residue containing the tetrahydropyran-protected form of TR 4838.

This residue was dissolved in 50 ml of acetic acid-water-tetrahydrofuran (65:35:10) and left to stand under argon for 18 hours at room temperature and the resultant solution evaporated in vacuo to remove the solvent. The residue was dissolved in ethyl acetate and washed with saturated aqueous sodium bicarbonate. The wash solution was back extracted with ethyl acetate. The combined extract was dried over MgSO4 and evaporated in vacuo to yield 525 mg of a yellow residue. This residue was chromatographed on silicic acid-diatomaceous earth (85:15) using benzene-ethyl acetate.

Chromatography of the crude product yielded: Methyl 15R, 19-cyclo-11α, 16-trans-dihydroxy-20-nor-9-oxoprost-13E-en-1-oate and Methyl 15S 19-cyclo-11α, 16-trans-dihydroxy-20-9-oxoprost-13E-en-1-oate PGE$_1$ analogues having the following spectral characteristics:

More Polar Isomer (TR 4839)—$[\alpha]_D$−83.1° (c 1.02, CHCl$_3$); R$_f$ (system II) 0.31; nmr (CDCl$_3$) 1.0–3.0 (24H, m), 3.67 (3H, s), 3.5–4.2 (4H, m), and 5.43 ppm (2H, m); ir (CHCl$_3$) 910, 970, 1090, 1180, 1230, 1370, 1450, 1740, 2860, 2930 and 3100–3600 cm$^{-1}$; ms (70 eV) m/e 352 (p), 334, 316, 306, 302.

Less Polar Isomer (TR 4838)—$[\alpha]_D$−36.5° (c 0.88, CHCl$_3$); R$_f$(system II) 0.37; nmr, ir and ms were much the same as those for the polar isomer above.

Example 18

Methyl 15R,20-cyclo-11α,16-trans-dihydro-9-oxoprost-13E-en-1-oate and

Methyl 15S,20-cyclo-11α,16-trans-dihydro-9-oxoprost-13E-en-1-oate (TR 4767 and TR 4768)

The cyclopentene oxide of Example 17 was replaced with commercially available cyclohexane oxide. The procedure of Example 17 was followed to convert the cyclohexene oxide into the corresponding acetylenic alcohol, (I)-trans-2-ethynylcyclohexanol. The acetylenic alcohol had the following spectral characteristics: nmr (CDCl$_3$) δ 0.8–2.5 (10H, m), 2.58 (1H, broad s) and 3.55 (1H, broad m); ir (CHCl$_3$) 840, 1010, 1070, 1110, 1270, 1450, 2110, 2860, 2950, 3300, 3200–3600 (broad) and 3575 cm$^{-1}$.

The acetylenic alcohol was converted into the corresponding iodovinyl alcohol and the protected iodovinyl alcohol as described in Example 15. The (±)-trans-2-ethynylcyclopentene of Example 15 was replaced with (±)-trans-2-ethynylcyclohexanol; the following change was made in the procedure. When the iodine solution was added to the reaction mixture, it was added only until color persisted for one minute or more. Product isolation proceeded as in Example 1. The iodovinyl alcohol, (±)-trans-2-(2E-iodoethenyl)cyclohexanol had the following spectral characteristics: nmr (CDCl$_3$) 0.8–2.3 (10H, m), 3.3 (1H, broad m), 6.13 (1H, d, J=14 Hz) and 6.50 Hz (1H, d of d, J=14 Hz).

The tetrahydropyranyloxy-protected iodovinyl alcohol, (±)-trans-2-(2E-iodoethenyl)-1RS-(tetrahydropyranyloxy)cyclohexane, had the following spectral characteristics: nmr (CDCl$_3$) δ 0.8–2.2 (15H, m), 3.2–4.2 (3H, m), 4.5 (1H, broad s), 6.02 (1H, d, J=14 Hz) and 6.53 ppm (1H, d of t, J=14, 7 Hz); ir (CHCl$_3$) 860, 900, 980, 1020, 1075, 1120, 1360, 1450, 1610, 2850, and 2950 cm$^{-1}$.

The synthesis of the PGE$_1$ methyl ester analogues was carried out as described in Example 17. Chromatography of the the crude product yielded isomers, methyl 15R and S, 20-cyclo-11α, 16R and S dihydroxy-9-oxoprost-13E-en-1-oate. The physical characteristics of the isomers were:

More Polar Isomer (TR 4768)—$[\alpha]_D$−81.5° (c 0.72, CHCl$_3$); R$_f$ (system II) 0.25; nmr (CDCl$_3$) δ 0.8–3.0 (25H, m), 3.0–4.2 (4H, m), 3.63 (3H, s) and 5.40 ppm (2H, m); ir (CHCl$_3$) 900, 970, 1090, 1160, 1240, 1740, 2860, 2940 and 3100–3600 cm$^{-1}$; ms (70 eV) m/e 366 (p), 348, 330.

Less Polar Isomer (TR 4767)—$[\alpha]_D$+3.3° (c 1.0, CHCl$_3$); R$_f$ (system II) 0.32; nmr, ir and ms similar to those of the polar isomer above.

Example 19

Methyl 11α,16RS-dihydroxy-16,20-methano-9-oxoprost-13E-en-1-oate (TR 4717)

A 12.2 g portion of magnesium turnings was heat dried under argon in a 500 ml flask fitted with an air stirrer, condensor and addition funnel. After cooling the flask, 60 ml of dry ether was added, followed by a small portion of a solution of 33.9 ml of propargyl bromide in 60 ml of dry ether followed by 50 mg of mercuric chloride. After spontaneous ether reflux indicated that the reaction had commenced, the remainder of the propargyl bromide solution was added dropwise to the mixture to maintain gentle reflux. After the addition was complete, the reaction mixture was stirred for an additional one-half hour. A solution of 27 g of cyclohexanone, commercially available, in 25 ml of dry ether was then added to the reaction mixture, again at a rate to maintain gentle reflux. A heated oil bath was then used to reflux the final mixture for another hour. The final mixture was then quenched by the addition of water, followed by 10 percent hydrochloric acid to dissolve solid salts. The phases were separated and the ether extract was washed with brine and saturated sodium bicarbonate solution. It was then dried over MgSO$_4$ and then distilled using a water pump to successively remove ether and a trace of cyclohexanone (bp ca 50°). The 1-(prop-2-ynyl)cyclohexanol (bp 91°–94°) had the following spectral characteristics: nmr (CDCl$_3$) δ 1.0–2.0 (10H, m), 2.0–2.2 (2H, m) and 2.39 ppm (2H, m); ir (CHCl$_3$) 870, 980, 1060, 1150, 1270, 1450, 1220 (weak), 2860, 2930, 3300, 3200–3600 (broad) and 3570 cm$^{-1}$.

The 1-(prop-2-ynyl)cyclohexanol was converted to the corresponding idovinylalcohol, 1-(3-iodoprop-2E-enyl)cyclohexanol as described below.

A solution of 30 ml (169 mmol) of diisobutylaluminum hydride in 75 ml of dry toluene was stirred under argon with ice water bath cooling as a second solution of 7.0 g (50 mmol) of the 1-(prop-2-ynyl)cyclohexanol, in 25 ml of dry toluene was added dropwise over a period of one hour. Stirring was then continued without cooling for one hour and then with oil bath warming (50°-60° C.) for three hours. The oil bath was then replaced with a dry ice-acetone (−78° C.) bath as a third solution of 42.8 g (169 mmol) of iodine in dry tetrahydrofuran to total 100 ml was added dropwise to the reaction mixture maintaining a stirring of the reaction mixture. The cooling bath was then removed and the reaction mixture was allowed to come to 20° slowly before it was quenched by being forced under a slight argon pressure through polyethylene tubing into a vigorously stirred mixture of ether and two percent aqueous sulfuric acid. The ether phase was removed and then washed successively with another portion of two percent sulfuric acid, brine, saturated aqueous sodium bicarbonate and brine. It was dried over $Na_2SO_4$ and evaporated under reduced pressure. The residue (10.3 g) was chromatographed on silica gel to yield 0.54 g of the pure iodovinyl alcohol.

The iodovinyl alcohol had the following spectral characteristics: bp 83–85° (0.1) nmr ($CDCl_3$) δ 1.0–1.8 (11H, m), 2.22 (2H, d, J=6 Hz), 6.16 (1H, d, J=14 Hz) and 6.76 ppm (1H, d of t, J=14, 7 Hz); ir ($CHCl_3$) 905, 950, 1140, 1455, 1610, 2870, 2950, 3200–3600 (broad) and 3600 $cm^{-1}$.

Because of the low yield, an alternate procedure was used to prepare additional iodovinyl alcohol compound (as the hydroxyl-protected form).

A solution of 2.9 g (21 mmol) of 1RS-(prop-2-ynyl)-cyclohexanol in 10 ml of dry ether was stirred under argon as 0.24 ml (26 mmol) of dihydropyran was added followed by a small scoop (ca. 5 mg) of toluenesulfonic acid. After one hour tlc ($CHCl_3$, silica gel) analysis indicated that significant starting material remained so another 0.2 ml of dihydropyran and a small scoop of toluenesulfonic acid were added. Twice more at one hour intervals 0.2 ml portions of dihydropyran and a trace of toluenesulfonic acid were added to the reaction mixture. It was finally left to stir under argon at room temperature for 15 hours. Potassium carbonate was then added to the mixture and it was stirred for several minutes before it was washed with water. The wash solution was back extracted with ether and the combined extracts were then washed with brine, dried ($Na_2SO_4$) and evaporated in vacuo to yield 4.6 g of 1-(tetrahydropyran-2-yloxy)-1-(prop-2-ynyl)cyclohexane having the following spectral characteristics: nmr ($CDCl_3$) δ 1.0–2.5 (19H, m), 3.6 (2H, broad m) and 4.65 ppm (1H, broad s); ir ($CHCl_3$) 980, 1030, 1050, 1070, 1120, 1150, 1270, 1450, 2120, (weak), 2760, 2930, and 3300 $cm^{-1}$.

The alternate procedure was carried out as described below.

A 200 ml portion of 1M borane in tetrahydrofuran was stirred under argon with −10° bath cooing in a flask fitted with a dry ice condensor. A total of 46 ml (400 mmol) of 2-methyl-2-butene was then added slowly via syringe below the surface of the borane solution. The reaction mixture was then stirred one hour at 0° and then left overnight in a refrigerator.

A 10 ml portion of the above disiamylborane solution was stirred under argon with ice bath cooling as 2.4 g of 1-(tetrahydropyran-2-yloxy)-1-(prop-2-ynyl)cyclohexane was added slowly. The resultant solution was stirred at room temperature for two hours. Tlc ($CHCl_3$, silica gel) showed that the reaction was not complete. A second 10 ml portion of disiamylborane solution was added to the reaction mixture. After another 1.5 hours the reaction was quenched by the addition of 3.3 g of trimethylamine oxide dihydrate portionwise over 30 minutes. The resultant mixture was stirred (still at 0°) for one hour. A 33 ml portion of 1M aqueous sodium hydroxide was then added quickly followed by a solution of 7.6 g of iodine in 40 ml of dry tetrahydrofuran. The resultant mixtue was stirred one hour without a cooling bath and then poured into 100 ml of water. Sodium thiosulfate was then added until the color of excess iodine had dissipated. The resultant mixture was extracted with ether. The extract was washed with water and then brine. It was evaporated in vacuo to yield 9.00 of residue. This residue was dissolved in methanol and benzene which were then removed by evaporation in vacuo to yield 5.0 g of residue. This residue was chromatographed on silica gel using chloroform elution to yield 2.4 g of pure 1-(3-iodoprop-2E-enyl)-1-(tetrahydropyranyloxy)cyclohexane. The spectral properties of this material were identical to those of the material prepared by the earlier procedure.

The methods described in Example 17 were used to prepare TR 4717 by replacing trans-2-(2E-iodoethyl)-1RS-(tetrahydropyran-2-yloxy)cyclopentane with 1-(3-iodoprop-2E-enyl)-1-(tetrahydropyran-2-yloxy)cyclohexane.

The resulting PGE$_1$ analogue TR 4717 had the following spectral characteristics:

$[α]_D$ −68.4° (c 1.0, $CHCl_3$); $R_f$ (system II) 0.47; nmr ($CDCl_3$) δ 1.0–3.0 (29H, m), 3.56 (2H, broad s), 3.70 (3H, s), 4.08 (1H, m) and 5.63 (2H, m); ir ($CHCl_3$) 885, 970, 1080, 1170, 1245, 1360, 1425, 1740, 2860, 2930 and 3200–3600 $cm^{-1}$; ms (70 eV) m/e 368, 362, 344, 312, 282, 264, 232, 204.

Example 20

Methyl 11α,16RS-dihydroxy-16,18-methano-17, 20-methano-9-oxoprosta-13E, 19-dien-1-oate and Methyl 16RS-hydroxy-16,18-methano-17,20-methano-9-oxoprosta-10,13E,19-trien-1-oate (TR 4800 and TR 4802)

The method described in Example 19 was used to prepare TR 4800 and 4802 by replacing the cyclohexanone with bicyclo[3.2.0]hept-2-en-6-one. The bicyclo starting material was produced as described in *Tetrahedron Letters* 307 (1970).

The procedure of Example 19 was followed to obtain the corresponding acetylenic alcohol, the corresponding iodovinyl alcohol and the corresponding protected iodovinyl alcohol.

The acetylenic alcohol had the following spectral characteristics: nmr ($CDCl_3$) δ 1.5–3.2 (10H, m) and 5.83 (2H, m); ir ($CHCl_3$) 690, 930, 1170, 1260, 1350, 1415, 2120 (weak), 2850, 2930, 3300, 3200–3600 (broad) and 3570 $cm^{-1}$.

The 6-(3-iodoprop-2E-enyl)bicyclo[3.2.0]hept-2-en-6RS-ol had the following spectral characteristics: nmr ($CHCl_3$) δ 1.5–3.2 (9H, m), 5.82 (2H, m), 6.10 (1H, d, J=14 Hz) and 6.59 ppm (1H, d of t, J=14, 7 Hz).

The 6-(3-iodoprop-2E-enyl)-6RS-(tetrahydropyranyloxy)bicyclo[3.2.0]hept-2-ene had the following spectral characteristics: nmr ($CDCl_3$) δ 1.2–3.0 (14H, m), 3.2–4.2 (2H, m), 4.60 (1H, broad s), 5.77 (2H, broad s), 6.08 (1H, d, J=14 Hz) and 6.60 ppm (1H, d of t, J=14, 7 Hz); ir ($CHCl_3$) 870, 910, 990, 1030, 1075, 1130, 1610, 2860, and 2950 $cm^{-1}$.

The synthesis of the PGE$_1$ analogue (Tr 4800) was carried out as described in Example 19. A small amount of PGA$_1$ prostaglandin analogue (TR 4802) was produced as a side-product. The prostaglandin analogues had the following spectral characteristics:

TR 4800—$[\alpha]_D$—56.1° (c 1.0 CHCl$_3$); R$_f$(system II) 0.39; nmr (CDCl$_3$) δ 1.0–3.2 (26H, m), 3.66 (3H, s), 4.0 (1H, m), and 5.4–6.0 ppm (4H, m); ir (CHCl$_3$) 970, 1070, 1160, 1240, 1350, 1440, 1730, 2860, 2740 and 3200–3600 cm$^{-1}$; ms (70 eV) m/e 390 (p), 372, 358, 340, 324, 306, 292, 274, 232.

TR 4802—$[\alpha]_D$+67.4° (c 1.0, CHCl$_3$); R$_f$(system II) 0.62; nmr (CDCl$_3$) δ 1.0–3.2 (22H, m), 3.23 (1H, m), 3.64 (3H, s), 5.59 (2H, m), 5.81 (2H, m), 6.14 (1H, m) and 7.48 ppm (1H, m); ir (CHCl$_3$) 970, 1030, 1070, 1170, 1220, 1350, 1440, 1710, 2860, 2930 and 3200–3600 cm$^{-1}$; ms (70 eV) m/e 372 (p), 340, 323, 306, 274, 232.

Example 21

Methyl 11α,16RS-dihydroxy-17,20-ethano-16,18-methano-9-oxoprost-13E-en-1-oate and Methyl 17,20-ethano-16RS-hydroxy-16,18-methano-9-oxoprosta-10,13E-dien-1-oate (TR 4808 and TR 4807)

A solution of bicyclo[4.2.0]octan-7-one was substituted for the cyclohexanone of Example 19. The bicyclo[4.2.0]octan-7-one was prepared from bicyclo[4.2.0]oct-2-en-7-one. The bicyclo[4.2.0]oct-2-en-7-one was prepared as described in *Tetrahedron Letters* 4753 (1971).

The bicyclo[4.2.0]oct-2-en-7-one had the following spectral characteristics: nmr (CDCl$_3$) 1.5–2.5 (8H, m), 2.03 (1H, t, J=2.5 Hz) 2.35 (1H, s) 2.55 (2H, d, J=2.5 Hz) and 5.72 ppm (2H, m); ir (CHCl$_3$) 880, 1000, 1120, 1270, 1445, 2130 (weak), 2850, 2950, 3310, 3200–3600 (broad) and 3570 cm$^{-1}$.

The bicyclo[4.2.0]oct-2-en-7-one compound was converted into bicyclo[4.2.0]octan-7-one as follows.

A solution of 4.2 g of bicyclo[4.2.0]oct-2-en-7-one in isopropanol, total solution of 100 ml, was hydrogenated over 0.5 g of platinum oxide at 50 PSI of hydrogen in a Parr shaker for 18 hours. The catalyst was removed by filtration and the filtrate was evaporated to yield 3.2 g of the compound, having the following spectral characteristics: nmr 0.8 to 3.5 ppm (m); ir 1040, 1090, 1450, 1765, 2860 and 2930 cm$^{-1}$.

The procedure of Example 19 was followed to obtain the corresponding acetylenic alcohol, the corresponding iodovinyl alcohol and the corresponding protected iodovinyl alcohol by replacing cyclohexanone with bicyclo[4.2.0]octan-7-one. The 7-(prop-2-ynyl)bicyclo[4.2.0]octa-7RS-ol had the following spectral characteristics: nmr (CDCl$_3$) δ 1.0–2.2 (13H, m), 2.28 (1H, s) and 2.47 ppm (2H, d, J=2.5 Hz); ir (CHCl$_3$) 900, 1070, 1140, 1260, 1460, 2120 (weak), 2860, 2930, 3300, 3200 to 3600 (broad) and 3570 cm$^{-1}$.

The 7-(3-iodoprop-2E-enyl)bicyclo[4.2.0]octan-7RS-ol had the following spectral characteristics: nmr (CDCl$_3$) δ 1.0–2.2 (13H, m), 2.37 (2H, d, J=6 Hz), 6.10 (1H, d, J=14 Hz) and 6.72 ppm (1H, d of t, J=14, 7 Hz); ir (CHCl$_3$) 905, 950, 1075, 1100, 1130, 1260, 1455, 1610, 2850, 2930, 3200–3600 (broad) and 3600 cm$^{-1}$.

The iodovinyl alcohol was protected to yield 7-(3-iodoprop-2E-enyl)-7RS-(tetrahydropyranyloxy)bicyclo[4.2.0]octane having the following spectral characteristics: nmr (CDCl$_3$) δ 0.8–2.6 (20H, m), 3.2–4.2 (2H, m), 4.57 (1H, broad s), 6.02 (1H, d, J=14 Hz) and 6.3–6.9 (1H, m); ir (CHCl$_3$) 870, 945, 975, 1020, 1070, 1120, 1270, 1450, 2850 and 2940 cm$^{-1}$.

The synthesis of the PGE$_1$ analogue (TR 4808) was carried out as described in Example 15. A small amount of the PGA$_1$ prostaglandin analogue (TR 4807) was produced as a side-product. The prostaglandin analogues had the following spectral characteristics:

TR 4808—$[\alpha]_D$—56.3° (c 1.0, CHCl$_3$); R$_f$(system II) 0.42; nmr (CDCl$_3$) δ 1.0–3.0 (30H, m), 3,39 (2H, broad s), 3.65 (3H, s), 4.04 (1H, m) and 5.60 ppm (2H, m); ir (CHCl$_3$) 970, 1010, 1070, 1165, 1260, 1445, 1730, 2860, 2930 and 3200–3600 cm$^{-1}$; ms (70 eV) m/e 406 (p), 388, 357, 339, 324, 306, 274, 264, 232.

TR 4807—$[\alpha]_D$+71.1° (c 1.0, CHCl$_3$); R$_f$(system II) 0.57; nmr (CDCl$_3$) δ 1.0–2.6 (28H, m), 3.26 (1H, m), 3.64 (3H, s), 5.58 (2H, m), 6.11 (1H, m) and 7.47 ppm (1H, m); ir (CHCl$_3$) 970, 1070, 1220, 1370, 1440, 1710, 2860, 2930 and 3200–3600 cm$^{-1}$; ms (70 eV) m/e 388 (p), 356, 339, 306, 274, 232, 204.

Example 22

Methyl 11α,16RS-dihydroxy-16,18-methano-17,20-methano-9-oxoprost-13E-en-1-oate and Methyl 16RS-hydroxy-16,18-methano-17,20-methano-9-oxoprosta-10,13E-dien-1-oate (TR 4809 and TR 4801)

The method described in Example 21 was used to prepare bicyclo[3.2.0]heptan-6-one by replacing the bicyclo[4.2.0]oct-2-en-7-one with bicyclo[3.2.0]hept-2-en-6-one. The bicyclo compound was produced as described by E. J. Corey and T. Ravindranathan, *Tetrahedron Letters* 4753 (1971).

The bicyclo[3.2.0]hept-2-en-6-one had the following spectral characteristics: nmr (CDCl$_3$) δ 2.2–4.2 ppm (6H, m) and 5.83 ppm (2H, m); ir (CHCl$_3$) 1080, 1150, 1345, 1775, 2860 and 2920 cm$^{-1}$.

The bicyclo[3.2.0]heptan-6-one had the following spectral characteristics: nmr (CDCl$_3$) δ 1.0–3.8 ppm (m); ir (CHCl$_3$) 905, 1080, 1220, 1385, 1450, 1770, 2870 and 2950 cm$^{-1}$.

The procedure of Example 19 was followed to obtain the corresponding acetylenic alcohol, the corresponding iodovinyl alcohol and the corresponding protected iodovinyl alcohol by replacing cyclohexanone with bicyclo[3.2.0]heptan-6-one. The alcohol had the following spectral characteristics: nmr (CDCl$_3$) δ 1.0–2.2 (11H, m), 2.15 (1H, s) and 2.45 ppm (2H, d, J=2.5 Hz); ir (CHCl$_3$) 910, 1775, 1140, 1265, 1460, 2115 (weak), 2870, 2930, 3300, 3200 to 3600 (broad) and 3590 cm$^{-1}$.

The 6-(3-iodoprop-2E-enyl)bicyclo[3.2.0]heptan-6RS-ol had the following spectral characteristics: nmr (CDCl$_3$) δ 1.0–2.0 (10H, m), 2.30 (2H, d, J=6.5 Hz), 2.4 (1H, broad s), 6.13 (1H, d, J=14 Hz) and 6.63 ppm (1H, d of t, J=14, 7 Hz); ir (CHCl$_3$) 950, 1070, 1200, 1260, 1605, 2850, 2940, 3200–3600 (broad) and 3600 cm$^{-1}$.

The iodovinyl alcohol was protected to yield 6-(3-iodoprop-2E-enyl)-6RS-(tetrahydropyranyloxy)bicyclo[3.2.0]-heptane having the following spectral characteristics: nmr (CDCl$_3$) δ 1.0–2.7 (18H, m), 3.2–4.2 (2H, m), 4.58 (1H, broad s), 6..02 (1H, d, J=14 Hz) and 6.2–6.9 ppm (1H, m); ir (CHCl$_3$) 865, 970, 1010, 1070, 1120, 1180, 1270, 1430, 1610, 2850 and 2940 cm$^{-1}$.

The synthesis of the PGE$_1$ analogue (TR 4809) was carried out as described in Example 19. A small amount of the PGA$_1$ prostaglandin analogue (TR 4801) was produced as a side-product. The prostaglandin analogues had the following spectral characteristics:

TR 4809—$[\alpha]_D$ −48.3° (c 1.0, CHCl$_3$); R$_f$(system II) 0.44; nmr (CDCl$_3$) δ 1.0–2.8 (30H, m), 3.66 (3H, s), 4.0 (1H, m), and 5.58 ppm (2H, m); ir (CHCl$_3$) 970, 1075, 1160, 1240, 1440, 1740, 2860, 2930, and 3200–3600 cm$^{-1}$; ms (70 eV) m/e 392 (p), 374, 360, 343, 324, 306, 288, 274, 264 232.

TR 4801—$[\alpha]_D$ +71.1° (c 1.0, CHCl$_3$); R$_f$(system II) 0.57; nmr (CDCl$_3$) δ 1.0–2.8 (27H, m), 3.3 (1H, m), 3.67 (3H, s), 5.62 (2H, m), 6.15 (1H, m) and 7.50 ppm (1H, m); ir (CHCl$_3$) 900, 970, 1020, 1070, 1120, 1170, 1210, 1360, 1440, 1710, 2860, 2940 and 3200–3600 cm$^{-1}$; ms (70 eV) m/e 374 (p), 342, 325, 306, 274, 264, 246, 232.

Example 23

Methyl 11α,16RS-dihydroxy-16,20-methano-17,20-methano-9-oxoprost-13E-en-1-oate (TR 4883)

The methods of Example 19 were used to obtain the corresponding acetylenic alcohol, the corresponding iodovinyl alcohol and the corresponding protected iodovinyl alcohol by replacing cyclohexenone with commercial bicyclo[2.2.1]heptan-2-one.

The 2-(prop-2-ynyl)bicyclo[2.2.1]heptan-2RS-ol had the following spectral characteristics: nmr (CDCl$_3$) δ 1.0–2.8 (10H, m), 2.03 (1H, t, J=2.2 Hz) and 2.42 ppm (2H, d, J=2.2 Hz); ir (CHCl$_3$) 995, 1035, 1160, 1270, 1735, 2950, 3300 and 3200–3600 cm$^{-1}$ (broad).

The 2-(3-iodoprop-3E-enyl)bicyclo]2.2.1]heptan-2RS-ol had the following spectral characteristics: nmr (CDCl$_3$) δ 0.8–2.6 (13H, m), 6.07 (1H, d, J=14.5 Hz) and 6.60 ppm (1H, d of t, J=14.5, 7 Hz); ir (CHCl$_3$) 950, 1030, 1180, 1205, 1305, 2950 and 3300–3700 cm$^1$ (broad).

The 2-(3-iodoprop-3E-enyl)-2RS-(tetrahydropyranyloxy)bicyclo[2.2.1]heptane had the following spectral characteristics: nmr (CDCl$_3$) δ 0.8–2.6 (18H, m), 3.2–4.2 (2H, m), 4.65 (1H, broad s), 6.0 (1H, d, J=14.5 Hz) and 6.1–6.9 ppm (1H, m); ir (CHCl$_3$) 860, 970, 1020, 1070, 1120 and 2940 cm$^{-1}$.

The synthesis of the PGE$_1$ analogue was carried out as described in Example 15 by replacing trans-2-(2E-iodoethenyl)-1RS-(tetrahydropyran-2-yloxy)cyclopentane with 2-(3-iodoprop-2E-enyl)-2RS-(tetrahydropyran-2-yloxy)bicyclo[2.2.1]heptane. The prostaglandin analogue TR 4883 had the following spectral characteristics: $[\alpha]_D$ −53.0° (c 0.94, CHCl$_3$); R$_f$(system II) 0.38; nmr (CDCl$_3$) δ 0.8–2.8 (29H, m), 3.63 (3H, s), 4.1 (1H, m) and 3.60 ppm (2H, m); ir (CHCl$_3$) 970, 1070, 1160, 1210, 1440, 1740, 2940 and 3200–3650 cm$^{-1}$; ms (70 eV) m/e 374 (p—H$_2$O).

Example 24

Methyl 11α,16R and S-dihydroxy-17,17-propano-9-oxoprost-13E-ene-1-oate (TR 4978 and 4979)

The methods of Example 25 were followed to obtain the corresponding alkylated acid, the corresponding substituted methanol and the corresponding carboxaldehyde by replacing cyclopentanecarboxylic acid with commercial cyclobutane-carboxylic acid and also replacing methyl iodide with commercial propyl iodide.

The 1-propylcyclobutane-1-carboxylic acid had the following spectral characteristics: nmr (CDCl$_3$) δ 0.7–2.8 (13H, complex m) and 11.2 ppm (1H, s); ir (CHCl$_3$) 930, 1160, 1230, 1255, 1300, 1330, 1410, 1695 and 2400–3500 cm$^{-1}$.

The intermediate 1-propyl-1-cyclobutanemethanol had the following spectral characteristics: nmr (CDCl$_3$) δ 0.8–2.2 (14H, m) and 3.52 ppm (2H, s); ir (CHCl$_3$) 1005, 1230, 1380, 1460, 2930 and 3200–3600 cm$^{-1}$.

The 1-propyl-1-cyclobutanecarboxaldehyde had the following spectral characteristics: nmr (CDCl$_3$) δ 0.8–2.6 (13H, m) and 9.60 (1H, s); ir (CHCl$_3$) 1150, 1190, 1460, 1695 and 2970 cm$^{-1}$.

The methods of Example 17 were then used to obtain the corresponding acetylenic alcohol, the corresponding iodovinyl alcohol and the corresponding protected iodovinyl alcohol by replacing cyclohexanone with 1-propylcyclobutane-1-carboxyaldehyde.

The 5,5-propanooct-1-yn-4RS-ol had the following spectral properties: nmr (CDCl$_3$) δ 0.8–2.7 (16H, m) and 3.77 ppm (1H, m); ir (CHCl$_3$) 1060, 1220, 1460, 2450, 3300 and 3300–3600 cm$^{-1}$.

The 4-(1-propylcyclobutyl)-1-iodobut-1E-en-4RS-ol had the following spectral characteristics: nmr (CDCl$_3$) δ 0.8–2.5 (16H, m), 3.62 (1H, m), 6.13 (1H, d, J=14.5 Hz) and 6.67 ppm (1H, d of t, J=14.5, 7.3 Hz); ir (CHCl$_3$) 940, 1050, 1230, 1270, 1460, 2950 and 3300–3650 cm$^{-1}$.

The 4-(1-propylcyclobutyl)-1-iodo-4RS-(2-ethoxyethoxy)-but-1E-ene had the following spectral characteristics: nmr (CDCl$_3$) δ 0.8–2.3 (21H, m), 3.6 (3H, m), 4.7 (1H, m), 6.05 (1H, d, J=14.5 Hz) and 6.6 ppm (1H, d of t, J=14.5, 7.3 Hz); ir (CHCl$_3$) 950, 1020, 1050, 1090, 1115, 1380 and 2940 cm$^{-1}$.

The synthesis of the PGE$_1$ analogue was carried out as described in Example 15. The prostaglandin analogue isomers were separated by column chromatography and had the following spectral characteristics:

TR 4979—Polar Isomer: $[\alpha]_D$ −56.0° (c 1.01, CHCl$_3$); R$_f$(system II) 0.46; nmr (CDCl$_3$) δ 0.8–2.8 (33H, m), 3.62 (3H, s), 3.3–4.3 (2H, m) and 5.01 ppm (2H, m); ir (CHCl$_3$) 965, 1070, 1160, 1210, 1440, 1740, 2940 and 3200–3650 cm$^{-1}$; ms (70 eV) m/e 390 (p—H$_2$O).

TR 4978—Less Polar Isomer: $[\alpha]_D$ −43.5° (c 1.30, CHCl$_3$); R$_f$(system II) 0.47; nmr, ir and ms essentially the same as for the isomer TR 4979 above.

Example 25

Methyl 11α,16R-dihydroxy-17,20-methano-17-methyl-9-oxoprost-13E-en-1-oate and

Methyl 11α,16S-dihydroxy-17,20-methano-17-methyl-9-oxoprost-13E-en-1-oate (TR 4980 and TR 4981)

A solution of 53 g (0.525 mol) of dry diisopropylamine in 417 ml of dry tetrahydrofuran was stirred under argon with an external −10° bath as 331 ml (0.530 mol) of a solution of n-butyllithium (1.6M) in hexane was added fast dropwise. The resultant solution was stirred with cooling for 15 minutes. A solution of 28.5 g (0.25 mol) of commercial cyclopentanecarboxylic acid in 42 ml of dry tetrahydrofuran was then added dropwise to the stirred, cooled reaction mixture. The resultant solution was then stirred 15 minutes at 0°. A 53.2 g (0.375 mol) portion of commercial methyliodide was then added slowly dropwise to the stirred, cooled reaction mixture. The ice bath was then removed, and the reaction mixture was stirred at room temperature for 2 hours. The resultant solution was quenched by the addition of 10% hydrochloric acid, until an acidic aqueous phase was observed. The phases were separated after addition of ether, and the aqueous phase was back extracted with ether twice. The combined ether extract was washed with brine, dried (MgSO$_4$) and evaporated in vacuo to yield 34.2 g of a red oil. This product was distilled (water pump vacuum) to yield a red purified product, bp 106°–108°. This red oil was dissolved in ether, washed with saturated aqueous sodium thiosulfate solution, dried (MgSO$_4$) and then evaporated in vacuo to yield 20 g of a pale yellow oil. Examination of the methyl ester of this product indicated that it contained considerable starting material, cyclopentanecarboxylic acid along with the desired product. The above procedure was then repeated on the recovered sample with the change of proportionately less reagents for 20 g vs. 28.5 g of starting material, and also the reaction mixture was stirred 18 hours rather than 2 hours after addition of methyliodide. The yield of pure 1-methylcyclopentane-1-carboxylic acid was 18.1 g: colorless oil; bp 115°–116° (20 mm); nmr (CDCl$_3$) δ 1.27 (3H, s), 1.0–2.5 (8H, m) and 11.2 ppm (1H, s); ir (CHCl$_3$) 940, 1200, 1280, 1410, 1455, 1700 and 2400–3400 cm$^{-1}$ (broad).

A slurry of 4.02 g of lithium aluminum hydride in 86 ml of ether was prepared and stirred under argon with cooling at 0° as a solution of 18.1 g of 1-methycyclopentane-1-carboxylic acid in 46 ml of anhydrous ether was added dropwise. The resultant mixture was then refluxed for 45 minutes. It was re-cooled and then quenched by the careful dropwise addition in sequence of 28 ml ethyl acetate, 5.3 ml water, 5.3 ml of 15% NaOH and then 16.1 ml of water. The resultant mixture was filtered and then the resultant removed gelatanous material rinsed with ether several times. The remaining gel was stirred with Celite and acetone and then filtered. The removed solids were then rinsed thoroughly with ether/ethyl acetate (1:1). These second acetone/ether/ethyl acetate extracts were kept separate and evaporated in vacuo. The residue was mixed with ethyl acetate and washed with brine. The remaining organic extract was dried (MgSO$_4$) and evaporated in vacuo. The original ether filtrate was separately evaporated in vacuo. The original ether filtrate yielded 8.74 g of product, 1-methylcyclopentanemethanol, and the acetone treated extract yielded 7.4 g of recovered starting material, 1-methylcyclopentanecarboxylic acid. The product alcohol had the following spectral characteristics: nmr (CDCl$_3$) δ 1.0 (3H, s), 1.0–2.0 (8H, m), 2.42 (1H, broad s) and 3.38 ppm (2H, broad s).

Pyridinium chlorochromate was prepared by following the procedure of E. J. Corey and J. W. Suggs, *Tetrahedron Letters*, 31, 2647 (1975). A solution of 11.8 g of 1-methylcyclopentanemethanol in 32 ml of anhydrous methylene chloride was added to a stirred suspension of 39.2 pyridinium chlorochromate in 312 ml of methylene chloride under argon. The resultant dark mixture was stirred for 1.5 hours at ambient temperature. A portion of ether was added to the resultant mixture and then the supernatant was decanted. The remaining dark residue was rinsed several times with ether. The combined ether solutions were filtered through a short pad of Florisil. The resultant solution was concentrated by distillation of ether and then the residue was distilled at 110 mm Hg to yield 6.41 g of 1-methylcyclopentanecarboxaldehyde as a colorless oil: bp 98°–100°; nmr (CDCl$_3$) δ 1.12 (3H, s), 1.0–2.2 (8H, m) and 9.50 ppm (1H, s).

The methods of Example 17 were used to obtain the corresponding acetylenic alcohol, the corresponding iodovinyl alcohol and the corresponding protected iodovinyl alcohol by replacing cyclohexanone with 1-methylcyclopentanecarboxaldehyde.

The 4-(1-methylcyclopentyl)but-1-yn-4RS-ol had the following spectral characteristics: nmr (CDCl$_3$) δ 0.93 (3H, s), 1.0–2.5 (11H, m), 3.0 (1H, broad s) and 3.6 ppm (1H, m); ir (CHCl$_3$) 840, 1060, 1200, 1380, 1450, 1660, 2950, 3300 and 3300–3650 cm$^{-1}$.

The 4-(1-methylcyclopentyl)-1-iodobut-1E-en-4RS-ol had the following spectral characteristics: nmr (CDCl$_3$) δ 0.93 (3H, s), 1.0–2.4 (11H, m), 3.43 (1H, m), 6.12 (1H, d, J=14.5 Hz) and 6.70 ppm (1H, d of t, J=14.5, 7.2 Hz); ir (CHCl$_3$) 945, 1060, 1270, 1380, 1450, 2960 and 3300–3600 cm$^1$.

The 4-(1-methylcyclopentyl)-1-iodo-4RS-(2-ethoxyethoxy)but-1E-ene had the following spectral characteristics: nmr (CDCl$_3$) δ 0.90 (3H, s), 1.0–2.0 (14H, m), 2.30 (2H, t, J=6.2 Hz), 3.2–3.9 (3H, m), 4.75 (1H, m), 6.10 (1H, d, J=14.5 Hz) and 6.3–7.1 ppm (1H, m); ir (CHCl$_3$) 950, 1050, 1090, 1120, 1380, 1450 and 2950 cm$^{-1}$.

The synthesis of the PGE$_1$ analogue was carried out as described in Example 15 by replacing trans-2-(2E-iodoethanyl)-1RS-(tetrahydropyran-2-yloxy)cyclopentane with 4-(1-methylcyclopentyl)-1-iodo-4RS(2-ethoxyethoxy)but-1E-ene. The prostaglandin analogue isomers TR 4980 and TR 4981 were separated by chromatography and had the following spectral characteristics:

TR 4981—Polar Isomer: [α]$_D$−63.6° (c 0.92, CHCl$_3$); R$_f$(system II) 0.47; nmr (CDCl$_3$) δ 0.97 (3H, s), 1.02–2.8 (28H, m), 3.2–4.3 (2H, m), 3.8 (3H, s) and 5.68 ppm (2H, m); ir (CHCl$_3$) 965, 1070, 1160, 1220, 1440, 1740, 2940 and 3200–3650 cm$^{-1}$; ms (70 eV) m/e 376 (p—H$_2$O).

TR 4980—Less Polar Isomer: [α]$_D$−47.1° (c 0.98, CHCl$_3$); R$_f$ (system II) 0.48; nmr, ir and ms much the same as for the isomer TR 4981.

The experimental test data summarized in Table I indicates that the claimed 16-hydroxy PGE$_1$ ester analogues all have utility as gastric antisecretory agents or bronchodilators. All of the compounds exhibit a desired separation of biological activity, in particular with regard to 0 or low values in the cascade assay tests.

TABLE I

| Example No. | TR Number | Cascade | | | | Rat Uterus | Guinea Pig Trachea | Feline Blood Pressure, Heart Rate | Femoral Blood Flow | Blood Pressure Hypertensive Rat | Gastric Secretion | Antagonism | | Platelet Aggregation |
| | | Stomache | Colon | Rectum | Aorta | | | | | | | PGE1 | PGF2A | |
| --- | --- | --- | --- | --- | --- | --- | --- | --- | --- | --- | --- | --- | --- | --- |
| 17 | 4839 | 0 | 0 | 0 | 0 | 0 | R1 | — | — | — | 1 | — | — | +1 |
| 18 | 4767 | 2 | 0 | 1 | 0 | 0 | R0 | 0 | 0 | 0 | 0 | 0 | 0 | +2 |
|    | 4768 | 1 | 0 | 1 | 0 | 0 | R2 | — | — | — | 0 | 0 | 0 | +2 |
| 19 | 4717 | 1 | 0 | 0 | 0 | 0 | R3 | 1 | 2 | 0 | 3 | 1 | 0 | +1 |
| 20 | 4800 | 0 | 0 | 0 | 0 | 0 | R4 | 0 | 1 | 0 | 3 | 0 | 0 | +1 |
|    | 4802 | 0 | 0 | 0 | 0 | 0 | R0 | — | — | — | 0 | 0 | 0 | +1 |
| 21 | 4808 | 0 | 0 | 0 | 0 | 0 | R0 | 0 | 0 | 0 | 1 | 0 | 0 | +1 |
|    | 4807 | 0 | 0 | 0 | 0 | 0 | R0 | — | — | — | 0 | 0 | 0 | +1 |
| 22 | 4809 | 0 | 0 | 0 | 0 | 0 | R4 | — | — | — | 3 | 1 | 0 | +1 |

TABLE I-continued

| Example No. | TR Number | Cascade Stomache | Cascade Colon | Cascade Rectum | Aorta | Rat Uterus | Guinea Pig Trachea | Feline Blood Pressure, Heart Rate | Femoral Blood Flow | Blood Pressure Hypertensive Rat | Gastric Secretion | Antagonism PGE1 | Antagonism PGF2A | Platelet Aggregation |
|---|---|---|---|---|---|---|---|---|---|---|---|---|---|---|
| | 4801 | 0 | 0 | 0 | 0 | 0 | R0 | — | — | — | 0 | 0 | 0 | +1 |
| 23 | 4883 | 0 | 0 | 0 | 0 | 0 | R4 | 1 | — | 1 | 3 | 0 | 0 | +2 |
| 24 | 4978 | — | — | — | — | — | R4 | — | — | — | 0 | — | — | +1 |
| | 4979 | — | — | — | — | — | R3 | — | — | — | 0 | — | — | +1 |
| 25 | 4980 | | | | | | | | | | | | | |
| | 4981 | 0 | 0 | 0 | — | — | R2 | — | — | — | 0 | — | — | +1 |

What is claimed is:

1. A therapeutic method for producing bronchodilation in an individual for whom such therapy is indicated, comprising: administering to the individual an effective bronchodilating amount of a compound having the formula:

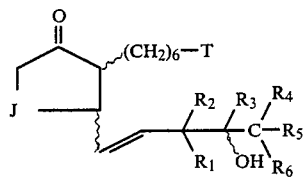

wherein:
J is selected from the group consisting of R-hydroxymethylene and S-hydroxymethylene;
T is alkoxycarbonyl having from 2 to 3 carbon atoms inclusive;
$R_1$ is hydrogen;
$R_2$ is hydrogen or together with $R_4$ is a methylene chain of 3 carbon atoms such that a cycloalkyl of 6 carbons atoms inclusive is formed;
$R_3$ is hydrogen or together with $R_4$ is a methylene or a lower alkylated methylene chain of 4 carbon atoms such that a cycloalkyl of 6 carbon atoms inclusive is formed, or together with $R_4$ is a bicycloalkyl or bicycloalkenyl moiety having the formula:

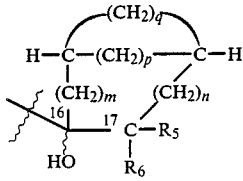

such that a bicycloalkyl or bicycloalkenyl compound is formed, wherein m and n are integers having a value of from 0 to 3, p is an integer having a value of from 0 to 4 and q is an integer having a value of from 1 to 4, and wherein the double bond of such bicycloalkenyl is in the m, n, p or q bridge;
$R_4$ is as defined above or is together with $R_5$ a methylene chain of 3 to 4 carbon atoms such that cycloalkyl of 4 to 5 carbon atoms inclusive is formed; and
$R_6$ is H or a straight-chain alkyl of 1 to 3 carbon atoms.

2. A therapeutic method as claimed in claim 1 wherein the compound is methyl 15R,20-cyclo-11α,16S-dihydroxy-9-oxoprost-13E-en-1-oate.

3. A therapeutic method as claimed in claim 1 wherein the compound is methyl 11α,16-dihydroxy-16,20-methano-9-oxoprost-13E-en-1-oate.

4. A therapeutic method as claimed in claim 1 wherein the compound is methyl 11α,16RS-dihydroxy-16,18-methano-17,20-methano-9-oxoprosta-13E,19-dien-1-oate.

5. A therapeutic method as claimed in claim 1 wherein the compound is methyl 11α,16RS-dihydroxy-16,18-methano-17,20-methano-9-oxoprost-13E-en-1-oate.

6. A therapeutic method as claimed in claim 1 wherein the compound is methyl 11α,16RS-dihydroxy-16,20-methano-17,20-methano-9-oxoprost-13E-en-1-oate.

7. A therapeutic method as claimed in claim 1 wherein the compound is methyl 11α,16S-dihydroxy-9-oxo-17,17-propanoprost-13E-en-1-oate.

8. A therapeutic method as claimed in claim 1 wherein the compound is methyl 11α,16R-dihydroxy-9-oxo-17,17-propanoprost-13E-en-1-oate.

9. A therapeutic method as claimed in claim 1 wherein the compound is methyl 11α,16RS-dihydroxy-17,20-methano-17-methyl-9-oxoprost-13E-en-1-oate.

* * * * *